United States Patent
Prentice

(10) Patent No.: US 12,366,580 B2
(45) Date of Patent: Jul. 22, 2025

(54) METHODS FOR MASS SPECTROMETRY ANALYSIS OF ENGINEERED CELL COMPOSITIONS

(71) Applicant: Juno Therapeutics, Inc., Seattle, WA (US)

(72) Inventor: Kenneth Mayo Prentice, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 1164 days.

(21) Appl. No.: 17/274,770

(22) PCT Filed: Sep. 11, 2019

(86) PCT No.: PCT/US2019/050681
§ 371 (c)(1),
(2) Date: Mar. 9, 2021

(87) PCT Pub. No.: WO2020/056047
PCT Pub. Date: Mar. 19, 2020

(65) Prior Publication Data
US 2022/0050114 A1  Feb. 17, 2022

Related U.S. Application Data

(60) Provisional application No. 62/729,985, filed on Sep. 11, 2018.

(51) Int. Cl.
| | | |
|---|---|---|
| G01N 33/68 | (2006.01) | |
| A61K 39/00 | (2006.01) | |
| C07K 14/725 | (2006.01) | |
| C12N 5/0783 | (2010.01) | |
| G01N 30/72 | (2006.01) | |
| G01N 33/569 | (2006.01) | |

(52) U.S. Cl.
CPC ...... *G01N 33/6848* (2013.01); *A61K 39/0011* (2013.01); *C07K 14/7051* (2013.01); *C12N 5/0636* (2013.01); *G01N 30/7233* (2013.01); *G01N 33/56966* (2013.01); *A61K 2039/5156* (2013.01); *A61K 2039/5158* (2013.01)

(58) Field of Classification Search
CPC .......... G01N 33/6848; G01N 30/7233; G01N 33/56966; C07K 14/7051; C12N 5/0636
See application file for complete search history.

(56) References Cited

U.S. PATENT DOCUMENTS

| | | |
|---|---|---|
| 4,452,773 A | 6/1984 | Molday |
| 4,795,698 A | 1/1989 | Owen et al. |
| 5,168,049 A | 12/1992 | Meade et al. |
| 5,200,084 A | 4/1993 | Liberti et al. |
| 5,219,740 A | 6/1993 | Miller et al. |
| 5,506,121 A | 4/1996 | Skerra et al. |
| 5,840,306 A | 11/1998 | Hofman et al. |
| 6,040,177 A | 3/2000 | Riddell et al. |
| 6,060,273 A | 5/2000 | Dirks et al. |
| 6,103,493 A | 8/2000 | Skerra et al. |
| 6,123,655 A | 9/2000 | Fell et al. |
| 6,207,453 B1 | 3/2001 | Maass et al. |
| 6,410,319 B1 | 6/2002 | Raubitschek et al. |
| 6,451,995 B1 | 9/2002 | Cheung et al. |
| 6,531,127 B2 | 3/2003 | Muller et al. |
| 6,733,433 B1 | 5/2004 | Fell et al. |
| 7,070,995 B2 | 7/2006 | Jensen |
| 7,265,209 B2 | 9/2007 | Jensen |
| 7,354,762 B2 | 4/2008 | Jensen |
| 7,446,179 B2 | 11/2008 | Jensen et al. |
| 7,446,190 B2 | 11/2008 | Sadelain et al. |
| 7,446,191 B2 | 11/2008 | Jensen |
| 7,776,562 B2 | 8/2010 | Busch et al. |
| 7,981,632 B2 | 7/2011 | Schmidt et al. |
| 8,298,782 B2 | 10/2012 | Busch et al. |
| 8,324,353 B2 | 12/2012 | Jensen |
| 8,339,645 B2 | 12/2012 | Nakawaki |

(Continued)

FOREIGN PATENT DOCUMENTS

| | | |
|---|---|---|
| EP | 0 452 342 | 11/1994 |
| EP | 2 537 416 | 12/2012 |

(Continued)

OTHER PUBLICATIONS

US 8,252,592 B2, 08/2012, Sadelain (withdrawn)

(Continued)

*Primary Examiner* — Elizabeth C. Kemmerer
*Assistant Examiner* — Mckenzie A Dunn
(74) *Attorney, Agent, or Firm* — Morrison & Foerster LLP

(57) ABSTRACT

Provided herein are methods for generating a mass spectrometry (MS) profile of a sample from a cell composition, such as an engineered cell composition. In some embodiments, the mass spectrometry profile includes data based on one or more mass spectrometry analyses or techniques. Also provided herein are methods for, based on mass spectrometry profiles of one or more samples of such cell compositions: identifying a mass spectrometry (MS) profile of a genetically engineered cell composition comprising immune cells comprising a recombinant receptor by comparison to a reference mass spectrometry profile; characterizing a process for producing genetically engineered cell composition; assessing cell surface proteins of an engineered cell composition; and assessing a process for producing a genetically engineered cell composition.

21 Claims, 7 Drawing Sheets
Specification includes a Sequence Listing.

(56) References Cited

U.S. PATENT DOCUMENTS

| | | | |
|---|---|---|---|
| 8,361,473 | B2 | 1/2013 | Makler et al. |
| 8,389,282 | B2 | 3/2013 | Sadelain et al. |
| 8,479,118 | B2 | 7/2013 | Lindersay |
| 8,735,540 | B2 | 5/2014 | Schmidt et al. |
| 8,802,374 | B2 | 8/2014 | Jensen |
| 8,822,647 | B2 | 8/2014 | Jensen |
| 8,911,993 | B2 | 12/2014 | June et al. |
| 9,023,604 | B2 | 5/2015 | Schmidt et al. |
| 9,233,125 | B2 | 1/2016 | Davila et al. |
| 2002/0131960 | A1 | 9/2002 | Sadelain et al. |
| 2002/0150914 | A1 | 10/2002 | Anderson et al. |
| 2003/0223994 | A1 | 12/2003 | Hoogenboom et al. |
| 2004/0086521 | A1 | 5/2004 | Karpshofer et al. |
| 2004/0191260 | A1 | 9/2004 | Reiter et al. |
| 2006/0034850 | A1 | 2/2006 | Weidanz et al. |
| 2007/0092530 | A1 | 4/2007 | Weidanz et al. |
| 2007/0099253 | A1 | 5/2007 | Erkhov et al. |
| 2007/0116690 | A1 | 5/2007 | Yang et al. |
| 2007/0134806 | A1 | 6/2007 | Yoshiya et al. |
| 2007/0176088 | A1 | 8/2007 | Li |
| 2008/0171951 | A1 | 7/2008 | Fell et al. |
| 2009/0226474 | A1 | 9/2009 | Weidanz et al. |
| 2009/0304679 | A1 | 12/2009 | Weidanz |
| 2011/0003380 | A1 | 1/2011 | Miltenyi et al. |
| 2012/0308580 | A1 | 12/2012 | Bertoletti et al. |
| 2013/0149337 | A1 | 6/2013 | Cooper et al. |
| 2013/0287748 | A1 | 10/2013 | June et al. |
| 2014/0179011 | A1 | 6/2014 | Brousmiche et al. |
| 2014/0002427 | A1 | 8/2014 | Brousmiche et al. |
| 2014/0002716 | A1 | 9/2014 | Brodgon et al. |
| 2014/0294841 | A1 | 10/2014 | Scheinberg et al. |
| 2017/0051035 | A1 | 2/2017 | Payne et al. |
| 2021/0255173 | A1* | 8/2021 | Kodama ............ G01N 33/5308 |

FOREIGN PATENT DOCUMENTS

| | | |
|---|---|---|
| JP | 2009103718 | 5/2009 |
| WO | WO 1992/008796 | 5/1992 |
| WO | WO 1994/028143 | 12/1994 |
| WO | WO 1996/013593 | 5/1996 |
| WO | WO 1996/018105 | 6/1996 |
| WO | WO 1999/018129 | 4/1999 |
| WO | WO 1999/060120 | 11/1999 |
| WO | WO 2000/014257 | 3/2000 |
| WO | WO 2000/038762 | 7/2000 |
| WO | WO 2003/020763 | 3/2003 |
| WO | WO 2003/068201 | 8/2003 |
| WO | WO 2004/033685 | 4/2004 |
| WO | WO 2006/000830 | 1/2006 |
| WO | WO 2006/037960 | 4/2006 |
| WO | WO 2008/123793 | 10/2008 |
| WO | WO 2009/027041 | 3/2009 |
| WO | WO 2009/072003 | 6/2009 |
| WO | WO 2010/033140 | 3/2010 |
| WO | WO 2011/044186 | 4/2011 |
| WO | WO 2012/129514 | 9/2012 |
| WO | WO 2013/071154 | 5/2013 |
| WO | WO 2013/123061 | 8/2013 |
| WO | WO 2013/124474 | 8/2013 |
| WO | WO 2013/126726 | 8/2013 |
| WO | WO 2013/166321 | 11/2013 |
| WO | WO 2014/031687 | 2/2014 |
| WO | WO 2014/055668 | 4/2014 |
| WO | WO 2014/076277 | 5/2014 |
| WO | WO 2015/009604 | 1/2015 |
| WO | WO 2015/009606 | 1/2015 |
| WO | WO 2015/075139 | 5/2015 |
| WO | WO 2015/164675 | 10/2015 |
| WO | WO 2015/184228 | 12/2015 |
| WO | WO 2016/030414 | 3/2016 |
| WO | WO 2016/036705 | 3/2016 |
| WO | WO 2016/073602 | 5/2016 |
| WO | WO 2018/027197 | 2/2018 |
| WO | WO 2018/157171 | 8/2018 |

OTHER PUBLICATIONS

Schiess, Ralph et al. "Analysis of cell surface proteome changes via label-free, quantitative mass spectrometry." Molecular & cellular proteomics : MCP vol. 8,4 (2009): 624-38. doi: 10.1074/mcp.M800172-MCP200 (Year: 2009).*

Addo et al. "Fully differentiated HIV-1 specific CD8+ T effector cells are more frequently detectable in controlled than in progressive HIV-1 infection." PloS one (2007) 2.3: e321.

Alonso-Camino et al., "CARbodies: Human Antibodies Against Cell Surface Tumor Antigens Selected From Repertoires Displayed on T Cell Chimeric Antigen Receptors," Mol Ther Nucleic Acids (2013) 2(5):e93.

Anikeeva et al. "Can oligomeric T-cell receptor be used as a tool to detect viral peptide epitopes on infected cells?." Clinical Immunology (2009) 130.1: 98-109.

Anumula et al., "Advances in Fluorescence Derivatization Methods for High-Performance Liquid Chromatographic Analysis of Glycoprotein Carbohydrates," Anal Biochem (2006) 350(1): 1-23.

Barrett et al., "Chimeric Antigen Receptor Therapy for Cancer," Annual Review of Medicine (2014) 65:333-347.

Bateman et al., "Glycan analysis and influenza A virus infection of primary swine respiratory epithelial cells: the importance of NeuAc{alpha}2-6 glycans." J Biol Chem. (Oct. 29, 2010) ;285(44):34016-34026.

Boris-Lawrie et al., "Recent advances in retrovirus vector technology," Current Opinion in Genetics & Development (1993) 3(1):102-109.

Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.

Brentjens et al., "CD19-targeted T cells rapidly induce molecular remissions in adults with chemotherapy-refractory acute lymphoblastic leukemia," Sci Transl Med. (2013) 5(177):177ra38.

Bulek et al. "Structural basis for the killing of human beta cells by CD8+ T cells in type 1 diabetes." Nature immunology (2012) 13.3: 283-289.

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.

Carlens et al., "Ex vivo T lymphocyte expansion for retroviral transduction: influence of serum-free media on variations in cell expansion rates and lymphocyte subset distribution," Exp Hematol (2000) 28(10): 1137-1146.

Carrillo et al., "The Multiple Sequence Alignment Problem in Biology," SIAM J Appl Math (1988) 48(5):1073-1082.

Cavalieri et al., "Human T lymphocytes transduced by lentiviral vectors in the absence of TCR activation maintain an intact immune competence," Blood (2003) 102(2): 497-505.

Cheadle et al., "Chimeric antigen receptors for T-cell based therapy," Methods Mol Biol. (2012);907:645-66.

Cheever et al. "The prioritization of cancer antigens: a national cancer institute pilot project for the acceleration of translational research." Clinical cancer research (2009) 15.17: 5323-5337.

Chervin et al., "Engineering higher affinity T cell receptors using a T cell display system," J Immunol Methods (2008) 339(2):175-184.

Chicaybam et al., "An efficient low cost method for gene transfer to T lymphocytes," PLoS One (2013) 8(3): e60298.

Cho et al., "Human mammalian cell sorting using a highly integrated micro-fabricated fluorescence-activated cell sorter (microFACS)," Lab Chip (2010) 10: 1567-1573.

Chothia et al., "The outline structure of the T-cell alpha beta receptor," EMBO J (1988) 7(12):3745-3755.

Clackson et al. "Making Antibody Fragments Using Phage Display Libraries," Nature (1991) 352:624-628.

Cohen et al., "Recognition of fresh human tumor by human peripheral blood lymphocytes transduced with a bicistronic retroviral vector encoding a murine anti-p53 TCR," J Immunol. (2005) 175:5799-5808.

(56) References Cited

OTHER PUBLICATIONS

Cohen et al., "Recombinant antibodies with MHC-restricted, peptide-specific, T-cell receptor-like specificity: new tools to study antigen presentation and TCR-peptide-MHC interactions," J Mol Recognit. (2003) 16(5):324-332.
Comelli et al., "Activation of Murine CD4+ and CD8+ T Lymphocytes Leads to Dramatic Remodeling of N-linked Glycans," J Immunol (2006) 177(4): 2431-2440.
Cooper et al., "T-cell clones can be rendered specific for CD19: toward the selective augmentation of the graft-versus-B-lineage leukemia effect," Blood (2003) 101:1637-1644.
Davila et al., "CD19 CAR-Targeted T Cells Induce Long-Term Remission and B Cell Aplasia in an Immunocompetent Mouse Model of B Cell Acute Lymphoblastic Leukemia," PLOS One (2013) 8(4):e61338.
De Felipe et al., "Targeting of Proteins Derived from Self-Processing Polyproteins Containing Multiple Signal Sequences," Traffic (2004) 5(8):616-626.
De Felipe, "Skipping the co-expression problem: the new 2A "CHYSEL" technology," Genet Vaccines Ther (2004) 2:13.
Earl et al., "CD45 Glycosylation Controls T-cell Life and Death," Immunol Cell Biol (2008) 86(7): 608-615.
Eshghi et al., "Imaging of N-Linked Glycans from Formalin-Fixed Paraffin-Embedded Tissue Sections Using MALDI Mass Spectrometry." ACS Chemical Biology (2014) 9(9): 2149-2156.
Fedorov et al., "PD-1- and CTLA-4-based inhibitory chimeric antigen receptors (iCARs) divert off-target immunotherapy responses," Sci Transl Med. (2013) 5(215):215ra172.
Gan et al., "Native Mass Spectrometry of Recombinant Proteins From Crude Cell Lysates," Anal Chem (2017) 89(8): 4398-4404.
Gimenez et al., "Quantitative analysis of N-glycans from human alfa-acid-glycoprotein using stable isotope labeling and zwitterionic hydrophilic interaction capillary liquid chromatography electrospray mass spectrometry as tool for pancreatic disease diagnosis." Anal Chim Acta. (2015) 866:59-68.
Godin et al., "Microfluidics and photonics for Bio-System-on-a-Chip: a review of advancements in technology towards a microfluidic flow cytometry chip," J Biophotonics (2008) 1(5):355-376.
Gotze et al., "Diagnosis of toxoplasmosis using a synthetic glycosylphosphatidylinositol glycan." Angew Chem Int Ed Engl. (2014) 53(50):13701-13705.
Hall et al., "Cell Surface N-glycans Influence the Level of Functional E-cadherin at the Cell-Cell Border," FEBS Open Bio (2014) 4: 892-897.
Hara et al., "Determination of mono-O-acetylated N-acetylneuraminic Acids in Human and Rat Sera by Fluorometric High-Performance Liquid Chromatography," Anal Biochem (1989) 179(1): 162-66.
Harkiolaki et al. "T cell-mediated autoimmune disease due to low-affinity crossreactivity to common microbial peptides." *Immunity* (2009) 30.3: 348-357.
Hauskins., "JCAR017 MOA and EOS," Juno Therapeutics. Presentation Deck. Presented in 2018.
Hauskins., "JCAR017 EoS Sequence ID." Juno Therapuetics. Presentation Deck. Presented in 2018.
Holler et al., "In vitro evolution of a T cell receptor with high affinity for peptide/MHC," PNAS (2000) 97(10):5387-5392.
Holler et al., "TCRs with high affinity for foreign pMHC show self-reactivity," Nat Immunol (2003) 4(1):55-62.
Huang et al., "DNA transposons for modification of human primary T lymphocytes," Methods Mol Biol (2009) 506:115-126.
Hudecek et al., "Receptor affinity and extracellular domain modifications affect tumor recognition by ROR1-specific chimeric antigen receptor T cells," Clin Cancer Res (2013) 19(12):3153-3164.
Hudecek et al., "The nonsignaling extracellular spacer domain of chimeric antigen receptors is decisive for in vivo antitumor activity," Cancer Immunol Res (2015) 3(2):125-135.
Isailovic et al., "Delineating diseases by IMS-MS profiling of serum N-linked glycans." J Proteome Res. (2012) 11(2):576-85.
Janeway et al., Immunobiology: The Immune System in Health and Disease, 3rd ED., Current Biology Publications (1997), p. 4:33.

Johnston, "Biolistic transformation: microbes to mice," Nature (1990) 346:776-777.
Jores et al., "Resolution of hypervariable regions in T-cell receptor beta chains by a modified Wu-Kabat index of amino acid diversity.," PNAS (1990) 87(23):9138-9142.
Kindt, T.J. et al. (2007). "Antigens And Antibodies," Chapter 4 In Kuby Immunology 6th Ed., W.H. Freeman And Co., p. 91.
Kaech et al. "Effector and memory T-cell differentiation: implications for vaccine development." *Nature Reviews Immunology* (2002) 2.4: 251-262.
Klebanoff et al., "Sorting through subsets: Which T cell populations mediate highly effective adoptive immunotherapy?" J Immunother (2012) 35(9):651-660.
Kochenderfer et al., "Treating B-cell cancer with T cells expressing anti-CD19 chimeric antigen receptors," Nat Rev Clin Oncol (2013) 10(5):267-276.
Koste et al., "T-cell receptor transfer into human T cells with ecotropic retroviral vectors," Gene Therapy (2014) 21:533-538.
Kotb et al., "Bacterial pyrogenic exotoxins as superantigens," Clinical Microbiology Reviews (1995) 8:411-426.
Kuball et al. "Facilitating matched pairing and expression of TCR chains introduced into human T cells." *Blood* (2007) 109.6: 2331-2338.
Kurucz et al., "A bacterially expressed single-chain Fv construct from the 2B4 T-cell receptor," PNAS (1993) 90(9):3830-3834.
Lauber et al., "Rapid Preparation of Released N-Glycans for HILIC Analysis Using a Novel Flourescence and MS-Active Labeling Reagent," Application Note from Waters Corporation (Waters.com) downloaded Mar. 28, 2017.
Lefranc et al., "IMGT unique numbering for immunoglobulin and T cell receptor variable domains and Ig superfamily V-like domains," Dev Comp Immunol (2003) 27(1):55-77.
Li et al., "Directed evolution of human T-cell receptors with picomolar affinities by phage display," Nat Biotechnol (2005) 23(3):349-354.
Li et al., "Glycosylation and Stabilization of Programmed Death ligand-1 Suppresses T-cell Activity," Nat Commun (2016) 7: 12632.
Ling et al., "B-cell and plasma cell antigens: new and previously defined clusters," Leucocyte typing 111. (1987) 302-355.
Liu et al., "Cell Surface-Specific N-glycan Profiling in Breast Cancer," PLoS One (2013) 8(8): e72704.
Liu et al., "Inclusion of Strep-tag II in design of antigen receptors for T-cell immunotherapy," Nat Biotechnol (2016) 34(4):430-434.
Lupton et al., "Dominant positive and negative selection using a hygromycin phosphotransferase-thymidine kinase fusion gene," Mol and Cell Biol (1991) 11(6):3374-3378.
Manuri et al., "piggyBac Transposon/Transposase System to Generate CD19-Specific T Cells for the Treatment of B-Lineage Malignancies, " Hum Gene Ther (2010) 21(4):427-437.
Mehta et al., "Intrinsic Hepatocyte Dedifferentiation Is Accompanied by Upregulation of Mesenchymal Markers, Protein Sialylation and Core Alpha 1,6 Linked Fucosylation," Sci Rep (2016) 6: 27965.
Miller et al., "Improved retroviral vectors for gene transfer and expression," Biotechniques (1989) 7(9):980-990.
Miller, "Retrovirus packaging cells," Hum Gene Ther (1990) 1(1):5-14.
Miwa et al., "Bisected, complex N-glycans and galectins in mouse mammary tumor progression and human breast cancer." Glycobiology (2013) 23(12): 1477-1490.
Mullen et al., "Transfer of the bacterial gene for cytosine deaminase to mammalian cells confers lethal sensitivity to 5-fluorocytosine: A negative selection system," Proc Natl Acad Sci U.S.A (1992) 89:33-37.
Nabi et al., "The Galectin Lattice at a Glance," J Cell Sci (2015) 128(13): 2213-2219.
Naldini et al. "Lentiviruses as gene transfer agents for delivery to non-dividing cells." *Current opinion in biotechnology* 9.5 (1998): 457-463.
N-Glycosidase F, recombinant. Information Sheet, Roche Applied Science, Content version Jun. 2005.
Norton et al., "Development and Application of a Novel Recombinant Aleuria Aurantia Lectin With Enhanced Core Fucose Binding

(56) References Cited

OTHER PUBLICATIONS for Identification of Glycoprotein Biomarkers of Hepatocellular Carcinoma," Proteomics (2016) 16(24): 3126-3136.
Ohta et al., "Expression of Sialyl Lewis(x) Antigen on Human T Cells," Cell Immunol (1993) 151(2): 491-497.
Ouedraogo et al., "Global Analysis of Circulating Immune Cells by Matrix-Assisted Laser Desorption Ionization Time-Of-Flight Mass Spectrometry," PLoS One (2010) 5(10): e13691.
Park et al., "Treating cancer with genetically engineered T cells," Trends Biotechnol (2011) 29(11):550-557.
Parkhurst et al., "Characterization of genetically modified T-cell receptors that recognize the CEA:691-699 peptide in the context of HLA-A2.1 on human colorectal cancer cells," Clin Cancer Res. (2009) 15:169-180.
Plummer et al., "Demonstration of peptide:N-glycosidase F Activity in endo-beta-N- acetylglucosaminidase F Preparations," J Biol Chem (1984) 259(17): 10700-10704.
PNGaseF Protocol Prime, User Manual Dated Oct. 14, 2015, N-Zyme Scientifics.
PNGaseF Sheet, QA-Bio, dated Dec. 2, 2014.
Portolano et al. "Lack of Promiscuity in Autoantigen-Specific H and L Chain Combinations as Revealed by Human H And L Chain 'Roulette'," The Journal of Immunology (1993) 150(3):880-887.
Powers et al. "Matrix assisted laser desorption ionization imaging mass spectrometry workflow for spatial profiling analysis of N-linked glycan expression in tissues." Analytical chemistry 85.20 (2013): 9799-9806.
Powers et al., "Two-Dimensional N-Glycan Distribution Mapping of Hepatocellular Carcinoma Tissues by MALDI-Imaging Mass Spectrometry," Biomolecules (2015) 5(4): 2554-2572.
Prentice et al., "Mass Spectrometry in the CAR-T Development Lab," Abstract. Presented in 2018.
Prentice et al., "Mass Spectrometry in the CAR-T Development Lab," Presentation Deck. Presented in 2018.
PROzyme InstantAB instruction manual, "Rapid N-Glycan Preparation with InstantAB" www.prozyme.com.
Restifo. "Big bang theory of stem-like T cells confirmed." Blood, The Journal of the American Society of Hematology (2014) 124.4: 476-477.
Riddell et al., "Phase I Study of Cellular Adoptive Immunotherapy Using Genetically Modified CD8+ HIV-Specific T Cells for HIV Seropositive Patients Undergoing Allogeneic Bone Marrow Transplant," Human Gene Therapy (1992) 3:319-338.
Ruhaak et al. "Glycan labeling strategies and their use in identification and quantification." Analytical and bioanalytical chemistry (2010) 397.8: 3457-3481.
Sadelain et al., "The basic principles of chimeric antigen receptor (CAR) design," Cancer Discov (2013) 3(4):388-398.
Scarpa et al., "Characterization of recombinant helper retroviruses from Moloney-based vectors in ecotropic and amphotropic packaging cell lines," Virology (1991) 180(2):849-852.
Schlueter et al., "Specificity and Binding Properties of a Single-chain T Cell Receptor," J Mol Biol (1996) 256(5):859-869.
Schuler et al., "SYFPEITHI: database for searching and T-cell epitope prediction," Methods Mol Biol. (2007) 409: 75-93.
Sharma et al., "Efficient Sleeping Beauty DNA Transposition From DNA Minicircles," Molec Ther Nucl Acids (2013) 2:e74.
Singh et al., "ProPred: prediction of HLA-DR binding sites," Bioinformatics (2001) 17(12):1236-1237.
Skowera et al. "CTLs are targeted to kill ß cells in patients with type 1 diabetes through recognition of a glucose-regulated preproinsulin epitope." The Journal of clinical investigation (2008) 118.10: 3390-3402.
Soo Hoo et al., "Characterization of a single-chain T-cell receptor expressed in Escherichia coli," PNAS (1992) 89(10):4759-4763.
Steinke et al., "The alpha gal story: Lessons learned from connecting the dots." J Allergy Clin Immunol. (2015); 135(3): 589-597.

Tamada et al. "Redirecting gene-modified T cells toward various cancer types using tagged antibodies." Clinical Cancer Research (2012) 18.23: 6436-6445.
Tarentino et al. "Molecular cloning and amino acid sequence of peptide-N4-(N-acetyl-beta-D-glucosaminyl) asparagine amidase from flavobacterium meningosepticum." Journal of Biological Chemistry (1990) 265.12: 6961-6966.
Terakura et al., "Generation of CD19-chimeric antigen receptor modified CD8+ T cells derived from virus-specific central memory T cells," Blood (2012) 119(1):72-82.
Townsend, R. R. Carbohydrate Analysis High Performance Liquid Chromatography and Capillary Electrophoresis., Ed. Z. El Rassi, pp. 181-209, 1995.
Tsomides et al. "Naturally processed viral peptides recognized by cytotoxic T lymphocytes on cells chronically infected by human immunodeficiency virus type 1." The Journal of experimental medicine (1994) 180.4: 1283-1293.
Turtle et al., "Engineered T cells for anti-cancer therapy," Engineered T cells for anti-cancer therapy, Curr Opin Immunol (2012) 24(5):633-639.
Urbanska et al. "A universal strategy for adoptive immunotherapy of cancer through use of a novel T-cell antigen receptor." Cancer research (2012) 72.7: 1844-1852.
Utz et al. "Analysis of the T-cell receptor repertoire of human T-cell leukemia virus type 1 (HTLV-1) Tax-specific CD8+ cytotoxic T lymphocytes from patients with HTLV-1-associated disease: evidence for oligoclonal expansion." Journal of virology (1996) 70.2: 843-851.
Van Tendeloo et al., "High-level transgene expression in primary human T lymphocytes and adult bone marrow CD34+ cells via electroporation-mediated gene delivery," Gene Therapy (2000) 7(16): 1431-1437.
Varela-Rohena et al., "Control of HIV-1 immune escape by CD8 T cells expressing enhanced T-cell receptor," Nat Med. (2008) 14:1390-1395.
Verhoeyen et al., "Lentiviral vector gene transfer into human T cells," Methods Mol Biol (2009) 506:97-114.
Vigneron et al. "Database of T cell-defined human tumor antigens: the 2013 update." Cancer Immunity Archive (2013) 13.3.
Wang et al., "Glycan-based diagnostic devices: current progress, challenges and perspectives." Chem Commun (Camb). (2015) 51(94): 16750-16762.
Wang et al., "Phenotypic and Functional Attributes of Lentivirus Modified CD19-specific Human CD8+ Central Memory T Cells Manufactured at Clinical Scale," J Immunother (2012) 35(9):689-701.
Wigler et al., "Transfer of Purified Herpes Virus Thymidine Kinase Gene to Cultured Mouse Cells," Cell (1997) 2:223.
Wu et al., "Adoptive T-cell therapy using autologous tumor-infiltrating lymphocytes for metastatic melanoma: current status and future outlook," Cancer J (2012) 18(2):160-175.
Wulfing et al., "Correctly folded T-cell receptor fragments in the periplasm of Escherichia coli. Influence of folding catalysts," J Mol Biol (1994) 242(5):655-669.
Yang et al., "Quantitative glycome analysis of N-glycan patterns in bladder cancer vs normal bladder cells using an integrated strategy." J Proteome Res. (2015) 14(2): 639-653.
Zhang et al., "Characterizations of Vector and CAR-T Cells Protein by Separation Methods," Abstract. Presented in 2020.
Zhang et al., "Discovery of specific metastasis-related N-glycan alterations in epithelial ovarian cancer based on quantitative glycomics." PLoS One. (2014) 9(2): e87978.
Davila et al., "Efficacy and toxicity management of 19-28z CAR T cell therapy in B cell acute lymphoblastic leukemia," Sci Transl Med (2014) 6:224ra25.
Nunomura et al., "Cell Surface Labeling and Mass Spectrometry Reveal Diversity of Cell Surface Markers and Signaling Molecules Expressed in Undifferentiated Mouse Embryonic Stem Cells," Molecular & Cellular Proteomics (Sep. 2005) 4(12):1968-1976.

* cited by examiner

SEQUENCE LISTING

<160> NUMBER OF SEQ ID NOS: 61

<210> SEQ ID NO 1
<211> LENGTH: 12
<212> TYPE: PRT
<213> ORGANISM: Homo sapiens
<220> FEATURE:
<223> OTHER INFORMATION: spacer (IgG4hinge)

<400> SEQUENCE: 1

Glu Ser Lys Tyr Gly Pro Pro Cys Pro Pro Cys Pro
1               5                   10

<210> SEQ ID NO 2
<211> LENGTH: 36
<212> TYPE: DNA
<213> ORGANISM: Homo sapiens
<220> FEATURE:
<223> OTHER INFORMATION: spacer (IgG4hinge)

<400> SEQUENCE: 2
gaatctaagt acggaccgcc ctgcccccct tgccct                                36

<210> SEQ ID NO 3
<211> LENGTH: 119
<212> TYPE: PRT
<213> ORGANISM: Homo sapiens
<220> FEATURE:
<223> OTHER INFORMATION: Hinge-CH3 spacer

<400> SEQUENCE: 3

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
                20                  25                  30

Asn Gln Val Ser Leu Thr Cys Leu Val Lys Gly Phe Tyr Pro Ser Asp
            35                  40                  45

Ile Ala Val Glu Trp Glu Ser Asn Gly Gln Pro Glu Asn Asn Tyr Lys
        50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Gln Gly Asn Val Phe Ser
                85                  90                  95

Cys Ser Val Met His Glu Ala Leu His Asn His Tyr Thr Gln Lys Ser
                100                 105                 110

Leu Ser Leu Ser Leu Gly Lys
        115

<210> SEQ ID NO 4
<211> LENGTH: 229
<212> TYPE: PRT
<213> ORGANISM: Homo sapiens
<220> FEATURE:
<223> OTHER INFORMATION: Hinge-CH2-CH3 spacer

<400> SEQUENCE: 4

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

```
Ser Gln Glu Asp Pro Glu Val Gln Phe Asn Trp Tyr Val Asp Gly Val
 50                  55                  60

Glu Val His Asn Ala Lys Thr Lys Pro Arg Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
            210                 215                 220

Leu Ser Leu Gly Lys
225

<210> SEQ ID NO 5
<211> LENGTH: 282
<212> TYPE: PRT
<213> ORGANISM: Homo sapiens
<220> FEATURE:
<223> OTHER INFORMATION: IgD-hinge-Fc

<400> SEQUENCE: 5

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
                20                  25                  30

Thr Thr Arg Asn Thr Gly Arg Gly Gly Glu Glu Lys Lys Lys Glu Lys
            35                  40                  45

Glu Lys Glu Glu Gln Glu Glu Arg Glu Thr Lys Thr Pro Glu Cys Pro
 50                  55                  60

Ser His Thr Gln Pro Leu Gly Val Tyr Leu Leu Thr Pro Ala Val Gln
 65                  70                  75                  80

Asp Leu Trp Leu Arg Asp Lys Ala Thr Phe Thr Cys Phe Val Val Gly
                 85                  90                  95

Ser Asp Leu Lys Asp Ala His Leu Thr Trp Glu Val Ala Gly Lys Val
                100                 105                 110

Pro Thr Gly Gly Val Glu Glu Gly Leu Leu Glu Arg His Ser Asn Gly
            115                 120                 125

Ser Gln Ser Gln His Ser Arg Leu Thr Leu Pro Arg Ser Leu Trp Asn
            130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175
```

```
Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Gln Pro Gly Ser Thr Thr Phe Trp Ala Trp Ser
225                 230                 235                 240

Val Leu Arg Val Pro Ala Pro Ser Pro Gln Pro Ala Thr Tyr Thr
                245                 250                 255

Cys Val Val Ser His Glu Asp Ser Arg Thr Leu Leu Asn Ala Ser Arg
                260                 265                 270

Ser Leu Glu Val Ser Tyr Val Thr Asp His
            275                 280

<210> SEQ ID NO 6
<211> LENGTH: 24
<212> TYPE: PRT
<213> ORGANISM: Artificial Sequence
<220> FEATURE:
<223> OTHER INFORMATION: T2A

<400> SEQUENCE: 6

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 7
<211> LENGTH: 357
<212> TYPE: PRT
<213> ORGANISM: Artificial Sequence
<220> FEATURE:
<223> OTHER INFORMATION: tEGFR

<400> SEQUENCE: 7

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
```

```
                165                 170                 175
Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
            195                 200                 205

Pro Arg Asp Cys Val Ser Cys Arg Asn Val Ser Arg Gly Arg Glu Cys
            210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Leu Val Val Ala Leu Gly
            340                 345                 350

Ile Gly Leu Phe Met
        355

<210> SEQ ID NO 8
<211> LENGTH: 27
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 8

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 9
<211> LENGTH: 66
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 9

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45
```

Val Leu Ala Cys Tyr Ser Leu Leu Val Thr Val Ala Phe Ile Ile Phe
            50                  55                  60

Trp Val
65

<210> SEQ ID NO 10
<211> LENGTH: 41
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 10

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 11
<211> LENGTH: 41
<212> TYPE: PRT
<213> ORGANISM: Homo sapiens
<220> FEATURE:
<223> OTHER INFORMATION: CD28

<400> SEQUENCE: 11

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 12
<211> LENGTH: 42
<212> TYPE: PRT
<213> ORGANISM: Homo sapiens
<220> FEATURE:
<223> OTHER INFORMATION: 4-1BB
<300> PUBLICATION INFORMATION:
<308> DATABASE ACCESSION NUMBER: UniProt Q07011.1
<309> DATABASE ENTRY DATE: 1995-02-01

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 13
<211> LENGTH: 112
<212> TYPE: PRT
<213> ORGANISM: Homo sapiens
<220> FEATURE:
<223> OTHER INFORMATION: CD3 zeta

<400> SEQUENCE: 13

-continued

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 14
<211> LENGTH: 112
<212> TYPE: PRT
<213> ORGANISM: Homo sapiens
<220> FEATURE:
<223> OTHER INFORMATION: CD3 zeta

<400> SEQUENCE: 14

Arg Val Lys Phe Ser Arg Ser Ala Glu Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 15
<211> LENGTH: 112
<212> TYPE: PRT
<213> ORGANISM: Homo sapiens
<220> FEATURE:
<223> OTHER INFORMATION: CD3 zeta

<400> SEQUENCE: 15

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

```
Thr Lys Asp Thr Tyr Asp Ala Leu His Met Gln Ala Leu Pro Pro Arg
            100                 105                 110

<210> SEQ ID NO 16
<211> LENGTH: 335
<212> TYPE: PRT
<213> ORGANISM: Artificial Sequence
<220> FEATURE:
<223> OTHER INFORMATION: tEGFR

<400> SEQUENCE: 16

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 17
```

```
<211> LENGTH: 18
<212> TYPE: PRT
<213> ORGANISM: Artificial Sequence
<220> FEATURE:
<223> OTHER INFORMATION: T2A

<400> SEQUENCE: 17

Glu Gly Arg Gly Ser Leu Leu Thr Cys Gly Asp Val Glu Glu Asn Pro
1               5                   10                  15

Gly Pro

<210> SEQ ID NO 18
<211> LENGTH: 22
<212> TYPE: PRT
<213> ORGANISM: Artificial Sequence
<220> FEATURE:
<223> OTHER INFORMATION: P2A

<400> SEQUENCE: 18

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 19
<211> LENGTH: 19
<212> TYPE: PRT
<213> ORGANISM: Artificial Sequence
<220> FEATURE:
<223> OTHER INFORMATION: P2A

<400> SEQUENCE: 19

Ala Thr Asn Phe Ser Leu Leu Lys Gln Ala Gly Asp Val Glu Glu Asn
1               5                   10                  15

Pro Gly Pro

<210> SEQ ID NO 20
<211> LENGTH: 20
<212> TYPE: PRT
<213> ORGANISM: Artificial Sequence
<220> FEATURE:
<223> OTHER INFORMATION: E2A

<400> SEQUENCE: 20

Gln Cys Thr Asn Tyr Ala Leu Leu Lys Leu Ala Gly Asp Val Glu Ser
1               5                   10                  15

Asn Pro Gly Pro
            20

<210> SEQ ID NO 21
<211> LENGTH: 22
<212> TYPE: PRT
<213> ORGANISM: Artificial Sequence
<220> FEATURE:
<223> OTHER INFORMATION: F2A

<400> SEQUENCE: 21

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 22
<211> LENGTH: 10
```

```
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (5)...(9)
<223> OTHER INFORMATION: SGGGG is repeated 5 times

<400> SEQUENCE: 22

Pro Gly Gly Gly Ser Gly Gly Gly Gly Pro
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Linker

<400> SEQUENCE: 23

Gly Ser Ala Asp Asp Ala Lys Lys Asp Ala Ala Lys Lys Asp Gly Lys
1               5                   10                  15

Ser

<210> SEQ ID NO 24
<211> LENGTH: 66
<212> TYPE: DNA
<213> ORGANISM: Artificial Sequence
<220> FEATURE:
<223> OTHER INFORMATION: GMCSFR alpha chain signal sequence

<400> SEQUENCE: 24
atgcttctcc tggtgacaag ccttctgctc tgtgagttac cacacccagc attcctcctg     60
atccca                                                                66

<210> SEQ ID NO 25
<211> LENGTH: 22
<212> TYPE: PRT
<213> ORGANISM: Artificial Sequence
<220> FEATURE:
<223> OTHER INFORMATION: GMCSFR alpha chain signal sequence

<400> SEQUENCE: 25

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 26
<211> LENGTH: 18
<212> TYPE: PRT
<213> ORGANISM: Artificial Sequence
<220> FEATURE:
<223> OTHER INFORMATION: CD8 alpha signal peptide

<400> SEQUENCE: 26

Met Ala Leu Pro Val Thr Ala Leu Leu Leu Pro Leu Ala Leu Leu Leu
1               5                   10                  15

His Ala

<210> SEQ ID NO 27
<211> LENGTH: 15
<212> TYPE: PRT
<213> ORGANISM: Artificial Sequence
```

```
<220> FEATURE:
<223> OTHER INFORMATION: Hinge

<400> SEQUENCE: 27

Glu Pro Lys Ser Cys Asp Lys Thr His Thr Cys Pro Pro Cys Pro
1               5                   10                  15

<210> SEQ ID NO 28
<211> LENGTH: 12
<212> TYPE: PRT
<213> ORGANISM: Artificial Sequence
<220> FEATURE:
<223> OTHER INFORMATION: Hinge

<400> SEQUENCE: 28

Glu Arg Lys Cys Cys Val Glu Cys Pro Pro Cys Pro
1               5                   10

<210> SEQ ID NO 29
<211> LENGTH: 61
<212> TYPE: PRT
<213> ORGANISM: Artificial Sequence
<220> FEATURE:
<223> OTHER INFORMATION: Hinge

<400> SEQUENCE: 29

Glu Leu Lys Thr Pro Leu Gly Asp Thr His Thr Cys Pro Arg Cys Pro
1               5                   10                  15

Glu Pro Lys Ser Cys Asp Thr Pro Pro Cys Pro Arg Cys Pro Glu
            20                  25                  30

Pro Lys Ser Cys Asp Thr Pro Pro Cys Pro Arg Cys Pro Glu Pro
        35                  40                  45

Lys Ser Cys Asp Thr Pro Pro Cys Pro Arg Cys Pro
    50                  55                  60

<210> SEQ ID NO 30
<211> LENGTH: 12
<212> TYPE: PRT
<213> ORGANISM: Artificial Sequence
<220> FEATURE:
<223> OTHER INFORMATION: Hinge

<400> SEQUENCE: 30

Glu Ser Lys Tyr Gly Pro Pro Cys Pro Ser Cys Pro
1               5                   10

<210> SEQ ID NO 31
<211> LENGTH: 5
<212> TYPE: PRT
<213> ORGANISM: Artificial Sequence
<220> FEATURE:
<223> OTHER INFORMATION: Hinge
<220> FEATURE:
<221> NAME/KEY: VARIANT
<222> LOCATION: 1
<223> OTHER INFORMATION: Xaa1 = glycine, cysteine or arginine
<220> FEATURE:
<221> NAME/KEY: VARIANT
<222> LOCATION: 4
<223> OTHER INFORMATION: Xaa4 = cysteine or threonine

<400> SEQUENCE: 31

Xaa Pro Pro Xaa Pro
1               5

<210> SEQ ID NO 32
```

```
<211> LENGTH: 9
<212> TYPE: PRT
<213> ORGANISM: Artificial Sequence
<220> FEATURE:
<223> OTHER INFORMATION: Hinge

<400> SEQUENCE: 32

Tyr Gly Pro Pro Cys Pro Pro Cys Pro
1               5

<210> SEQ ID NO 33
<211> LENGTH: 10
<212> TYPE: PRT
<213> ORGANISM: Artificial Sequence
<220> FEATURE:
<223> OTHER INFORMATION: Hinge

<400> SEQUENCE: 33

Lys Tyr Gly Pro Pro Cys Pro Pro Cys Pro
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Hinge

<400> SEQUENCE: 34

Glu Val Val Val Lys Tyr Gly Pro Pro Cys Pro Pro Cys Pro
1               5                   10

<210> SEQ ID NO 35
<211> LENGTH: 11
<212> TYPE: PRT
<213> ORGANISM: Artificial Sequence
<220> FEATURE:
<223> OTHER INFORMATION: FMC63 CDR L1

<400> SEQUENCE: 35

Arg Ala Ser Gln Asp Ile Ser Lys Tyr Leu Asn
1               5                   10

<210> SEQ ID NO 36
<211> LENGTH: 7
<212> TYPE: PRT
<213> ORGANISM: Artificial Sequence
<220> FEATURE:
<223> OTHER INFORMATION: FMC63 CDR L2

<400> SEQUENCE: 36

Ser Arg Leu His Ser Gly Val
1               5

<210> SEQ ID NO 37
<211> LENGTH: 9
<212> TYPE: PRT
<213> ORGANISM: Artificial Sequence
<220> FEATURE:
<223> OTHER INFORMATION: FMC63 CDR L3

<400> SEQUENCE: 37

Gly Asn Thr Leu Pro Tyr Thr Phe Gly
1               5

<210> SEQ ID NO 38
<211> LENGTH: 5
```

```
<212> TYPE: PRT
<213> ORGANISM: Artificial Sequence
<220> FEATURE:
<223> OTHER INFORMATION: FMC63 CDR H1

<400> SEQUENCE: 38

Asp Tyr Gly Val Ser
1               5

<210> SEQ ID NO 39
<211> LENGTH: 16
<212> TYPE: PRT
<213> ORGANISM: Artificial Sequence
<220> FEATURE:
<223> OTHER INFORMATION: FMC63 CDR H2

<400> SEQUENCE: 39

Val Ile Trp Gly Ser Glu Thr Thr Tyr Tyr Asn Ser Ala Leu Lys Ser
1               5                   10                  15

<210> SEQ ID NO 40
<211> LENGTH: 7
<212> TYPE: PRT
<213> ORGANISM: Artificial Sequence
<220> FEATURE:
<223> OTHER INFORMATION: FMC63 CDR H3

<400> SEQUENCE: 40

Tyr Ala Met Asp Tyr Trp Gly
1               5

<210> SEQ ID NO 41
<211> LENGTH: 120
<212> TYPE: PRT
<213> ORGANISM: Artificial Sequence
<220> FEATURE:
<223> OTHER INFORMATION: FMC63 VH

<400> SEQUENCE: 41

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 42
<211> LENGTH: 107
<212> TYPE: PRT
<213> ORGANISM: Artificial Sequence
<220> FEATURE:
<223> OTHER INFORMATION: FMC63 VL

<400> SEQUENCE: 42
```

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65              70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 43
<211> LENGTH: 245
<212> TYPE: PRT
<213> ORGANISM: Artificial Sequence
<220> FEATURE:
<223> OTHER INFORMATION: FMC63 scFv

<400> SEQUENCE: 43

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65              70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
            165                 170                 175

Trp Gly Ser Glu Thr Thr Tyr Tyr Asn Ser Ala Leu Lys Ser Arg Leu
        180                 185                 190

Thr Ile Ile Lys Asp Asn Ser Lys Ser Gln Val Phe Leu Lys Met Asn
    195                 200                 205

Ser Leu Gln Thr Asp Asp Thr Ala Ile Tyr Tyr Cys Ala Lys His Tyr
210                 215                 220

Tyr Tyr Gly Gly Ser Tyr Ala Met Asp Tyr Trp Gly Gln Gly Thr Ser
225                 230                 235                 240

Val Thr Val Ser Ser
            245

```
<210> SEQ ID NO 44
<211> LENGTH: 11
<212> TYPE: PRT
<213> ORGANISM: Artificial Sequence
<220> FEATURE:
<223> OTHER INFORMATION: SJ25C1 CDR L1

<400> SEQUENCE: 44

Lys Ala Ser Gln Asn Val Gly Thr Asn Val Ala
1               5                   10

<210> SEQ ID NO 45
<211> LENGTH: 7
<212> TYPE: PRT
<213> ORGANISM: Artificial Sequence
<220> FEATURE:
<223> OTHER INFORMATION: SJ25C1 CDR L2

<400> SEQUENCE: 45

Ser Ala Thr Tyr Arg Asn Ser
1               5

<210> SEQ ID NO 46
<211> LENGTH: 9
<212> TYPE: PRT
<213> ORGANISM: Artificial Sequence
<220> FEATURE:
<223> OTHER INFORMATION: SJ25C1 CDR L3

<400> SEQUENCE: 46

Gln Gln Tyr Asn Arg Tyr Pro Tyr Thr
1               5

<210> SEQ ID NO 47
<211> LENGTH: 5
<212> TYPE: PRT
<213> ORGANISM: Artificial Sequence
<220> FEATURE:
<223> OTHER INFORMATION: SJ25C1 CDR H1

<400> SEQUENCE: 47

Ser Tyr Trp Met Asn
1               5

<210> SEQ ID NO 48
<211> LENGTH: 17
<212> TYPE: PRT
<213> ORGANISM: Artificial Sequence
<220> FEATURE:
<223> OTHER INFORMATION: SJ25C1 CDR H2

<400> SEQUENCE: 48

Gln Ile Tyr Pro Gly Asp Gly Asp Thr Asn Tyr Asn Gly Lys Phe Lys
1               5                   10                  15

Gly

<210> SEQ ID NO 49
<211> LENGTH: 13
<212> TYPE: PRT
<213> ORGANISM: Artificial Sequence
<220> FEATURE:
<223> OTHER INFORMATION: SJ25C1 CDR H3

<400> SEQUENCE: 49

Lys Thr Ile Ser Ser Val Val Asp Phe Tyr Phe Asp Tyr
```

-continued

```
1               5                   10
```

<210> SEQ ID NO 50
<211> LENGTH: 122
<212> TYPE: PRT
<213> ORGANISM: Artificial Sequence
<220> FEATURE:
<223> OTHER INFORMATION: SJ25C1 VH

<400> SEQUENCE: 50

```
Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Val Ser Ser
        115                 120
```

<210> SEQ ID NO 51
<211> LENGTH: 108
<212> TYPE: PRT
<213> ORGANISM: Artificial Sequence
<220> FEATURE:
<223> OTHER INFORMATION: SJ25C1 VL

<400> SEQUENCE: 51

```
Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Ala Thr Tyr Arg Asn Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Lys Asp Leu Ala Asp Tyr Phe Cys Gln Gln Tyr Asn Arg Tyr Pro Tyr
                85                  90                  95

Thr Ser Gly Gly Gly Thr Lys Leu Glu Ile Lys Arg
            100                 105
```

<210> SEQ ID NO 52
<211> LENGTH: 15
<212> TYPE: PRT
<213> ORGANISM: Artificial Sequence
<220> FEATURE:
<223> OTHER INFORMATION: Linker

<400> SEQUENCE: 52

```
Gly Gly Gly Gly Ser Gly Gly Gly Ser Gly Gly Gly Gly Ser
1               5                   10                  15
```

<210> SEQ ID NO 53
<211> LENGTH: 245
<212> TYPE: PRT
<213> ORGANISM: Artificial Sequence
<220> FEATURE:
<223> OTHER INFORMATION: SJ25C1 scFv

<400> SEQUENCE: 53

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Asp Ile Glu Leu Thr Gln Ser
    130                 135                 140

Pro Lys Phe Met Ser Thr Ser Val Gly Asp Arg Val Ser Val Thr Cys
145                 150                 155                 160

Lys Ala Ser Gln Asn Val Gly Thr Asn Val Ala Trp Tyr Gln Gln Lys
                165                 170                 175

Pro Gly Gln Ser Pro Lys Pro Leu Ile Tyr Ser Ala Thr Tyr Arg Asn
            180                 185                 190

Ser Gly Val Pro Asp Arg Phe Thr Gly Ser Gly Ser Gly Thr Asp Phe
        195                 200                 205

Thr Leu Thr Ile Thr Asn Val Gln Ser Lys Asp Leu Ala Asp Tyr Phe
    210                 215                 220

Cys Gln Gln Tyr Asn Arg Tyr Pro Tyr Thr Ser Gly Gly Gly Thr Lys
225                 230                 235                 240

Leu Glu Ile Lys Arg
                245

<210> SEQ ID NO 54
<211> LENGTH: 12
<212> TYPE: PRT
<213> ORGANISM: Artificial Sequence
<220> FEATURE:
<223> OTHER INFORMATION: FMC63 HC-CDR3

<400> SEQUENCE: 54

His Tyr Tyr Tyr Gly Gly Ser Tyr Ala Met Asp Tyr
1               5                   10

<210> SEQ ID NO 55
<211> LENGTH: 7
<212> TYPE: PRT
<213> ORGANISM: Artificial Sequence
<220> FEATURE:
<223> OTHER INFORMATION: FMC63 LC-CDR2

<400> SEQUENCE: 55

His Thr Ser Arg Leu His Ser
1               5

<210> SEQ ID NO 56
<211> LENGTH: 9
<212> TYPE: PRT
<213> ORGANISM: Artificial Sequence
<220> FEATURE:
<223> OTHER INFORMATION: FMC63 LC-CDR3

<400> SEQUENCE: 56

Gln Gln Gly Asn Thr Leu Pro Tyr Thr
1               5

<210> SEQ ID NO 57
<211> LENGTH: 735
<212> TYPE: DNA
<213> ORGANISM: Artificial Sequence
<220> FEATURE:
<223> OTHER INFORMATION: Sequence encoding scFv

<400> SEQUENCE: 57

```
gacatccaga tgacccagac cacctccagc ctgagcgcca gcctgggcga ccgggtgacc      60
atcagctgcc gggccagcca ggacatcagc aagtacctga actggtatca gcagaagccc     120
gacggcaccg tcaagctgct gatctaccac accagccggc tgcacagcgg cgtgcccagc     180
cggtttagcg gcagcggctc cggcaccgac tacagcctga ccatctccaa cctggaacag     240
gaagatatcg ccacctactt tgccagcag ggcaacacac tgccctacac ctttggcggc      300
ggaacaaagc tggaaatcac cggcagcacc tccggcagcg gcaagcctgg cagcggcgag     360
ggcagcacca agggcgaggt gaagctgcag gaaagcggcc ctggcctggt ggcccccagc     420
cagagcctga gcgtgacctg caccgtgagc ggcgtgagcc tgcccgacta cggcgtgagc     480
tggatccggc agccccccag gaagggcctg gaatggctgg gcgtgatctg gggcagcgag     540
accacctact acaacagcgc cctgaagagc cggctgacca tcatcaagga caacagcaag     600
agccaggtgt tcctgaagat gaacagcctg cagaccgacg acaccgccat ctactactgc     660
gccaagcact actactacgg cggcagctac gccatggact actggggcca gggcaccagc     720
gtgaccgtga gcagc                                                      735
```

<210> SEQ ID NO 58
<211> LENGTH: 18
<212> TYPE: PRT
<213> ORGANISM: Artificial Sequence
<220> FEATURE:
<223> OTHER INFORMATION: Linker

<400> SEQUENCE: 58

Gly Ser Thr Ser Gly Ser Gly Lys Pro Gly Ser Gly Glu Gly Ser Thr
1               5                   10                  15

Lys Gly

<210> SEQ ID NO 59
<211> LENGTH: 326
<212> TYPE: PRT
<213> ORGANISM: Homo sapiens
<220> FEATURE:
<223> OTHER INFORMATION: Human IgG2 Fc
<300> PUBLICATION INFORMATION:
<308> DATABASE ACCESSION NUMBER: Uniprot P01859

<309> DATABASE ENTRY DATE: 1986-07-21

<400> SEQUENCE: 59

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 60
<211> LENGTH: 327
<212> TYPE: PRT
<213> ORGANISM: Homo sapiens
<220> FEATURE:
<223> OTHER INFORMATION: Human IgG4 Fc
<300> PUBLICATION INFORMATION:
<308> DATABASE ACCESSION NUMBER: Uniprot P01861
<309> DATABASE ENTRY DATE: 1986-07-21

<400> SEQUENCE: 60

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 61
<211> LENGTH: 354
<212> TYPE: PRT
<213> ORGANISM: Flavobacterium meningosepticum
<220> FEATURE:
<223> OTHER INFORMATION: PNGase F

<400> SEQUENCE: 61

Met Arg Lys Leu Leu Ile Phe Ser Ile Ser Ala Tyr Leu Met Ala Gly
1               5                   10                  15

Ile Val Ser Cys Lys Gly Val Asp Ser Ala Thr Pro Val Thr Glu Asp
            20                  25                  30
```

```
Arg Leu Ala Leu Asn Ala Val Asn Ala Pro Ala Asp Asn Thr Val Asn
        35              40              45

Ile Lys Thr Phe Asp Lys Val Lys Asn Ala Phe Gly Asp Gly Leu Ser
    50              55              60

Gln Ser Ala Glu Gly Thr Phe Thr Phe Pro Ala Asp Val Thr Thr Val
65              70              75              80

Lys Thr Ile Lys Met Phe Ile Lys Asn Glu Cys Pro Asn Lys Thr Cys
                85              90              95

Asp Glu Trp Asp Arg Tyr Ala Asn Val Tyr Val Lys Asn Lys Thr Thr
            100             105             110

Gly Glu Trp Tyr Glu Ile Gly Arg Phe Ile Thr Pro Tyr Trp Val Gly
                115             120             125

Thr Glu Lys Leu Pro Arg Gly Leu Glu Ile Asp Val Thr Asp Phe Lys
        130             135             140

Ser Leu Leu Ser Gly Asn Thr Glu Leu Lys Ile Tyr Thr Glu Thr Trp
145             150             155             160

Leu Ala Lys Gly Arg Glu Tyr Ser Val Asp Phe Asp Ile Val Tyr Gly
            165             170             175

Thr Pro Asp Tyr Lys Tyr Ser Ala Val Val Pro Val Ile Gln Tyr Asn
            180             185             190

Lys Ser Ser Ile Asp Gly Val Pro Tyr Gly Lys Ala His Thr Leu Gly
            195             200             205

Leu Lys Lys Asn Ile Gln Leu Pro Thr Asn Thr Glu Lys Ala Tyr Leu
        210             215             220

Arg Thr Thr Ile Ser Gly Trp Gly His Ala Lys Pro Tyr Asp Ala Gly
225             230             235             240

Ser Arg Gly Cys Ala Glu Trp Cys Phe Arg Thr His Thr Ile Ala Ile
            245             250             255

Asn Asn Ala Asn Thr Phe Gln His Gln Leu Gly Ala Leu Gly Cys Ser
            260             265             270

Ala Asn Pro Ile Asn Asn Gln Ser Pro Gly Asn Trp Ala Pro Asp Arg
        275             280             285

Ala Gly Trp Cys Pro Gly Met Ala Val Pro Thr Arg Ile Asp Val Leu
        290             295             300

Asn Asn Ser Leu Thr Gly Ser Thr Phe Ser Tyr Glu Tyr Lys Phe Gln
305             310             315             320

Ser Trp Thr Asn Asn Gly Thr Asn Gly Asp Ala Phe Tyr Ala Ile Ser
            325             330             335

Ser Phe Val Ile Ala Lys Ser Asn Thr Pro Ile Ser Ala Pro Val Val
            340             345             350

Thr Asn
```

METHODS FOR MASS SPECTROMETRY ANALYSIS OF ENGINEERED CELL COMPOSITIONS

CROSS-REFERENCE TO RELATED APPLICATIONS

This application is a National Stage application under 35 U.S.C. § 371 of International Application No. PCT/US2019/050681, filed on Sep. 11, 2019, which claims priority from U.S. provisional application No. 62/729,985 filed Sep. 11, 2018, entitled "Methods for Mass Spectrometry Analysis of Engineered Cell Compositions," the contents of which are incorporated by reference in their entirety.

INCORPORATION BY REFERENCE OF SEQUENCE LISTING

The present application is being filed with a Sequence Listing in electronic format. The Sequence Listing is provided as a file entitled 735042019000SeqList.txt, created on Mar. 8, 2021, which is 43,905 bytes in size. The information in electronic format of the Sequence Listing is incorporated by reference in its entirety.

FIELD

Provided herein are methods for generating a mass spectrometry (MS) profile of a sample from a cell composition, such as an engineered cell composition. In some embodiments, the mass spectrometry profile includes data based on one or more mass spectrometry analyses or techniques. Also provided herein are methods for, based on mass spectrometry profiles of one or more samples of such cell compositions: identifying a mass spectrometry (MS) profile of a genetically engineered cell composition comprising immune cells comprising a recombinant receptor by comparison to a reference mass spectrometry profile; characterizing a process for producing genetically engineered cell composition; assessing cell surface proteins of an engineered cell composition; and assessing a process for producing a genetically engineered cell composition.

BACKGROUND

Autologous T cell therapies such a chimeric antigen receptors (CAR) T cell therapies have shown great promise for treating subjects with diseases, including cancers such as relapsed and refractory B-cell neoplasms, such as acute lymphoblastic leukemia, chronic lymphocytic leukemia, and non-Hodgkin lymphomas. While such therapies have great potential to benefit diseased subjects, Autologous T cell therapies are generally more complex than alternative therapies owing in part to the fact that the drug product includes living cells obtained from subjects having different genetic backgrounds and different variations or degrees of a disease and that the cells must be processed or genetically engineered to arrive at a final drug product. Given such complexity, care must be taken to insure that the cell therapies are produced with a consistent quality across different subjects. What are needed in the art are additional methods for analyzing cell compositions and reagents used to generate cell therapies.

SUMMARY

Provided herein are methods for identifying a mass spectrometry (MS) profile of a genetically engineered cell composition, the method including: determining a test mass spectrometry profile of a sample from a test engineered cell composition or a subset thereof using a mass spectrometry technique, said test engineered cell composition containing immune cells containing a recombinant receptor; comparing the test mass spectrometry profile to a reference mass spectrometry profile; and identifying one or more differences in the presence, absence or level of a least one data component in the test mass spectrometry profile compared to the reference mass spectrometry profile, thereby identifying a mass spectrometry profile of the cell composition containing the recombinant receptor.

Also provided herein are methods for identifying a mass spectrometry (MS) profile of a genetically engineered cell composition, the methods including: determining a test mass spectrometry profile of a sample from a test engineered cell composition or a subset thereof using a mass spectrometry technique, said test engineered cell composition comprising immune cells comprising a nucleic acid molecule encoding a recombinant receptor; comparing the test mass spectrometry profile to a reference mass spectrometry profile; and identifying one or more differences in the presence, absence or level of at least one data component in the test mass spectrometry profile compared to the reference mass spectrometry profile, thereby identifying a mass spectrometry profile unique to the sample.

Also provided herein are methods for identifying a mass spectrometry (MS) profile of a genetically engineered cell composition, the method comprising: determining a test mass spectrometry profile of a sample from a test engineered cell composition or a subset thereof using a mass spectrometry technique, said test engineered cell composition comprising immune cells comprising a recombinant receptor; and identifying one or more differences in the presence, absence or level of at least one data component in the test mass spectrometry profile compared to the reference mass spectrometry profile, thereby identifying a mass spectrometry profile of the cell composition comprising the recombinant receptor unique to the sample.

In some embodiments, the reference mass spectrometry profile is of a sample from a reference composition or is an average mass spectra profile of a number of samples from a plurality of reference compositions.

In some embodiments, the reference mass spectrometry profile is based on a sample from a reference composition. In some embodiments, the reference mass spectrometry profile is based on a plurality of samples from a reference composition. In some embodiments, the reference mass spectrometry profile is based on a number of samples from a plurality of reference compositions.

In some embodiments, the test engineered cell composition is for use in an autologous cell therapy. In some embodiments, the test engineered cell composition is produced by a process including: selecting or isolating immune cells from a sample from a subject, thereby generating a source composition, optionally wherein the biological sample is a leukapheresis sample, apheresis sample or a whole blood sample; incubating the cells of the source composition with a stimulatory reagent, thereby generating a stimulated composition, wherein the incubating is optionally carried out in the presence of one or more cytokines; introducing a nucleic acid encoding the recombinant receptor into immune cells of the stimulated composition, thereby generating a transformed composition; and culturing the stimulated composition at 37° C. for at least 24 hours, thereby generating the test engineered cell composition, wherein the culturing is optionally carried out in the presence of one or more cytokines.

In some embodiments, the reference composition or each of the plurality of reference cell compositions has not been introduced with a nucleic acid molecule encoding the recombinant receptor.

In some embodiments, the reference mass spectrometry profile is of a sample from a reference composition and the reference cell composition is a source cell composition containing the immune cells from which the test cell composition has been derived or obtained. In some embodiments, the reference mass spectrometry profile is of a sample from a reference composition, wherein: the test engineered cell composition contains immune cells obtained from a subject, said immune cells containing a nucleic acid molecule encoding the recombinant receptor; and the reference cell composition is an input composition containing the immune cells obtained from the subject that do not contain the nucleic acid encoding the recombinant receptor.

In some embodiments, the reference mass spectrometry profile is of a sample from a reference composition and the reference cell composition is a composition obtained after, prior to or during a stage of the manufacturing process for producing the test engineered cell composition.

In some embodiments, the reference mass spectrometry profile is of a sample from a reference composition, the test engineered cell composition is produced from one stage of a process, and the reference composition is obtained after, prior to or during the stage in which the test engineered cell composition is produced.

In some embodiments, the test engineered cell composition is a sample obtained from a subject previously administered the engineered cell composition. In some embodiments, the sample obtained from the subject contains immune cells engineered with the recombinant receptor, optionally as detected by flow cytometry or polymerase chain reaction (PCR). In some embodiments, the sample obtained from the subject is a blood sample or a tumor sample.

In some embodiments, the sample obtained from the subject is obtained between or between about 6 and 30 days, between or between about 14 and 29 days, or between or between about 17 and 22 days after administration of the engineered cells to the subject. In some embodiments, the sample is obtained from the subject at a time at or about or immediately after peak cells expressing the recombinant receptor are detectable in the blood of the subject.

In some embodiments, the test engineered cell composition contains cells that have been contacted by an agent to produce a recombinant receptor-dependent activity, optionally wherein the agent is a target antigen that is capable of being bound by the recombinant receptor or is an anti-idiotypic antibody specific to the antibody.

In some embodiments, the reference mass spectrometry profile is an average mass spectra profile of a number of samples from a plurality of reference compositions. In some embodiments, each of the plurality of reference compositions contains cells containing the recombinant receptor. In some embodiments, each of the plurality of reference compositions was produced by the same process or substantially the same process as the engineered cell composition.

Provided herein are methods for assessing a process for producing a genetically engineered cell composition, the methods including calculating the amount of variability in the presence, absence or level of at least one data component across a number of mass spectrometry profiles based on samples from a plurality of reference engineered cell compositions or a subset thereof, wherein each of the plurality of reference engineered cell compositions comprise a recombinant receptor produced by the same process or substantially the same process.

Provided herein are methods for assessing a process for producing a genetically engineered cell composition, the methods including: obtaining an average mass spectrometry profile of a sample of a plurality of reference engineered cell compositions or a subset thereof, wherein each of the plurality of the reference compositions contain a recombinant receptor produced by the same process or substantially the same process; and determining the presence, absence or level of variability or variance of the average mass spectrometry profile. In some embodiments, the method further includes selecting the process for producing an engineered cell composition if the variability or variance of the mass spectrometry profile among the plurality of the reference compositions is no more than 40%, no more than 30%, no more than 20%, no more than 10% or no more than 5%, or varies by such average by no more than one standard deviation among data components.

Provided herein are methods for assessing a process for producing a genetically engineered cell composition, the methods including: obtaining an average mass spectrometry profile of a number of mass spectrometry profiles based on samples from a plurality of reference engineered cell compositions or a subset thereof, wherein each of the plurality of the reference engineered cell compositions comprise a recombinant receptor produced by the same process or substantially the same process; and producing a reference mass spectrometry profile based on the number of mass spectrometry profiles; and determining the amount of variability in the presence, absence or level of at least one data component across the number variance of the average mass spectrometry profiles, thereby determining the degree of variance of cell compositions produced by the process.

In some embodiments, the methods test, using mass spectrometry profiles, if a process for producing genetically engineered cell compositions results in variability or variance across a plurality of engineered cell compositions. In some embodiments, the extent of such variability or variance is assessed using an average mass spectrometry profile based on samples from the plurality of engineered cell compositions.

In some embodiments, the method includes selecting a process for producing a genetically engineered cell composition if the amount of variability in the presence, absence, or level of the at least one data component across the number of mass spectrometry profiles is no more than 40%, no more than 30%, no more than 20%, no more than 10% or no more than 5% of the level of at least one data component in the reference mass spectrometry profile.

In some embodiments, the average mass spectroscopy profile is of a sample of (1) cells in the reference composition; (2) CD3+ cells in the composition; (3) CD4+ T cells in the composition; (4) CD8+ T cells in the composition; (5) recombinant receptor+ cells in the composition; (6) recombinant receptor+CD3+ cells in the composition; (7) recombinant receptor+CD8+ cells in the composition; or (8) recombinant receptor+CD4+ cells in the composition.

In some embodiments, each of the plurality of reference compositions is produced by a process including: selecting or isolating immune cells from a sample from a subject, thereby generating a source composition, optionally wherein the biological sample is a leukapheresis sample, apheresis sample or a whole blood sample; incubating the cells of the source composition with a stimulatory reagent, thereby generating a stimulated composition, wherein the incubating is optionally carried out in the presence of one or more cytokines; introducing a nucleic acid encoding the recombinant receptor into immune cells of the stimulated composition, thereby generating a transformed composition; and culturing the stimulated composition at 37° C. for at least 24 hours, thereby generating the test engineered cell composition, wherein the culturing is optionally carried out in the presence of one or more cytokines.

In some embodiments, the test mass spectrometry profile and reference mass spectrometry profile individually is a peptide profile. In some embodiments, the reference mass spectrometry profile is determined using the same mass spectrometry technique as the test mass spectrometry profile.

Provided herein are methods for characterizing a process for producing genetically engineered cell composition, the methods including: determining a first mass spectrometry profile of a sample from a first cell composition using a mass spectrometry technique; determining a second mass spectrometry profile of a sample from a second cell composition using a mass spectrometry technique; and identifying one or more differences in the presence, absence or level of a least one data component in the first mass spectrometry profile compared to the second mass spectrometry profile, wherein the first cell composition and second cell composition contain compositions at different stages of a manufacturing process for producing genetically engineered cell composition. In some embodiments, the first and second cell compositions are at different stages of generating a genetically engineered cell composition and are selected from: a source composition containing immune cells selected or isolated from a biological sample from a subject, optionally wherein the biological sample is a leukapheresis sample, apheresis sample or a whole blood sample; a stimulated composition containing immune cells of the selected composition that have been contacted with a stimulatory reagent, optionally wherein the contacting was carried out in the presence of one or more cytokines; a transformed composition containing cells of the stimulated composition containing a nucleic acid encoding the recombinant receptor; and a cultured composition containing cells of the transformed composition that have been cultured at or about 37° C. for at least 24 hours, optionally wherein the culturing is carried out in the presence of one or more cytokines.

In some embodiments, the first cell composition is a composition from a prior stage or prior timepoint of the manufacturing process compared to the second cell composition.

Provided herein are methods for characterizing a process for producing genetically engineered cell composition, the methods including: determining a first mass spectrometry profile of a sample from a first cell composition using a mass spectrometry technique; determining a second mass spectrometry profile of a sample from a second cell composition using a mass spectrometry technique; and identifying one or more differences in the presence, absence or level of at least one data component in the first mass spectrometry profile compared to the second mass spectrometry profile, wherein the first cell composition and second cell composition contain genetically engineered cells produced by different processes. In some embodiments, the different processes differ in one or more of the presence or concentration of serum; time in culture; lot of reagent; handling or storage of a reagent; presence or amount of a stimulatory reagent; the type of a stimulatory reagent; presence or amount of one or more cytokines; presence or amount of amino acids; temperature; the source or immune cell types of a source composition; the ratio or percentage of immune cell types in a source composition, optionally the CD4+/CD8+ cell ratio; cell density; static culture; rocking culture; perfusion; the type of viral vector; the vector copy number; the presence of a transduction adjuvant; cell density of a source composition in cryopreservation; the extent of expression of the recombinant receptor; or the presence of a compound to modulate cell phenotype.

In some embodiments, the first mass spectrometry profile and the second mass spectrometry profile individually is a peptide profile. In some embodiments, the first mass spectrometry profile and the second mass spectrometry profile are determined using the same mass spectrometry technique.

Provided herein are methods of characterizing a recombinant receptor, the methods including obtaining, using a mass spectrometry technique, a mass spectrometry profile with at least one data component of a recombinant receptor isolated from a sample from an engineered cell composition or a subset thereof comprising immune cells expressing or comprising the recombinant receptor.

Provided herein are methods of characterizing a recombinant receptor, the method including obtaining a mass spectrometry profile of a recombinant receptor, using a mass spectrometry technique, of a sample from a test engineered cell composition containing immune cells expressing or containing the recombinant receptor, said mass spectrometry profile including at least one data component.

Provided herein are methods of characterizing a recombinant receptor, the methods including: obtaining a test mass spectrometry profile, using a mass spectrometry technique, of a sample from a test engineered cell composition or a subset thereof comprising immune cells expressing or comprising a recombinant receptor; obtaining a reference mass spectrometry profile, using a mass spectrometry technique, of a sample from a reference composition or a subset thereof comprising immune cells, said reference mass spectrometry profile comprising at least one data component; and identifying one or more differences in the presence, absence or level of at least one data component in the test mass spectrometry profile compared to the reference mass spectrometry profile.

In some embodiments, the method further includes identifying one or more differences in the at least one data component compared to a mass spectrometry profile of the same cells but not expressing the recombinant receptor.

In some embodiments, the test engineered cell composition and the reference cell composition are substantially similar except for the presence of the recombinant receptor, optionally wherein the test engineered cell composition and the reference composition are produced by a substantially similar process and/or comprise the same type of immune cells.

In some embodiments, the test engineered cell composition has been stimulated in the presence of a stimulatory reagent. In some embodiments, the engineered cell composition contains cells that have been contacted by an agent to produce a recombinant receptor-dependent activity, optionally wherein the agent is a target antigen that is capable of being bound by the recombinant receptor or is an anti-idiotypic antibody specific to the antibody.

In some embodiments, the method further includes identifying one or more differences in the mass spectrometry profile compared to a mass spectrometry of the same engineered cell composition but that has not been stimulated in the presence of a stimulatory reagent or has been stimulated in the presence of a different stimulatory reagent.

In some embodiments, the cell composition is enriched in the immune cells. In some embodiments, the immune cells include lymphocytes. In some embodiments, the lymphocytes include T cells or Natural Killer (NK) cells. In some embodiments, the lymphocytes include T cells and the T cells are CD4+ and/or CD8+ T cells. In some embodiments, the immune cells are human.

Among any of the provided embodiments, any of the cell compositions include a cell composition that is enriched in immune cells, such as by selecting, isolating or purifying immune cells from a biological sample, e.g. by immunoaffinity-based methods. In some embodiments, the test engineered cell composition is enriched in the immune cells. In some embodiments, the reference composition is enriched in the immune cells. In some embodiments, the reference engineered cell composition is enriched in the immune cells. In some embodiments, the source composition is enriched in the immune cells. In some embodiments, the stimulated composition is enriched in the immune cells. In some embodiments, the transformed composition is enriched in the immune cells. In some embodiments, the engineered cell composition is enriched in the immune cells. In some embodiments, the first cell composition is enriched in the immune cells. In some embodiments, the second cell composition is enriched in the immune cells. In some embodiments, the cultured composition is enriched in the immune cells. In some embodiments, each of the test engineered cell composition and the reference composition is enriched in the immune cells. In some embodiments, each of the test engineered cell composition and the reference engineered composition is enriched in the immune cells. In some embodiments, each of the first cell composition and the second cell composition is enriched in the immune cells.

In some embodiments, the immune cells are T cells, optionally CD4+ and/or CD8+ T cells, and the stimulatory reagent is capable of activating one or more intracellular signaling domains of one or more components of a TCR complex and/or one or more intracellular signaling domains of one or more costimulatory molecules. In some embodiments, the stimulatory reagent includes a primary agent that specifically binds to a member of a TCR complex and a secondary agent that specifically binds to a T cell costimulatory molecule. In some embodiments, the primary agent specifically binds to CD3 and/or the costimulatory molecule is selected from the group consisting of CD28, CD137 (4-1-BB), OX40, or ICOS. In some embodiments, the stimulatory reagent includes an anti-CD3 antibody or antigen binding fragment thereof and an anti-CD28 antibody or an antigen-binding fragment thereto.

In some embodiments, the primary and secondary agents are present on the surface of a solid support, optionally wherein the solid support is a bead. In some embodiments, the primary and secondary agents are present on the surface of a soluble oligomeric reagent including a streptavidin or a streptavidin mutein.

In some embodiments, the culturing is carried out under conditions to promote proliferation and/or expansion of the engineered cells.

In some embodiments, the sample is processed from the test engineered cell composition by labeling one or more surface proteins, lysing cells, and isolating the one or more proteins. In some embodiments, the method further includes digesting the one or more isolated proteins.

Provided herein are methods of assessing surface proteins of an engineered cell composition including (a) labeling one or more surface proteins present on cells of an engineered cell composition or a subset thereof, the engineered cell composition containing cells expressing or containing a recombinant receptor, thereby generating a labeled cell composition; (b) lysing cells of the labeled cell composition, thereby generating a lysed cell composition; (c) isolating the one or more surface proteins form the lysed cell composition to obtain one or more isolated proteins; and (d) subjecting the one or more isolated proteins to a mass spectrometry technique to obtain a mass spectrometry profile including one or more data components.

In some embodiments, prior to (d), the method further includes digesting the one or more isolated proteins. In some embodiments, the digestion is carried out by proteolysis in the presence of one or more protease that is capable of cleaving one or more peptide bonds. In some cases, the one or more protease is or contains trypsin.

In some embodiments, the one or more proteins contain cell surface membrane proteins. In some embodiments, the lysing the cells includes incubation in the presence of a detergent. In some embodiments, the detergent is a nonionic detergent. In some embodiments, the detergent is or contains an effective amount of Triton X-100. In some embodiments, the detergent is a denaturing detergent. In some examples, the denaturing detergent is or contains an effective amount of Sodium dodecyl sulfate (SDS). In some embodiments, after the lysing the cells, the method further includes removing the detergent from the lysed composition.

In some embodiments, the labeling the surface proteins includes biotin labeling of primary amines. In some examples, the one or more proteins are isolated using a reagent contains avidin, streptavidin, NeutrAvidin™ or CaptAvidin™.

In some embodiments, the mass spectrometry technique includes subjecting the sample to liquid chromatography (LC) followed by mass spectrometry. In some embodiments, the liquid chromatography is high performance liquid chromatography (HPLC), ultra-high performance liquid chromatography (UHPLC), or ultra performance liquid chromatography (UPLC). In some instances, the liquid chromatography is ultra performance liquid chromatography (UPLC).

In some embodiments, the liquid chromatography and mass spectrometry are carried out online. In some embodiments, the liquid chromatography is selected from normal phase (NP-), reverse phase (RP) and hydrophilic interaction chromatography (HILIC). In some embodiments, the mass spectrometer that performs the mass spectrometry includes one or more of a quadrupole, ion trap, time of flight (TOF), or Fourier transform ion cyclotron resonance mass analyzer. In some embodiments, the mass spectrometer includes an ion trap mass analyzer that is a three-dimensional quadrupole ion trap, a cylindrical ion trap, a linear quadrupole ion trap, or an Orbitrap mass analyzer. In some examples, the mass spectrometer is a quadrupole-Orbitrap mass spectrometer.

In some embodiments, the data components are selected from MS ion information, total ion chromatograph (TIC) or a portion thereof, extracted ion chromatogram (XIC) or a portion thereof, peptide MS ion signal peak, protein MS ion signal peak, peptide identification information, protein identification information, qualitative information, quantitative information, structural information, post-translation modifications. In some embodiments, the data component is an XIC or a portion thereof, wherein the XIC or portion thereof is based on one or more theoretical or known m/z values of one or more peptide components of the recombinant receptor. In some embodiments, the one or more peptide components is a proteolytically cleaved or digested peptide component, optionally wherein the protease is trypsin.

In some of any such embodiments, the recombinant receptor is or contains a chimeric receptor and/or a recombinant antigen receptor. In some embodiments, the recombinant receptor is capable of binding to a target antigen that is associated with, specific to, and/or expressed on a cell or tissue of a disease, disorder or condition. In some examples, the disease, disorder or condition is an infectious disease or disorder, an autoimmune disease, an inflammatory disease, or a tumor or a cancer. In some aspects, the target antigen is a tumor antigen. In some examples, the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Ra), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

In some of any such embodiments, the recombinant receptor is or contains a functional non-TCR antigen receptor or a TCR or antigen-binding fragment thereof. In some embodiments, the recombinant receptor is a chimeric antigen receptor (CAR).

In some embodiments, the sample is of the cell composition or a subset thereof selected from (1) cells in the cell composition, (2) CD3+ cells in the cell composition; (3) CD4+ T cells in the cell composition; (4) CD8+ T cells in the cell composition; (5) recombinant receptor+ cells in the cell composition; (6) recombinant receptor+CD3+ cells in the cell composition, (7) recombinant receptor+CD8+ cells in the cell composition, or (8) recombinant receptor+CD4+ cells in the cell composition, optionally wherein the recombinant receptor is a CAR.

Provided here are engineered cell compositions produced by a process in which the mass spectrometry profile of a sample from the engineered cell composition or a subset thereof varies by no more than 40%, no more than 30%, no more than 20%, no more than 10% or no more than 5% among the average mass spectrometry profile of a plurality of engineered cell compositions produced by the process, or varies by such average by no more than one standard deviation among data components of the mass spectrometry profile.

Provided here are engineered cell compositions produced by a process in which the level of at least one data component from a mass spectrometry profile, obtained using a mass spectroscopy technique, of a sample from an engineered cell composition or a subset thereof varies by no more than 40%, no more than 30%, no more than 20%, no more than 10% or no more than 5% from the level of at least one data component from a reference mass spectrometry profile based on a number of mass spectrometry profiles of samples from a plurality of engineered cell compositions produced by the process, or varies from such reference by no more than the standard deviation of the level of at least data component across the number of mass spectrometry profiles.

In some embodiments, the engineered cell composition includes a recombinant receptor. In some embodiments, the engineered cell composition includes immune cells.

In some embodiments, the process for producing the engineered cell composition includes (i) selecting or isolating immune cells from a sample from a subject, thereby generating a source composition, optionally wherein the biological sample is a leukapheresis sample, apheresis sample or a whole blood sample; (ii) incubating the cells of the source composition with a stimulatory reagent, thereby generating a stimulated composition, wherein the incubating is optionally carried out in the presence of one or more cytokines; (iii) introducing a nucleic acid encoding the recombinant receptor into immune cells of the stimulated composition, thereby generating a transformed composition; and (iv) culturing the stimulated composition at 37° C. for at least 24 hours, thereby generating the test engineered cell composition, wherein the culturing is optionally carried out in the presence of one or more cytokines.

In some embodiments, the cell composition is enriched in the immune cells. In some embodiments, the immune cells include lymphocytes. In some embodiments, the lymphocytes include T cells or Natural Killer (NK) cells. In some examples, the lymphocytes include T cells and the T cells are CD4+ and/or CD8+ T cells.

In some embodiments, the engineered cell composition is enriched in the immune cells. In some embodiments, the source composition is enriched in the immune cells. In some embodiments, the transformed composition is enriched in the immune cells.

In some embodiments, the immune cells are human.

In some embodiments, the immune cells are T cells, optionally CD4+ and/or CD8+ T cells, and the stimulatory reagent is capable of activating one or more intracellular signaling domains of one or more components of a TCR complex and/or one or more intracellular signaling domains of one or more costimulatory molecules. In some embodiments, the stimulatory reagent includes a primary agent that specifically binds to a member of a TCR complex and a secondary agent that specifically binds to a T cell costimulatory molecule. In some cases, the primary agent specifically binds to CD3 and/or the costimulatory molecule is selected from the group consisting of CD28, CD137 (4-1-BB), OX40, or ICOS.

In some embodiments, the stimulatory reagent includes an anti-CD3 antibody or antigen binding fragment thereof and an anti-CD28 antibody or an antigen-binding fragment thereto. In some embodiments, the primary and secondary agents are present on the surface of a solid support, optionally wherein the solid support is a bead. In some embodiments, the primary and secondary agents are present on the surface of a soluble oligomeric reagent including a streptavidin or a streptavidin mutein.

In some embodiments, the culturing is carried out under conditions to promote proliferation and/or expansion of the engineered cells. In some embodiments, the sample is processed from the engineered cell composition by labeling one or more surface proteins, lysing cells, and isolating the one or more proteins. In some embodiments, the method further includes digesting the one or more isolated proteins. In some embodiments, the digestion is carried out by proteolysis in the presence of one or more protease that is capable of cleaving one or more peptide bonds.

In some embodiments, the one or more protease is or contains trypsin. In some embodiments, the one or more proteins include cell surface membrane proteins. In some embodiments, the lysing the cells includes incubation in the presence of a detergent. In some examples, the detergent is a nonionic detergent.

In some embodiments, the detergent is or contains an effective amount of Triton X-100. In some cases, the detergent is a denaturing detergent. In some embodiments, the denaturing detergent is or contains an effective amount of Sodium dodecyl sulfate (SDS). In some embodiments, after the lysing the cells, the method further includes removing the detergent from the lysed composition.

In some embodiments, the labeling the surface proteins includes biotin labeling of primary amines.

In some embodiments, the one or more proteins are isolated using a reagent comprising avidin, streptavidin, NeutrAvidin™ or CaptAvidin™.

In some embodiments, the mass spectrometry technique includes subjecting the sample to liquid chromatography (LC) followed by mass spectrometry. In some examples, the liquid chromatography is high performance liquid chromatography (HPLC), ultra-high performance liquid chromatography (UHPLC), or ultra performance liquid chromatography (UPLC). In some embodiments, the liquid chromatography is ultra performance liquid chromatography (UPLC). In some cases, the liquid chromatography and mass spectrometry are carried out online. In some embodiments, the liquid chromatography is selected from normal phase (NP-), reverse phase (RP) and hydrophilic interaction chromatography (HILIC).

In some embodiments, the mass spectrometer that performs the mass spectrometry includes one or more of a quadrupole, ion trap, time of flight (TOF), or Fourier transform ion cyclotron resonance mass analyzer. In some embodiments, the mass spectrometer includes an ion trap mass analyzer that is a three-dimensional quadrupole ion trap, a cylindrical ion trap, a linear quadrupole ion trap, or an Orbitrap mass analyzer. In some embodiments, the mass spectrometer is a quadrupole-Orbitrap mass spectrometer.

In some embodiments, the data components are selected from MS ion information, total ion chromatograph (TIC) or a portion thereof, extracted ion chromatogram (XIC) or a portion thereof, peptide MS ion signal peak, protein MS ion signal peak, peptide identification information, protein identification information, qualitative information, quantitative information, structural information, post-translation modifications. In some embodiments, the data component is an XIC or a portion thereof, wherein the XIC or portion thereof is based on one or more theoretical or known m/z values of one or more peptide components of the recombinant receptor.

In some embodiments, the one or more peptide components is a proteolytically cleaved or digested peptide component, optionally wherein the protease is trypsin.

In some embodiments, the recombinant receptor is or includes a chimeric receptor and/or a recombinant antigen receptor. In some embodiments, the recombinant receptor is capable of binding to a target antigen that is associated with, specific to, and/or expressed on a cell or tissue of a disease, disorder or condition. In some cases, the disease, disorder or condition is an infectious disease or disorder, an autoimmune disease, an inflammatory disease, or a tumor or a cancer.

In some embodiments, the target antigen is a tumor antigen. In some examples, the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Ra), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

In some embodiments, the recombinant receptor is or includes a functional non-TCR antigen receptor or a TCR or antigen-binding fragment thereof. In some embodiments, the recombinant receptor is a chimeric antigen receptor (CAR).

Provided herein are methods of evaluating a reagent used in the process of producing an engineered cell composition including comparing a mass spectrometry profile of a sample from a first reagent to a reference mass spectrometry profile of the reagent, wherein the mass spectrometry profile is obtained using a mass spectrometry technique; and identifying one or more differences in the presence, absence or level of at least one data component in the test mass spectrometry profile compared to the reference mass spectrometry profile, thereby identifying a mass spectrometry profile of the reagent. In some embodiments, the reference mass spectrometry profile is of a sample from a reference reagent or is an average mass spectra profile of a number of samples from a plurality of different lots of the reagent. In some embodiments, the reference mass spectrometry profile is an average mass spectrometry profile of a sample of a plurality of different lots of the reagent.

In some embodiments, the method further includes determining the presence, absence or level of variability or variance of mass spectrometry profile of the sample to the average mass spectrometry profile. In some embodiments, the method further includes selecting a reagent if the variability or variance of the mass spectrometry profile among the plurality of the different lots of the reagent is no more than 40%, no more than 30%, no more than 20%, no more than 10% or no more than 5%, or varies by such average by no more than one standard deviation among data components of the mass spectrometry profile.

In some embodiments, the method further includes selecting the reagent if the amount of variability in the presence, absence, or level of at least one data component across the number of mass spectrometry profiles is no more than 40%, no more than 30%, no more than 20%, no more than 10%, or no more than 5% of the level of at least one data component in the reference mass spectrometry profile.

In some embodiments, the method further includes selecting the reagent if the level of at least one data component of the test mass spectrometry profile varies by no more than 40%, no more than 30%, no more than 20%, no more than 10% or no more than 5% from the level of at least one data component from the reference mass spectrometry profile, or varies from such level by no more than the standard deviation of the level of at least data component across the number of mass spectrometry profiles.

In some embodiments, the mass spectrometry technique comprises subjecting the sample to liquid chromatography (LC) followed by mass spectrometry. In some embodiments, the liquid chromatography is high performance liquid chromatography (HPLC), ultra-high performance liquid chromatography (UHPLC), or ultra performance liquid chromatography (UPLC). In some cases, the liquid chromatography is ultra performance liquid chromatography (UPLC).

In some embodiments, the liquid chromatography and mass spectrometry are carried out online. In some embodiments, the liquid chromatography is selected from normal phase (NP-), reverse phase (RP) and hydrophilic interaction chromatography (HILIC). In some embodiments, the mass spectrometer that performs the mass spectrometry comprises one or more of a quadrupole, ion trap, time of flight (TOF), or Fourier transform ion cyclotron resonance mass analyzer.

In some embodiments, the mass spectrometer comprises an ion trap mass analyzer that is a three-dimensional quadrupole ion trap, a cylindrical ion trap, a linear quadrupole ion trap, or an Orbitrap mass analyzer. In some embodiments, the mass spectrometer is a quadrupole-Orbitrap mass spectrometer.

In some embodiments, the data components are selected from MS ion information, total ion chromatograph (TIC) or a portion thereof, extracted ion chromatogram (XIC) or a portion thereof, peptide MS ion signal peak, protein MS ion signal peak, peptide identification information, protein identification information, qualitative information, quantitative information, structural information, post-translation modifications.

In some embodiments, the reagent is a reagent capable of stimulating a signal in cells of a cell composition, optionally a T cell composition. In some embodiments, the cells of the cell composition comprise a recombinant receptor, optionally a chimeric antigen receptor. In some embodiments, the reagent is capable of stimulating or inducing a recombinant receptor-dependent activity in cells of the cell composition.

BRIEF DESCRIPTION OF THE DRAWINGS

FIG. 1A depicts an exemplary total ion chromatogram (TIC) representing the peptide ions of cell surface proteins.

FIG. 1B depicts an exemplary extracted ion chromatogram (XIC) for peptide peaks associated with extracellular and intracellular portions of a CAR from the engineered and source T cell compositions.

FIG. 4A shows a HILIC-FLR chromatogram of PNGase F released N-glycans from the activated CD3+ T cell composition. FIG. 4B shows an extracted ion chromatogram (XIC) produced from the first stage of the tandem MS for the exemplary N-glycan, A3S3F (theoretical mass of 1113.0933), in the +3 charged state using a 5 ppm mass tolerance. FIG. 4C shows the MS/MS fragmentation of a further exemplary N-glycan, A3S4F (theoretical mass of 1210.4614), produced by the second stage of the tandem MS. Dashed boxes in FIG. 4C indicate different n-acetyl glucosamine residue linkages.

DETAILED DESCRIPTION

Figure 1A:
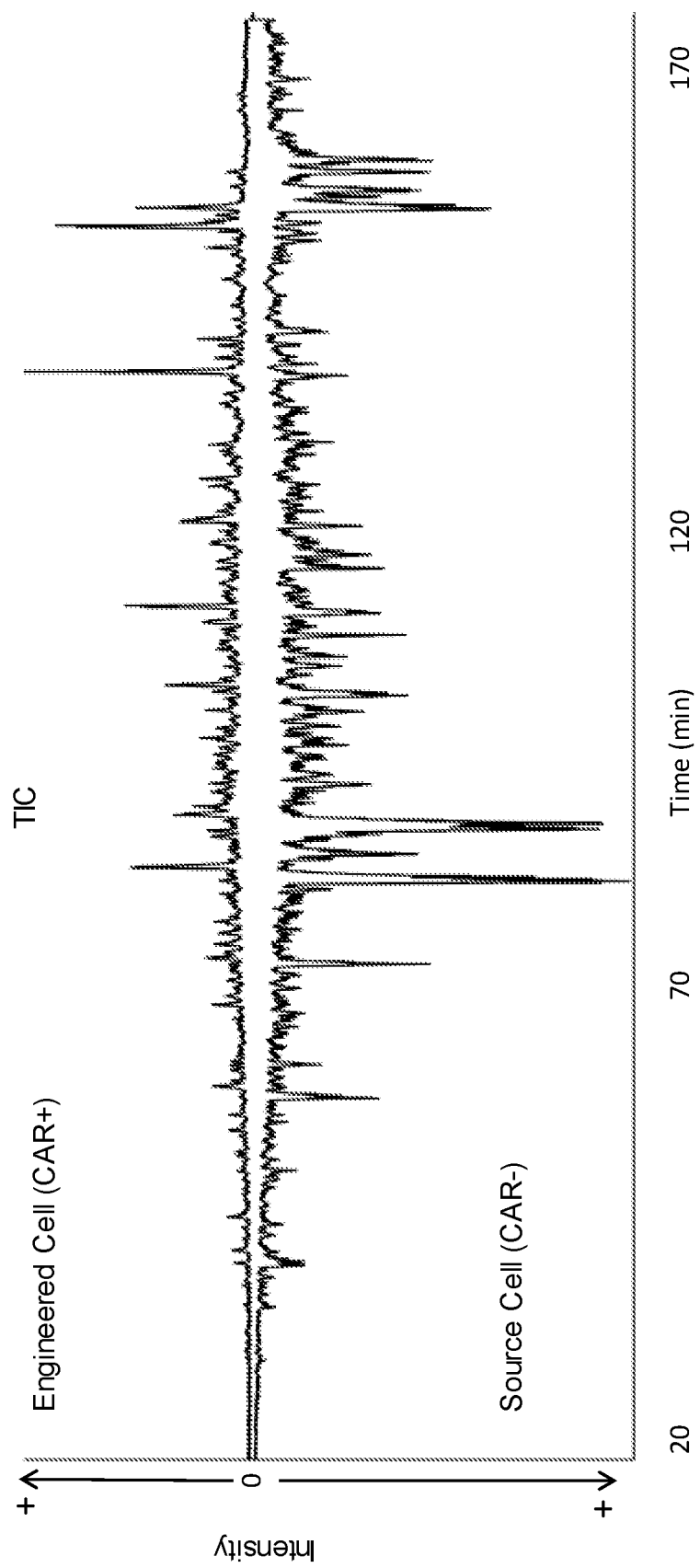
FIGS. 1A and 1B show exemplary readouts from mass spectrometry analysis of cell surface proteins isolated from identified source (CAR-) and engineered (CAR+) T cell compositions.

Provided herein are methods for identifying mass spectrometry profiles of cell compositions, including genetically engineered cell compositions, e.g., autologous CAR T cell compositions. In some aspects, the provided methods involve determining a mass spectrometry profile (e.g., a test mass spectrometry profile) of a sample from an engineered cell composition using a mass spectrometry technique. In some aspects, the engineered cell composition contains or includes cells comprising a recombinant receptor (e.g., a CAR). In particular aspects, the mass spectrometry profile is compared to a reference mass spectrometry profile, such as a reference mass spectrometry profile of or obtained from a sample from a composition used as a reference (e.g., a reference cell composition) determined using the same mass spectrometry technique, such as to identify one or more differences in the presence, absence, or level of at least one peptide species, including post-translational modifications thereof, in a test mass spectrometry profile as compared to a reference mass spectrometry profile.

Also provided herein are methods for characterizing a process, e.g., a manufacturing process, for producing genetically engineered cell composition. In certain embodiments, mass spectrometry profiles of cell compositions obtained at different stages of the process are analyzed to characterize the process, or, in some aspects, to characterize changes undergone by cells during the process. In some aspects, mass spectrometry profiles of engineered cell compositions generated from different processes, e.g., manufacturing processes for producing the engineered cells, are analyzed to characterize the processes, or, in some aspects, to characterize similarities or differences of cell compositions produced by the different processes.

In some aspects, provided are methods for assessing a process for producing a genetically engineered cell composition. In some aspects, the methods are or include obtaining an average mass spectrometry profile of a sample of a plurality of reference engineered cell compositions or a subset thereof and determining the presence, absence or level of variability or variance of the average mass spectrometry profile. In some embodiments, the plurality of the reference compositions contain cells expressing a recombinant receptor produced by the same process or substantially the same process.

In some aspects, provided are methods for assessing a process for producing a genetically engineered cell composition. In some aspects, the methods are or include obtaining a number of mass spectrometry profiles of samples from a plurality of reference engineered cell compositions or a subset thereof, producing an average mass spectrometry profile thereof, and determining the presence, absence, or level of at least one peptide species, including post-translational modifications thereof, in the average mass spectrometry profile. In some aspects, the methods further include determining the amount of variability or variance in the level of at least one peptide species, including post-translational modifications thereof, across the plurality of mass spectrometry profiles. In some aspects, the amount of variability or variance in the level of the at least one peptide species is compared to the average level of the at least one peptide species, thereby determining the extent of variability across the samples. In some embodiments, the plurality of the reference compositions contain cells expressing a recombinant receptor produced by the same process or substantially the same process.

In some aspects, provided are methods for assessing a process for producing a genetically engineered cell composition. In some aspects, the methods are or include obtaining a number of mass spectrometry profiles of samples from a plurality of reference engineered cell compositions or a subset thereof and determining the amount of variability or variance in the level of at least one peptide species, including post-translational modifications thereof, across the plurality of mass spectrometry profiles. In some embodiments, the plurality of the reference compositions contain cells expressing a recombinant receptor produced by the same process or substantially the same process.

Also provided are methods for characterizing a process for producing genetically engineered cells or cell compositions. In some aspects, the methods involve obtaining a first and a second mass spectrometry profile of samples from different cell compositions using a mass spectrometry technique and identifying one or more differences in the presence, absence, or level of a least one data component in the mass spectrometry profiles. In some embodiments, the cell compositions are or contain compositions at different stages of a manufacturing process for producing genetically engineered cell composition. In certain embodiments, the compositions contain genetically engineered cells produced by different processes.

In some aspects, the provided methods are useful for assessing or characterizing a recombinant receptor, such as by obtaining a mass spectrometry profile of a recombinant receptor using a mass spectrometry technique, of a sample. In some embodiments, the sample is from a test engineered cell composition or a subset thereof comprising immune cells expressing or comprising the recombinant receptor, said mass spectrometry profile comprising at least one data component.

Additional methods provided herein may be employed to analyze or assess surface proteins of an engineered cell composition. In some embodiments, such methods include steps for labeling one or more surface proteins present on cells of an engineered cell composition or a subset thereof, lysing cells of the labeled cell composition, isolating the surface proteins, and then subjecting the isolated proteins to a mass spectrometry technique. In some aspects, the methods produce a mass spectrometry profile containing data components, such as components related to one or more surface proteins, including some instances a recombinant receptor or CAR.

Particular embodiments contemplate that cell therapies, and in particular adoptive T-Cell therapies, represent a powerful technology for the treatment, alleviation, and/or amelioration of various diseases, such as cancer. Current analytical tools available for analyzing or characterizing therapeutic or pharmaceutical cell compositions include examination of cell surface or internal markers such as by flow cytometry or gene expression by techniques such as RNA-seq or ATAC-seq. While such techniques may be useful in some aspects for analyzing or characterizing cell compositions, these techniques are not without limitations. For example, in some aspects, detection of protein expression, such as by flow cytometry based methods, may be limited by the amount of different individual markers that can be examined in a single experiment. In some aspects, such assays must focus on targets that are predicted or hypothesized to change under certain conditions due to the limited amount of targets that can be assessed. Conversely, gene expression analysis by RNA-seq or ATAC-seq are suited for genome wide screening, allowing for unbiased detection of targets that may be affected by certain conditions. However, a limitation of these techniques are that changes at the level of gene expression do not always correlate to changes at the level of functional protein expression.

In particular embodiments, provided herein are unbiased methods useful for detecting, identifying, and/or quantifying proteins, such as cell surface proteins, present in a cell composition. In particular aspects, an advantage of the provided methods is that the methods can be employed to detect changes in protein, e.g., surface protein, under different conditions without a need for choosing or predicting specific targets prior to the analysis. In some aspects, an additional advantage of the provided methods is that the methods allow for the analysis of proteins, such as functional surface proteins, on a wide scale. Thus, in some aspects, the provided methods are suitable to be used either alone or in combination with existing methods to analyze or characterize cell compositions, such as cell therapy compositions.

In some aspects, cell therapies such as CAR T cell therapies are living cells that are derived from subjects and engineered to produce a final drug product. Thus, as opposed to small molecules or traditional biologics, it may, in some cases, be difficult to consistently engineer cell therapy compositions that are suitable for administration to a subject. For example, in some aspects, cells originating from different individual patients suffering from a particular disease may vary in certain attributes, such as cell health, viability, activity, and proliferative capability. Such differences may be due to different degrees or variations of the disease across patients, or in some aspects, may be due to different genetic or environmental backgrounds of the patients. In some aspects, any differences between cell compositions obtained from the subjects may be exacerbated by different reactions to the engineering process. In some aspects, the provided methods may be employed to assess the variability or variance of a cell therapy generated across multiple subjects, or to insure that an individual cell composition is within an acceptable tolerance as compared to an ideal or reference standard prior to administering the cell therapy.

In some aspects, the provided methods utilize mass spectrometry to characterize some or all of the cell surface proteins present in the cells of a cell composition, thereby allowing for different features of the cells to be assessed all at once. In some aspects, the provided methods identify and measure the level or amount of the individual surface proteins present on the cells. This technique is useful, inter alia, for monitoring changes that occur among individual cell compositions during an engineering process, or to verify the identity and quality of a cell therapy prior to administering the cell therapy to a patient. In certain aspects, an advantage of the provided methods is that the methods may detect changes that would be missed by techniques that are limited to an analysis of only several target proteins at a time, such as techniques that rely on antibody labeling to detect proteins.

In particular aspects, a single marker or surface protein may not be sufficient to detect the degree to which a T cell may possess a particular property. An advantage of the provided methods are that changes in multiple markers associated with a property may be assessed at the same time, thus allowing for changes along a continuum along several different properties to be detected within a single assessment.

The provided methods herein demonstrate that mass spectrometry profiles can be successfully generated from cell compositions, such as cell therapy compositions. In some aspects, the mass spectrometry profiles allow for further investigations of data components associated with one or more proteins or peptides of an engineered cell composition, including post translation modifications thereof, to characterize cell therapies and the impact different engineering processes may have on cells.

A particular advantage of the provided methods includes the high degree of resolution achieved for detecting and measuring a multitude of protein targets in a sample. In some aspects, this high degree of sensitivity allows for detection and quantitation of post translational modifications, such as glycan conjugation to the proteins. In some aspects, measurements or quantification of post transcriptional modifications may be compared to other readouts from the samples, such as genomic readouts produced by RNA-seq or Assay for Transposase-Accessible Chromatin using sequencing (ATAC-seq). Such comparisons are useful, inter alia, for identifying or evaluating how changes in enzymes at the genomic level may influence specific post translational modifications, and may, in some instances, be useful to develop further assays to evaluate properties or functionality in the cells. For example, in some aspects, the provided methods may be used to detect glycosylation of cell surface proteins, and such data may be correlated to expression of individual glycotransferases genes. In some aspects, such a correlation could be useful to identify or determine how changes at the genetic level influence function of the cell.

In certain aspects, the provided methods incorporate mass spectrometry to achieve a powerful tool for analyzing complex mixtures. In some aspects, it has been observed that in some cases, changes of storage or handling conditions of raw material(s) or reagent(s) or different lots of raw material(s) or reagent(s) used in a process for producing an engineered T cell composition—in an otherwise similar cell engineering process—may correlate, in the final engineered composition, with certain parameters associated with altered or varied activity of the engineered T cell product. (published PCT Appl. No. WO2018/157171). For example, in some aspects, the development, production, or engineering of cell therapies may require complex reagents, such as reagents that are or include one or more proteins. In some aspects, reagents that meet all of a vendor's release criteria may display lot to lot variation and therefore, in some aspects, may require additional screening to insure that the reagents do not contribute to unwanted variability or variance of the cell therapy. The provided methods provide additional means to investigate such complex mixtures to identify potential changes in cell therapies or reagents to insure that the cell therapies or reagents are suitable and safe for use.

In some aspects, the provided methods may leverage mass spectrometry-based assays, e.g., LC-MS, to identify differences (or lack thereof) between raw material lots of reagents, e.g., reagents used for genetically engineering cell compositions, at the protein level. In some aspects, mass spectrometry-based assays may be sensitive enough to detect differences between manufacturing lots, including differences that may not affect interactions between the reagent and cells. However, in some aspects, the provided methods allow for a focus on a subset of biologically relevant differences. Thus, in some aspects, while the provided methods produce an unbiased analysis of a cell composition or a reagent, the resulting data sets, e.g., mass spectrometry profiles, can be used to evaluate a subset of protein targets predicted or hypothesized to be biologically relevant.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Analyzing Cell Compositions with Mass Spectrometry

Provided in some aspects of the present application are methods for identifying a mass spectrometry (MS) profile of a cell composition, such as a composition of a genetically engineered cells. In some embodiments, the engineered cells express a recombinant protein, such as a recombinant receptor or a CAR. In particular embodiments, the methods include a step for determining a mass spectrometry profile e.g., a test mass spectrometry profile, of a sample from the engineered cell composition (e.g., the test cell composition) using a mass spectrometry technique. In some embodiments, the test mass spectrometry profile is compared to a reference mass spectrometry profile, such as for identifying differences between one or more data components of the mass spectrometry profiles.

Also provided in some aspects of the present application are methods for identifying a mass spectrometry (MS) profile of a genetically engineered cell composition, the methods comprising: (a) determining a test mass spectrometry profile of a sample from a test engineered cell composition using a mass spectrometry technique, said test engineered cell composition comprising immune cells comprising a recombinant receptor; (b) comparing the test mass spectrometry profile to a reference mass spectrometry profile; and (c) identifying one or more differences in the presence, absence, or level of at least one data component in the test mass spectrometry profile compared to the reference mass spectrometry profile, thereby identifying a mass spectrometry profile of the cell composition comprising the recombinant receptor.

A. Mass Spectrometry Profile

In some aspects mass spectrometry (MS) is a powerful analytical tool capable of gathering a vast amount of data from a sample. In certain aspects, mass spectrometry (such as described in a highly simplified manner) involves the detection of ions generated from a sample according to their mass-to-charge (m/z) ratios. In particular aspects, the MS signals from ions are used to generate mass spectra, which represent the relative abundance of the sample ions, or fragments thereof, as a function of their m/z ratio. In particular embodiments, the data obtained from a single or series of mass spectrometry analyses can subsequently be analyzed, such as compared against data obtained from another sample or another mass spectrometry analysis, at any number of informative levels of the acquired data, including at the levels of any combination of MS ion information, peptide and/or protein identification/sequence information, post-translation modification information, and quantification information. In the methods disclosed herein, the mass spectrometry profile of a sample or cell composition may comprise at least one data component selected from any single informative level or any combination of informative levels of acquired data from a single or series of mass spectrometry analyses, including any data component from any subsequent analysis of the acquired MS signal data and the resulting information therefrom. In some embodiments, the data component is a single data point, such as the presence of an identified peptide or the quantity of an identified peptide, including post-translational modifications thereof. In some embodiments, the data component is a collection of data points, such as the presence of a plurality of peptides or the quantity of a plurality of peptides, including post-translational modifications thereof.

In some embodiments, the mass spectrometry profile comprises a data component comprising MS ion information, such as signal of a MS ion. In some embodiments, the mass spectrometry profile comprises a data component comprising MS ion information of one or more protein and/or peptide species, including post-translational modifications thereof. In some embodiments, the mass spectrometry profile comprises a data component comprising MS ion information of one or more protein and/or peptide ion species, including post-translational modifications thereof. In some embodiments, the mass spectrometry profile comprises a data component comprising MS ion information of one or more fragments of a protein and/or peptide species, including post-translational modifications thereof. In some embodiments, the mass spectrometry profile comprises a data component comprising MS ion information of one or more fragments of a protein and/or peptide ion species, including post-translational modifications thereof. In some embodiments, the mass spectrometry profile comprises a data component comprising MS ion information of one or more MS analyses, or a portion thereof. In some embodiments, the mass spectrometry profile comprises a data component comprising a total ion current chromatogram. In some embodiments, the mass spectrometry profile comprises a data component comprising a total ion current chromatogram from more than one MS analysis. In some embodiments, the mass spectrometry profile comprises a data component comprising a portion of a total ion current chromatogram.

In some embodiments, the mass spectrometry profile comprises a data component comprising MS ion information manipulated to include and/or exclude one or more MS ions. In some embodiments, the mass spectrometry profile comprises a data component comprising an extracted ion chromatogram (XIC or EIC). In certain aspects, methods for producing extracted ion chromatograms are well known in the art, and include isolating MS ion information from an MS analysis for one or more m/z values of interest, for example, m/z values correlating with one or more peptides of interest. In some embodiments, the m/z value of interest includes an m/z range tolerance, e.g., a m/z window encompassing the m/z value of interest. In some embodiments, the m/z range tolerance is based on the mass spectrometer used to obtain the mass spectrometry profile. In some embodiments, the m/z range tolerance is less than about 50 ppm, such as less than about any of 40 ppm, 30 ppm, 20 ppm, 10 ppm, or 5 ppm. In some embodiments, the m/z range tolerance is about 50 ppm, such about any of 40 ppm, 30 ppm, 20 ppm, 10 ppm, or 5 ppm.

In some embodiments, the mass spectrometry profile comprises a data component comprising an extracted ion chromatogram, wherein extracted ion information is based on a property of one or more protein species and/or one or more peptide species of interest, including post-translational modifications thereof, such as the m/z of a MS ion of the one or more protein species and/or one or more peptide species of interest, including post-translational modifications thereof. In some embodiments, the mass spectrometry profile comprises a data component comprising an extracted ion chromatogram, wherein extracted ion information is based on one or more charged states of one or more protein species and/or one or more peptide species of interest, including post-translational modifications thereof. In some embodiments, the mass spectrometry profile comprises a data component comprising an extracted ion chromatogram, wherein extracted ion information is based on theoretical MS ion information. In some embodiments, the mass spectrometry profile comprises a data component comprising an extracted ion chromatogram, wherein extracted ion information is based on in silico MS ion information. In some embodiments, the mass spectrometry profile comprises a data component comprising an extracted ion chromatogram, wherein extracted ion information is based on in silico MS ion information representing a theoretically protease-digested protein. In some embodiments, the mass spectrometry profile comprises a data component comprising an extracted ion chromatogram, wherein extracted ion information is based on experimental MS ion information.

In some embodiments, the mass spectrometry profile comprises a data component comprising an extracted ion chromatogram, wherein extracted ion information is based on a property of a recombinant receptor, such as the m/z of a MS ion of the recombinant receptor, including any post-translational modifications thereof. In some embodiments, the mass spectrometry profile comprises a data component comprising an extracted ion chromatogram, wherein extracted ion information is based on in silico MS ion information representing a theoretically protease-digested recombinant receptor, including any post-translational modifications thereof. In some embodiments, the mass spectrometry profile comprises a data component comprising an extracted ion chromatogram, wherein extracted ion information is based on experimental MS ion information of a recombinant receptor, including any post-translational modifications thereof. In some embodiments, the mass spectrometry profile comprises a data component comprising an extracted ion chromatogram, wherein extracted ion information is based on a property of a transmembrane protein, such as the m/z of a MS ion of the transmembrane protein, including any post-translational modifications thereof. In some embodiments, the mass spectrometry profile comprises a data component comprising an extracted ion chromatogram, wherein extracted ion information is based on in silico MS ion information representing a theoretically protease-digested transmembrane protein, including any post-translational modifications thereof. In some embodiments, the mass spectrometry profile comprises a data component comprising an extracted ion chromatogram, wherein extracted ion information is based on experimental MS ion information of a transmembrane protein, including any post-translational modifications thereof. In some embodiments, the mass spectrometry profile comprises a data component comprising an extracted ion chromatogram, wherein extracted ion information is based on a property of a cell surface protein, such as the m/z of a MS ion of the cell surface protein, including any post-translational modifications thereof. In some embodiments, the mass spectrometry profile comprises a data component comprising an extracted ion chromatogram, wherein extracted ion information is based on in silico MS ion information representing a theoretically protease-digested cell surface protein, including any post-translational modifications thereof. In some embodiments, the mass spectrometry profile comprises a data component comprising an extracted ion chromatogram, wherein extracted ion information is based on experimental MS ion information of a cell surface protein, including any post-translational modifications thereof. In some embodiments, the mass spectrometry profile comprises a data component comprising an extracted ion chromatogram, wherein extracted ion information is based on a property of a chimeric antigen receptor (CAR), such as the m/z of a MS ion of the CAR, including any post-translational modifications thereof. In some embodiments, the mass spectrometry profile comprises a data component comprising an extracted ion chromatogram, wherein extracted ion information is based on in silico MS ion information representing a theoretically protease-digested CAR, including any post-translational modifications thereof. In some embodiments, the mass spectrometry profile comprises a data component comprising an extracted ion chromatogram, wherein extracted ion information is based on experimental MS ion information of a CAR, including any post-translational modifications thereof.

In some embodiments, the mass spectrometry profile comprises a data component comprising one or more peptide MS ion signal peaks. In some embodiments, the one or more peptide MS ion signal peaks comprises one or more charged states of a peptide, including any post-translational modifications thereof. In some embodiments, the one or more peptide MS ion signal peaks comprises one or more charged states of a peptide, including any post-translational modifications thereof, wherein the peptide is from a recombinant receptor. In some embodiments, the one or more peptide MS ion signal peaks comprises one or more charged states of a peptide, including any post-translational modifications thereof, wherein the peptide is from a transmembrane protein. In some embodiments, the one or more peptide MS ion signal peaks comprises one or more charged states of a peptide, including any post-translational modifications thereof, wherein the peptide is from a cell surface protein. In some embodiments, the one or more peptide MS ion signal peaks comprises one or more charged states of a peptide, including any post-translational modifications thereof, wherein the peptide is from a chimeric antigen receptor (CAR).

In some embodiments, the mass spectrometry profile comprises a data component comprising one or more protein MS ion signal peaks. In some embodiments, the one or more protein MS ion signal peaks comprises one or more charged states of a protein, including any post-translational modifications thereof. In some embodiments, the one or more protein MS ion signal peaks comprises one or more charged states of a protein, including any post-translational modifications thereof, wherein the protein is from a recombinant receptor or a fragment thereof. In some embodiments, the one or more protein MS ion signal peaks comprises one or more charged states of a protein, including any post-translational modifications thereof, wherein the protein is from a transmembrane protein or a fragment thereof. In some embodiments, the one or more protein MS ion signal peaks comprises one or more charged states of a protein, including any post-translational modifications thereof, wherein the protein is from a cell surface protein or a fragment thereof. In some embodiments, the one or more protein MS ion signal peaks comprises one or more charged states of a protein, including any post-translational modifications thereof, wherein the protein is from a chimeric antigen receptor (CAR) or a fragment thereof.

In some embodiments, the mass spectrometry profile comprises a data component comprising peptide identification information. In some embodiments, the peptide identification information comprises the identity of one or more peptides including any post-translational modifications thereof, including any characteristic, property, or observation of the identified peptide obtained from analysis by a mass spectrometry technique, for example, abundance and elution time from a liquid chromatograph. In some embodiments, the peptide identification information comprises the identity of one or more peptides, including any post-translational modifications thereof, of a single protein. In some embodiments, the peptide identification information comprises the identity of a pre-selected subset of peptides, including any post-translational modifications thereof, of a protein. In some embodiments, the peptide identification information comprises amino acid sequence information. In some embodiments, the peptide identification information comprises the identity of one or more peptides, including any post-translational modifications thereof, of a recombinant receptor, including any characteristic, property, or observation of the identified peptide obtained from analysis by a mass spectrometry technique. In some embodiments, the peptide identification information comprises the identity of a pre-selected subset of peptides, including any post-translational modifications thereof, of a recombinant receptor. In some embodiments, the peptide identification information comprises amino acid sequence information of a recombinant receptor, including any post-translational modifications thereof, or one or more fragments thereof. In some embodiments, the peptide identification information comprises the identity of one or more peptides, including any post-translational modifications thereof, of a transmembrane protein, including any characteristic, property, or observation of the identified peptide obtained from analysis by a mass spectrometry technique. In some embodiments, the peptide identification information comprises the identity of a pre-selected subset of peptides, including any post-translational modifications thereof, of a transmembrane protein. In some embodiments, the peptide identification information comprises amino acid sequence information of a transmembrane protein, including any post-translational modifications thereof, or one or more fragments thereof. In some embodiments, the peptide identification information comprises the identity of one or more peptides, including any post-translational modifications thereof, of a cell surface protein, including any characteristic, property, or observation of the identified peptide obtained from analysis by a mass spectrometry technique. In some embodiments, the peptide identification information comprises the identity of a pre-selected subset of peptides, including any post-translational modifications thereof, of a cell surface protein. In some embodiments, the peptide identification information comprises amino acid sequence information of a cell surface protein, including any post-translational modifications thereof, or one or more fragments thereof. In some embodiments, the peptide identification information comprises the identity of one or more peptides, including any post-translational modifications thereof, of a chimeric antigen receptor (CAR), including any characteristic, property, or observation of the identified peptide obtained from analysis by a mass spectrometry technique. In some embodiments, the peptide identification information comprises the identity of a pre-selected subset of peptides of a CAR, including any post-translational modifications thereof. In some embodiments, the peptide identification information comprises amino acid sequence information of a CAR protein, including any post-translational modifications thereof, or one or more fragments thereof.

In some embodiments, the mass spectrometry profile comprises a data component comprising protein identification information. In some embodiments, the protein identification information comprises the identity of one or more proteins including any post-translational modifications thereof, including any characteristic, property, or observation of the identified protein obtained from analysis by a mass spectrometry technique, for example, abundance and elution time from a liquid chromatograph. In some embodiments, the protein identification information comprises the identity of one or more recombinant receptors including any post-translational modifications thereof, including any characteristic, property, or observation of the one or more recombinant receptors obtained from analysis by a mass spectrometry technique. In some embodiments, the protein identification information comprises the identity of a pre-selected subset of recombinant receptors including any post-translational modifications thereof. In some embodiments, the protein identification information comprises amino acid sequence information of a recombinant receptor, including any post-translational modifications thereof, or one or more fragments thereof. In some embodiments, the protein identification information comprises the identity of one or more transmembrane proteins including any post-translational modifications thereof, including any characteristic, property, or observation of the one or more transmembrane proteins obtained from analysis by a mass spectrometry technique. In some embodiments, the protein identification information comprises the identity of a pre-selected subset of transmembrane proteins, including any post-translational modifications thereof. In some embodiments, the protein identification information comprises amino acid sequence information of a transmembrane protein, including any post-translational modifications thereof, or one or more fragments thereof. In some embodiments, the protein identification information comprises the identity of one or more cell surface proteins including any post-translational modifications thereof, including any characteristic, property, or observation of the one or more cell surface proteins obtained from analysis by a mass spectrometry technique. In some embodiments, the protein identification information comprises the identity of a pre-selected subset of cell surface proteins, including any post-translational modifications thereof. In some embodiments, the protein identification information comprises amino acid sequence information of a cell surface protein, including any post-translational modifications thereof, or one or more fragments thereof. In some embodiments, the protein identification information comprises the identity of one or more chimeric antigen receptors (CARs) including any post-translational modifications thereof, including any characteristic, property, or observation of the one or more CARs obtained from analysis by a mass spectrometry technique. In some embodiments, the protein identification information comprises the identity of a pre-selected subset of CARs, including any post-translational modifications thereof. In some embodiments, the protein identification information comprises amino acid sequence information of a CAR, including any post-translational modifications thereof, or one or more fragments thereof.

In some embodiments, the mass spectrometry profile comprises a data component comprising qualitative information, including presence of a MS ion, peptide, and/or protein, including any post-translational modifications thereof. In some embodiments, the mass spectrometry profile comprises a data component comprising qualitative information of a recombinant receptor or one or more fragments thereof. In some embodiments, the mass spectrometry profile comprises a data component comprising qualitative information of a transmembrane protein or one or more fragments thereof. In some embodiments, the mass spectrometry profile comprises a data component comprising qualitative information of a cell surface protein or one or more fragments thereof. In some embodiments, the mass spectrometry profile comprises a data component comprising qualitative information of a chimeric antigen receptor (CAR) or one or more fragments thereof.

In some embodiments, the mass spectrometry profile comprises a data component comprising quantitative information (i.e., abundance information). A diverse array of quantitative mass spectrometry techniques are known in the art. Quantitative mass spectrometry techniques are capable of providing, for example, absolute quantification (e.g., via selected reaction monitoring), semi-quantification (e.g., via chemical labeling), and relative quantification (e.g., via spectral counting). In some embodiments, the quantitative information is based on absolute quantification. In some embodiments, the quantitative information is based on semi-quantification. In some embodiments, the quantitative information is based on relative quantification.

In some embodiments, the mass spectrometry profile comprises a data component comprising structural information. In some embodiments, the mass spectrometry profile comprises a data component comprising post-translational modifications, including modifications that occur endogenously and during sample preparation.

In some embodiments, the mass spectrometry profile further comprises a data component comprising theoretical information. In some embodiments, theoretical information is based on known information obtained from any method including, but not limited to, a mass spectrometry technique. For example, a reference mass spectrometry profile may comprise theoretical MS ion information based on the known sequence of a protein or peptide.

In some embodiments, the methods disclosed in the present application contemplate a mass spectrometry profile comprising at least one data component, wherein the at least one data component comprises one or more data points. In some embodiments, wherein a mass spectrometry profile comprising two or more data components, the two or more data components may comprise information from any number of informative levels of the data acquired via a mass spectrometry technique, e.g., peptide identification information and quantitative information thereof. The mass spectrometry profiles disclosed herein are not limited to information obtained via one mass spectrometry analysis and/or technique. In some embodiments, the mass spectrometry profile comprises a data component comprising averaged or combined information, wherein the averaged or combined information comprises data from two or more mass spectrometry analyses and/or techniques.

In some embodiments, the methods disclosed in the present application contemplate the production and/or use of a mass spectrometry profile, such as a reference mass spectrometry profile or a test mass spectrometry profile, that accounts for variability or variance in one or more data components across multiple mass spectrometry profiles or mass spectrometry analyses, or in one or more analyzed samples, such as a plurality of test engineered cell compositions. For example, one of ordinary skill in the art will readily appreciate that two or more mass spectrometry analyses of the same sample may result in data with some variability, including differences in measured chromatography elution times, m/z values, relative intensity or abundance values, and associated or derived measurements, such as mass and AUC. In some embodiments, the mass spectrometry profile, such as the reference mass spectrometry profile or the test mass spectrometry profile, is an average of two or more mass spectrometry analyses. Moreover, in some embodiments, it may be desirable to compile at least a portion of two or more mass spectrometry profiles or data from two or more mass spectrometry analyses to generate a mass spectrometry profile, such as a reference mass spectrometry profile, for use in the methods described herein. Methods for generating a mass spectrometry profile, such as a reference mass spectrometry profile or a test mass spectrometry profile, from two or more mass spectrometry profiles or data from two or more mass spectrometry analyses are known in the art and include, e.g., available proteomic software.

In some embodiments, the m/z value of a measured species, such as a peptide or protein, including post-translational modifications thereof, varies between mass spectrometry profiles or analyses. In some embodiments, the measured m/z value variation is due to fluctuations in the measurements made by the mass spectrometer or across different mass spectrometers.

In some embodiments, the relative intensity or abundance values of a measured species, e.g., a peptide, vary between mass spectrometry profiles or analyses of the same sample. In some embodiments, the relative intensity or abundance values of a measured species, e.g., a peptide, vary between mass spectrometry profiles or analyses of multiple samples from the same cell composition. In some embodiments, the relative intensity or abundance values of a measured species, e.g., a peptide, vary between mass spectrometry profiles or analyses of samples from multiple cell compositions.

In some embodiments, the area under the curve (AUC) values of a measured species, e.g., a peptide, vary between mass spectrometry profiles or analyses of the same sample. In some embodiments, the AUC values of a measured species, e.g., a peptide, vary between mass spectrometry profiles or analyses of multiple samples from the same cell composition. In some embodiments, the AUC values of a measured species, e.g., a peptide, vary between mass spectrometry profiles or analyses of samples from multiple cell compositions.

In some embodiments, the elution times of a measured species, e.g., a peptide, vary between mass spectrometry profiles or analyses of the same sample. In some embodiments, the elution times of a measured species, e.g., a peptide, vary between mass spectrometry profiles or analyses of multiple samples from the same cell composition. In some embodiments, the elution times of a measured species, e.g., a peptide, vary between mass spectrometry profiles or analyses of samples from multiple cell compositions.

In some embodiments, the mass spectrometry profile, such as the reference mass spectrometry profile or the test mass spectrometry profile, is constructed based on one or more data components across multiple mass spectrometry profiles or analyses. In some embodiments, each of the data components comprises one or more MS ion signal peaks.

In some embodiments, the mass spectrometry profile, such as the reference mass spectrometry profile or the test mass spectrometry profile, is an average mass spectrometry profile. In some embodiments, the average mass spectrometry profile comprises the average intensity value of a measured species, e.g., a peptide, across multiple mass spectrometry profiles or analyses. In some embodiments, the average mass spectrometry profile comprises the average AUC value of a measured species, e.g., a peptide, across multiple mass spectrometry profiles or analyses. In some embodiments, the average mass spectrometry profile comprises the average elution time of a measured species, e.g., a peptide, across multiple mass spectrometry profiles or analyses. In some embodiments, the average mass spectrometry profile comprises the average m/z of a measured species, e.g., a peptide, across multiple mass spectrometry profiles or analyses. Exemplary methods of determining average data components include, but are not limited to, taking the mean, median, weighted average, or mode of the presence, absence, or level of raw, normalized, or preprocessed data components.

In some embodiments, the reference mass spectrometry profile further comprises unaveraged intensity values from all MS ion signal peaks across multiple mass spectrometry profiles. In some embodiments, the reference mass spectrometry profile further comprises unaveraged AUC values of all MS ion signal peaks across multiple mass spectrometry profiles. In some embodiments, the reference mass spectrometry profile comprises the unaveraged elution times of all MS ion signal peaks across multiple mass spectrometry profiles.

The mass spectrometry profiles disclosed herein may be obtained from a diverse array of cellular samples, which in turn can be prepared for and analyzed by a mass spectrometry technique in any number of different ways. In some embodiments, the mass spectrometry profile comprises a data component comprising information obtained from a sample comprising proteins, wherein at least two aliquots of the sample are prepared for analysis by one or more mass spectrometry techniques using at least two different sample preparation techniques. In view of the present disclosure, one or ordinary skill in the art will readily recognize the broad scope of what may constitute a mass spectrometry profile and that the disclosure of the present application is not limited by the exemplary descriptions provided herein.

The methods disclosed in the present application contemplate mass spectrometry profiles obtained from, for example, a test sample and a reference sample. In some embodiments, the mass spectrometry profile is a test mass spectrometry profile, wherein the test mass spectrometry profile is of a sample from a test engineered cell composition. In some embodiments, the mass spectrometry profile is a test mass spectrometry profile, wherein the test mass spectrometry profile is of a sample from a test engineered cell composition, said test engineered cell composition comprising immune cells comprising a recombinant receptor. In some embodiments, the mass spectrometry profile is a test mass spectrometry profile, wherein the test mass spectrometry profile comprises one or more data components comprising information from a sample from a test engineered cell composition. In some embodiments, the mass spectrometry profile is a test mass spectrometry profile, wherein the test mass spectrometry profile comprises one or more data components comprising information from a sample from a test engineered cell composition, said test engineered cell composition comprising immune cells comprising a recombinant receptor. In some embodiments, the test mass spectrometry profile comprises one or more data components comprising information from one or more mass spectrometry analyses, wherein the one or more mass spectrometry analyses are the same or different. In some embodiments, the test mass spectrometry profile comprises one or more data components comprising information from one or more mass spectrometry analyses, wherein the one or more mass spectrometry analyses are of samples prepared using one or more different sample preparation techniques. In some embodiments, the test mass spectrometry profile comprises one or more data components comprising information from one or more mass spectrometry analyses, wherein the one or more mass spectrometry analyses are the same or different, and wherein the one or more mass spectrometry analyses are of samples prepared using one or more different sample preparation techniques.

In some embodiments, the methods disclosed herein comprise determining a test mass spectrometry profile of a sample from a test engineered cell composition using a mass spectrometry technique, said test engineered cell composition comprising immune cells comprising a recombinant receptor. In some embodiments, the methods disclosed herein comprising obtaining a test mass spectrometry profile of a sample from a test engineered cell composition using a mass spectrometry technique, said test engineered cell composition comprising immune cells comprising a recombinant receptor.

In some embodiments, the mass spectrometry profile is a reference mass spectrometry profile. In some embodiments, the mass spectrometry profile is a reference mass spectrometry profile, wherein reference mass spectrometry profile is of a sample from a reference cell composition. In some embodiments, the mass spectrometry profile is a reference mass spectrometry profile, wherein the reference mass spectrometry profile is of a sample from a reference cell composition, said reference cell composition comprising immune cells. In some embodiments, the mass spectrometry profile is a reference mass spectrometry profile, wherein the reference mass spectrometry profile is of a sample from a reference cell composition, said reference cell composition comprising immune cells prior to transfection with a recombinant receptor.

In some embodiments, the mass spectrometry profile is a reference mass spectrometry profile, wherein the reference mass spectrometry profile comprises one or more data components comprising information from a sample from a reference cell composition. In some embodiments, the mass spectrometry profile is a reference mass spectrometry profile, wherein the reference mass spectrometry profile comprises one or more data components comprising information from a sample from a reference cell composition, said reference cell composition comprising immune cells. In some embodiments, the mass spectrometry profile is a reference mass spectrometry profile, wherein the reference mass spectrometry profile comprises one or more data components comprising information from a sample from a reference cell composition, said reference cell composition comprising immune cells prior to transfection with a recombinant receptor. In some embodiments, the reference mass spectrometry profile comprises one or more data components comprising information from one or more mass spectrometry analyses, wherein the one or more mass spectrometry analyses are the same or different. In some embodiments, the reference mass spectrometry profile comprises one or more data components comprising information from one or more mass spectrometry analyses, wherein the one or more mass spectrometry analyses are of samples prepared using one or more different sample preparation techniques. In some embodiments, the reference mass spectrometry profile comp comprises one or more data components comprising information from one or more mass spectrometry analyses, wherein the one or more mass spectrometry analyses are the same or different, and wherein the one or more mass spectrometry analyses are of samples prepared using one or more different sample preparation techniques.

In some embodiments, the methods disclosed herein comprise determining a reference mass spectrometry profile of a sample from a reference engineered cell composition using a mass spectrometry technique, said reference engineered cell composition comprising immune cells. In some embodiments, the methods disclosed herein comprise obtaining a reference mass spectrometry profile of a sample from a reference engineered cell composition using a mass spectrometry technique, said reference engineered cell composition comprising immune cells.

In some embodiments, the methods disclosed herein comprise determining a reference mass spectrometry profile of a sample from a reference engineered cell composition using a mass spectrometry technique, said reference engineered cell composition comprising immune cells comprising a recombinant receptor. In some embodiments, the methods disclosed herein comprise obtaining a reference mass spectrometry profile of a sample from a reference engineered cell composition using a mass spectrometry technique, in which the reference engineered cell composition contains or is enriched in immune cells expressing a recombinant receptor or in which such immune cells contain a heterologous polynucleotide that encodes a recombinant receptor.

B. Comparing Mass Spectrometry Profiles

In some embodiments, the methods disclosed herein comprise comparing mass spectrometry profiles. In some embodiments, the methods disclosed herein comprise comparing one or more test mass spectrometry profiles. In some embodiments, the methods disclosed herein comprise comparing one or more reference mass spectrometry profiles. In some embodiments, the methods disclosed herein comprise comparing a test mass spectrometry profile to a reference mass spectrometry profile. In some embodiments, the methods disclosed herein comprise comparing one or more test mass spectrometry profiles to one or more reference mass spectrometry profiles.

In some embodiments, the provided methods of comparing mass spectrometry profiles between and among cell compositions may be used to elucidate features or properties of an engineered cell composition, including features and properties of the recombinant receptor or a portion or component thereof, that may relate to or be associated with a particular process for producing the engineered cell composition, the effect of certain incubation or culture conditions, including the presence or absence of certain reagents, changes or alterations in the engineered cell composition upon stimulation, engineering (e.g., transduction) or recombinant receptor-dependent activation, such as upon exposure to an antigen or an anti-idiotypic antibody. In some aspects, such methods can be used to identify functional cellular levers that can inform or facilitate processes for the generation of engineered cell compositions. In some aspects, the provided methods are more powerful and/or provide orthogonal information as compared to existing methods for assessing characterizing cell proteins, such as flow cytometry and transcriptome-based analysis methods. For example, the mass spectrometry-based methods disclosed herein are capable of providing the ability to simultaneously profile a cellular sample in an unbiased manner (e.g., without a prior target hypothesis) for at least the following: peptide and protein expression, sequencing information, quantification, cellular location (e.g., via the selected sample preparation technique, such as isolation of cell surface proteins), and post-translational modifications.

Thus, in some embodiments, utility of the methods described herein may rely on a first mass spectrometry profile and a second mass spectrometry profile, such as a test mass spectrometry profile and a reference mass spectrometry profile, being capable of providing scientifically meaningful comparison, e.g., difference in presence and/or abundance of a protein or peptide. In some embodiments, generation of mass spectrometry profiles will thus require design and/or selection of sample preparation techniques and/or mass spectrometry techniques so that a first mass spectrometry profile of a first sample and a second mass spectrometry profile of a second sample may contain overlapping data components, in part or in whole, attributable to a single protein and/or peptide, if the single protein and/or peptide is present in the first sample and the second sample. For example, in some embodiments, the methods disclosed herein comprise analyzing a first sample from a first cellular composition and a second sample from a second cellular composition using the same or similar sample preparation techniques and the same or similar mass spectrometry techniques to generate a first mass spectrometry profile of the first sample and a second mass spectrometry profile of the second sample, thereby allowing for a comparison of the first mass spectrometry profile and the second mass spectrometry profile.

In some embodiments, the methods disclosed herein comprise identifying one or more differences in the presence, absence, or level of a least one data component in a test mass spectrometry profile compared to the reference mass spectrometry profile, thereby identifying a mass spectrometry profile of a cell composition comprising a recombinant receptor. As described throughout this application, the at least one data component comprised within a mass spectrometry profile includes any single informative piece of data or any combination of informative data obtained from a single or series of mass spectrometry analyses, including any piece of data from any subsequent analysis of the acquired MS signal data and the resulting information therefrom. Thus, for example, the one or more differences in the presence, absence, or level of a least one data component in a mass spectrometry profile may include differences in: MS ion information, a total ion chromatograph (TIC) or a portion thereof, an extracted ion chromatogram (XIC) or a portion thereof, peptide MS ion signal peak, protein MS ion signal peak, peptide identification information, such as differences in peptide sequences, protein identification information, qualitative information, quantitative information, structural information, and post-translation modifications.

In some embodiments, the methods disclosed in the present application contemplate calculating the amount of variability or variance in one or more data components across multiple mass spectrometry profiles or mass spectrometry analyses, or in one or more analyzed samples, such as a plurality of test engineered cell compositions. For example, one of ordinary skill in the art will readily appreciate that two or more mass spectrometry analyses of the same sample may result in data with some variability, including differences in measured chromatography elution times, m/z values, relative intensity or abundance values, and associated or derived measurements, such as mass and AUC.

In some embodiments, the m/z value of a measured species, such as a peptide or protein, including post-translational modifications thereof, varies between mass spectrometry profiles or analyses. In some embodiments, the measured m/z value variation is due to fluctuations in the measurements made by the mass spectrometer or across different mass spectrometers. In some embodiments, the amount of variability or variance in the measured m/z values of a measured species, e.g., a peptide, is calculated.

In some embodiments, the relative intensity or abundance values of a measured species, e.g., a peptide, vary between mass spectrometry profiles or analyses of the same sample. In some embodiments, the relative intensity or abundance values of a measured species, e.g., a peptide, vary between mass spectrometry profiles or analyses of multiple samples from the same cell composition. In some embodiments, the relative intensity or abundance values of a measured species, e.g., a peptide, vary between mass spectrometry profiles or analyses of samples from multiple cell compositions. In some embodiments, the amount of variability or variance in the relative intensity or abundance values of a measured species, e.g., a peptide, is calculated.

In some embodiments, the area under the curve (AUC) values of a measured species, e.g., a peptide, vary between mass spectrometry profiles or analyses of the same sample. In some embodiments, the AUC values of a measured species, e.g., a peptide, vary between mass spectrometry profiles or analyses of multiple samples from the same cell composition. In some embodiments, the AUC values of a measured species, e.g., a peptide, vary between mass spectrometry profiles or analyses of samples from multiple cell compositions. In some embodiments, the amount of variability or variance in the AUC values of a measured species, e.g., a peptide, is calculated.

In some embodiments, the elution times of a measured species, e.g., a peptide, vary between mass spectrometry profiles or analyses of the same sample. In some embodiments, the elution times of a measured species, e.g., a peptide, vary between mass spectrometry profiles or analyses of multiple samples from the same cell composition. In some embodiments, the elution times of a measured species, e.g., a peptide, vary between mass spectrometry profiles or analyses of samples from multiple cell compositions. In some embodiments, the amount of variability or variance in the elution times of a measured species, e.g., a peptide, is calculated.

Exemplary methods of determining the amount of variability across data components include, but are not limited to, taking the standard deviation, range, or interquartile range of the level of raw, normalized, or preprocessed data components, or taking the probability or proportion of the presence or absence of one or raw, normalized, or preprocessed data components.

C. Mass Spectrometry Techniques

The present application contemplates a diverse array of mass spectrometry techniques suitable for use with methods and method steps disclosed herein, including determining a mass spectrometry profile. In some embodiments, the methods disclosed herein comprise analyzing a sample from a test engineered cell composition using one or more mass spectrometry techniques. In some embodiments, the methods disclosed herein comprise analyzing a sample from a reference cell composition using one or more mass spectrometry techniques. As discussed herein, in some embodiments, mass spectrometry techniques can acquire data to provide a vast amount of information about a sample, including data components of any combination of MS ion information, peptide and/or protein identification/sequence information, post-translation modification information, and quantification information. In turn, a data component, or a plurality thereof, acquired from a mass spectrometer technique is used, for example, to produce a mass spectrometry profile. The following mass spectrometry techniques exemplified in the present section, as well as throughout this application, are exemplary techniques of mass spectrometry techniques useful for producing a mass spectrometry profile. However, the methods disclosed herein are not to be limited by the mass spectrometry techniques disclosed herein. In view of the disclosure herein, one of ordinary skill in the art will appreciate the extent of mass spectrometry techniques useful for the methods disclosed herein.

In some embodiments, the mass spectrometry technique comprises a liquid chromatography mass spectrometry technique. In some embodiments, the mass spectrometry technique comprises a liquid chromatography tandem mass spectrometry technique. In some embodiments, the mass spectrometry technique comprises a liquid chromatography technique.

The present application contemplates a diverse array of liquid chromatography techniques suitable for the methods disclosed herein. In some embodiments, the mass spectrometry technique comprises a liquid chromatography technique suitable for a proteomic application. In some embodiments, the mass spectrometry technique comprises a liquid chromatography technique suitable for separating peptides. In some embodiments, the mass spectrometry technique comprises separating peptides via a liquid chromatography technique.

Liquid chromatography techniques contemplated by the present application include methods for separating peptides and liquid chromatography techniques compatible with mass spectrometry techniques. In some embodiments, the liquid chromatography technique comprises a high performance liquid chromatography technique. Thus, in some embodiments, the liquid chromatography technique comprises an ultra-high performance liquid chromatography technique. In some embodiments, the liquid chromatography technique comprises a high-flow liquid chromatography technique. In some embodiments, the liquid chromatography technique comprises a low-flow liquid chromatography technique, such as a micro-flow liquid chromatography technique or a nano-flow liquid chromatography technique. In some embodiments, the liquid chromatography technique comprises an online liquid chromatography technique coupled to a mass spectrometer. In some embodiments, the online liquid chromatography technique is a high performance liquid chromatography technique. In some embodiments, the online liquid chromatography technique is an ultra-high performance liquid chromatography technique.

The liquid chromatography techniques contemplated herein comprise using a liquid chromatograph. In some embodiments, the liquid chromatograph comprises a high performance liquid chromatograph. In some embodiments, the liquid chromatograph comprises an ultra-high performance liquid chromatograph. In some embodiments, the liquid chromatograph comprises a high-flow liquid chromatograph. In some embodiments, the liquid chromatograph comprises a low-flow liquid chromatograph, such as a micro-flow liquid chromatograph or a nano-flow liquid chromatograph. In some embodiments, the liquid chromatograph comprises an online liquid chromatograph coupled to a mass spectrometer. In some embodiments, the liquid chromatograph comprises an online high performance liquid chromatograph, wherein the online high performance liquid chromatograph is coupled with a mass spectrometer. In some embodiments, the liquid chromatograph comprises an online ultra-high performance liquid chromatograph, wherein the online ultra-high performance liquid chromatograph is coupled with a mass spectrometer.

The liquid chromatography techniques and the liquid chromatographs contemplated for use with the methods disclosed in the present application are suitable for separating samples comprising a mixture of proteins and/or a mixture of peptides, prior to introduction of said sample into a mass spectrometer, using a chromatography column. In some embodiments, the liquid chromatography technique comprises a reversed-phase liquid chromatography technique. In some embodiments, the liquid chromatography technique comprises a normal-phase liquid chromatography technique. In some embodiments, the liquid chromatography technique comprises a size exclusion liquid chromatography technique. In some embodiments, the liquid chromatography technique comprises a high-performance anion-exchange chromatography technique. In some embodiments, the liquid chromatography technique comprises a hydrophilic interaction chromatography technique.

In some embodiments, the liquid chromatography technique comprises a capillary electrophoresis (CE) technique.

In some embodiments, the mass spectrometry technique comprises an autosampler technique. In some embodiments, the liquid chromatograph is coupled to an autosampler.

In some embodiment, the mass spectrometry technique comprises an ionization technique. Ionization techniques contemplated by the present application include techniques capable of charging proteins and peptides for analysis via a mass spectrometer. In some embodiments, the ionization technique is electrospray ionization (ESI). In some embodiments, the ionization technique is nano-electrospray ionization (nESI). In some embodiments, the ionization technique is atmospheric pressure chemical ionization. In some embodiments, the ionization technique is atmospheric pressure photoionizationionization. In some embodiments, the ionization technique is matrix-assisted laser desorption ionization (MALDI). In some embodiment, the mass spectrometry technique comprises an electrospray ionization, nano-electrospray ionization, or matrix-assisted laser desorption ionization (MALDI) technique.

Mass spectrometry techniques disclose herein comprise analyzing a sample comprising a protein mixture and/or a peptide mixture with a mass spectrometer system. The mass spectrometer systems contemplated for use with the methods disclosed herein include high-resolution mass spectrometers, low-resolution mass spectrometers, and hybrids of any combination thereof, and techniques association therewith. In some embodiments, the mass spectrometer system comprises an ion trap. In some embodiments, the mass spectrometer system comprises a quadrupole ion trap. In some embodiments, the mass spectrometer system comprises an orbitrap. In some embodiments, the mass spectrometer system comprises a quadrupole-orbitrap. In some embodiments, the mass spectrometer system comprises a time-of-flight (TOF) mass spectrometer. In some embodiments, the mass spectrometer system comprises a quadrupole-time-of-flight (Q-TOF) mass spectrometer. In some embodiments, the mass spectrometer system comprises a quadrupole ion trap time-of-flight (QIT-TOF) mass spectrometer. In some embodiments, the mass spectrometer system comprises a triple quadrupole (QQQ). In some embodiments, the mass spectrometer system comprises a fourier transform ion cyclotron resonance (FT) mass spectrometer. In some embodiments, the mass spectrometer system comprises a quadrupole-fourier transform ion cyclotron resonance (Q-FT) mass spectrometer.

In some embodiments, the mass spectrometer system is coupled with a liquid chromatograph, such as an online liquid chromatograph. In some embodiments, the mass spectrometer system is coupled with a liquid chromatograph and an autosampler.

In some embodiments, the mass spectrometry technique comprises a positive ion mode technique. In some embodiments, the mass spectrometry technique comprises a negative ion mode technique. In some embodiments, the mass spectrometry technique comprises a time-of-flight (TOF) mass spectrometry technique. In some embodiments, the mass spectrometry technique comprises a quadrupole time-of-flight (Q-TOF) mass spectrometry technique. In some embodiments, the mass spectrometry technique comprises an ion mobility mass spectrometry technique. In some embodiments a low-resolution mass spectrometry technique, such as an ion trap, or single or triple-quadrupole approach is appropriate.

In some embodiments, the mass spectrometry technique comprises performing MS' data acquisition with a scan resolution of 120,000. In some embodiments, the mass spectrometry technique comprises performing MS' data acquisition with a scan range of about 100 m/z to about 2000 m/z, such as about 325 m/z to about 2000 m/z. In some embodiments, the mass spectrometry technique comprises performing $MS^2$ data acquisition with a scan resolution of 30,000. In some embodiments, the mass spectrometry technique comprises performing $MS^2$ data acquisition with a scan range of about 100 m/z to about 2000 m/z, such as about 200 m/z to about 2000 m/z.

In some embodiments, the mass spectrometry technique comprises a tandem mass spectrometry technique. In some embodiments, the mass spectrometry technique comprises a data dependent acquisition technique. In some embodiments, the mass spectrometry technique comprises a data independent acquisition technique. In some embodiments, the mass spectrometry technique comprises a targeted mass spectrometry acquisition technique, including selected ion monitoring (SIM), selected reaction monitoring (SRM), and multiple reaction monitoring (MRM).

In some embodiments, the mass spectrometry technique is a quantitative mass spectrometry technique. In some embodiments, the quantitative mass spectrometry technique is an absolute quantification technique, such as SRM or MRM. In some embodiments, the quantitative mass spectrometry technique is a semi-quantitative technique, such as a label-based quantification method. In some embodiments, the quantitative mass spectrometry technique is a relative quantification technique, such as spectral counting. In some embodiments, the quantitative mass spectrometry technique is a label-based quantification technique. In some embodiments, the quantitative mass spectrometry technique is a label-free quantification technique.

In some embodiments, the methods disclosed herein further comprise processing the data acquired by the mass spectrometry technique. In some embodiments, the mass spectrometry technique comprises processing the obtained MS ion signals of a peptide or protein. In some embodiments, the mass spectrometry technique comprises peak detection. In some embodiments, the mass spectrometry technique comprises determining ionization intensity of a peptide ion. In some embodiments, the mass spectrometry technique comprises determining peak height of a peptide ion. In some embodiments, the mass spectrometry technique comprises determining peak area of the MS signal of a peptide ion. In some embodiments, the mass spectrometry technique comprises determining peak volume of a peptide and/or protein. In some embodiments, the mass spectrometry technique comprises quantifying a peptide ion and/or protein ion. In some embodiments, the mass spectrometry technique comprises quantifying a peptide and/or protein. In some embodiments, the mass spectrometry technique comprises identifying the sequence of a peptide and/or a protein, such as via a proteomics software. In some embodiments, the proteomics software identifies a peptide and/or protein sequence using known databases of gene or protein sequences of an organism, such as a human or mouse protein database. In some embodiments, the proteomics software identifies a peptide and/or a protein sequence de novo. In some embodiments, the mass spectrometry technique comprises manually validating the identification of a peptide and/or protein. In some embodiments, the mass spectrometry technique comprises identifying a peptide and/or a protein via a spectral library. Generally, use of spectral libraries allows for the imputation of knowledge gained regarding a peptide and/or a protein system and results in increased speed of data analysis with decreased error.

D. Sample Preparation Techniques

In some aspects of the present disclosure, the methods disclosed herein comprise performing a sample preparation technique. Generally, cellular samples may need processing for compatibility with a mass spectrometry technique, including protein/peptide isolation, removal of detergents, concentration/pooling of samples at any stage, and/or proteolytic digestion. In some embodiments, the sample preparation technique comprises a polypeptide isolation technique. In some embodiments, the polypeptide isolation technique isolates a subset of the cellular proteome, e.g., cell surface proteins, from other cellular components. In some embodiments, the polypeptide isolation technique isolates the cellular proteome, e.g., for whole cellular proteome analysis, from other cellular components. In some embodiments, the sample preparation technique comprises a polypeptide processing technique. In some embodiments of the methods disclosed herein, the methods comprise obtaining a sample that is compatible with a mass spectrometry technique.

1. Polypeptide Isolation Techniques

In some embodiments, the methods disclosed herein provide a polypeptide isolation technique, wherein the polypeptide isolation technique is suitable for isolating a subset of the cellular proteome from other cellular components. In some embodiments, the methods disclosed herein comprise a polypeptide isolation technique, wherein performing the polypeptide isolation technique isolates a recombinant receptor from other cellular components. In some embodiments, the methods disclosed herein comprise a polypeptide isolation technique, wherein performing the polypeptide isolation technique isolates a transmembrane protein from other cellular components. In some embodiments, the methods disclosed herein comprise a polypeptide isolation technique, wherein performing the polypeptide isolation technique isolates a cell surface protein from other cellular components. In some embodiments, the methods disclosed herein comprise a polypeptide isolation technique, wherein performing the polypeptide isolation technique isolates a chimeric antigen receptor (CAR) from other cellular components.

In some embodiments, the polypeptide isolation technique comprises: (a) labeling one or more proteins present in a sample from a cellular composition sample, thereby generating a labeled cellular composition sample; (b) lysing cells of the labeled cellular composition sample, thereby generating a lysed cellular composition sample; and (c) isolating the one or more proteins form the lysed cell composition to obtain one or more isolated proteins. In some embodiments, the polypeptide isolation technique comprises: (a) labeling one or more cell surface proteins present on cells of an engineered cellular composition sample, the cells of the engineered cellular composition sample comprising a recombinant receptor, thereby generating a labeled cellular composition sample; (b) lysing cells of the labeled cellular composition sample, thereby generating a lysed cellular composition sample; and (c) isolating the one or more cell surface proteins form the lysed cellular composition sample to obtain one or more isolated proteins.

In some embodiments, lysing the cells comprises incubation in the presence of a detergent. In some embodiments, the detergent is a non-ionic detergent, an anionic detergent, a cationic detergent, or a zwitterionic detergent. Exemplary detergents include, but are not limited to, maltosides, thiomaltosides, alkyl glycosides, and glycols. Exemplary detergents include, but are not limited to, n-Decyl-β-D-maltoside, n-Dodecyl-β-D-maltoside, n-Undecyl-β-D-maltoside, Cymal-5, Cymal-6, n-Dodecyl-β-D-thiomaltopyranoside, octyl glucose, neopentyl glycol, polyoxyethylene, Triton X-100, Triton X-114, C8E4, C8E5, C12E8, anapoe-35 (Brij-35), anapoe-58 (Brij-58), N-40, Tween 20, Tween 80, ethyl trimethyl ammonium bromide, octyl glucoside, and octyl thioglucoside.

In some embodiments, lysing the cells comprises incubation in the presence of a non-ionic detergent, an anionic detergent, a cationic detergent, a zwitterionic detergent, or any combination of two or more detergents thereof.

In some embodiments, lysing the cells comprises incubation in the presence of a denaturing detergent. In some embodiments, the denaturing detergent is an anionic detergent or a cationic detergent. Exemplary denaturing detergents include, but are not limited to, sodium dodecyl sulfate and ethyl trimethyl ammonium bromide. In some embodiments, the denaturing detergent is or comprises sodium dodecyl sulfate (SDS).

In some embodiments, lysing the cells comprises incubation in the presence of a non-denaturing detergent. In some embodiments, the non-denaturing detergent is a non-ionic detergent or a zwitterionic detergent. Exemplary non-denaturing detergents include, but are not limited to, Triton X-100, bile salts, such as cholate, and CHAPS.

In some embodiments, the detergent is a mass spectrometry-compatible detergent.

In some embodiments, lysing the cells comprises incubation in the presence of a detergent, wherein the concentration of the detergent is about 0.1% to about 5%, such as any of about 0.1% to about 4.5%, about 0.1% to about 4%, about 0.5% to about 3%, about 0.5% to about 2.5%, about 0.5% to about 2%, about 0.5% to about 1.5%, about 0.8% to about 1.2%, or about 0.9% to about 1.1%. In some embodiments, lysing the cells comprises incubation in the presence of a detergent, wherein the concentration of the detergent is less than about 5%, such as less than about any of 4.5%, 4%, 3.5%, 3%, 2.5%, 2%, 1.5%, 1%, or 0.5%. In some embodiments, lysing the cells comprises incubation in the presence of a detergent, wherein the concentration of the detergent is greater than about 0.5%, such as greater than about any of 1%, 1.5%, 2%, 2.5%, 3%, 3.5%, 4%, or 4.5%. In some embodiments, lysing the cells comprises incubation in the presence of a detergent, wherein the concentration of the detergent is about 0.5%, 1%, 1.5%, 2%, 2.5%, 3%, 3.5%, 4%, 4.5%, or 5%.

In some embodiments, labeling the surface proteins comprises labeling with an affinity agent or an affinity handle. In some embodiments, labeling the surface proteins comprises labeling with an affinity agent or an affinity handle, wherein affinity agent or the affinity handle is cell-impermeable. In some embodiments, labeling the surface proteins comprises biotin labeling. In some embodiments, labeling the surface proteins comprises biotin labeling of primary amines. In some embodiments, labeling the surface proteins comprises labeling with a click chemistry reagent.

In some embodiments, the one or more proteins are isolated using a reagent comprising avidin, streptavidin, NeutrAvidin™, or CaptAvidin™. In some embodiments, the one or more proteins are isolated using a reagent comprising a complementary click chemistry reagent.

In some embodiments, the polypeptide isolation technique isolates the cellular proteome, e.g., for whole cellular proteome analysis, from other cellular components.

In some embodiments, the polypeptide isolation technique further comprises a polypeptide purification step comprising removing a substance that is not compatible with a mass spectrometry technique, e.g., a surfactant or detergent, from a sample.

2. Polypeptide Processing Techniques

In some embodiments, the methods disclosed herein comprise performing a polypeptide processing technique. Generally, following a polypeptide isolation technique, polypeptide samples may need processing for compatibility with a mass spectrometry technique, including solvent modification, proteolytic digestion, and/or concentration. Such polypeptide isolation techniques are well known in the art and are contemplated for use with the methods of the present disclosure. Provided herein are exemplary polypeptide processing techniques, to which the methods of the present disclosure should not be limited.

In some embodiments, the polypeptide processing technique is a whole protein processing technique. In some embodiments, the whole protein processing technique comprises modifying or adjusting a solvent of a polypeptide sample. In some embodiments, the whole protein processing technique comprises concentrating a polypeptide sample. In some embodiments, the whole protein processing technique comprises denaturing a protein in a polypeptide sample. In some embodiments, the whole protein processing technique comprises purifying a protein in a polypeptide sample. In some embodiments, modifying or adjusting a solvent of a polypeptide sample, e.g., adding an acid to the polypeptide sample, such as trifluoroacetic acid or formic acid.

In some embodiments, the polypeptide processing technique is a digestion-based polypeptide processing technique. In some embodiments, the digestion-based polypeptide processing technique comprises denaturing a protein in a polypeptide sample. In some embodiments, the digestion-based polypeptide processing technique comprises modifying or adjusting a solvent of a polypeptide sample. In some embodiments, the digestion-based polypeptide processing technique comprises adding a reducing agent and/or an amino acid modifying agent, such as iodoacetamide, to a polypeptide sample. In some embodiments, the digestion-based polypeptide processing technique comprises a polypeptide digestion technique, such as via proteolytic and/or chemical digestion. In some embodiments, the polypeptide digestion technique comprises enzymatic digestion using a protease. In some embodiments, the protease one or more of trypsin, Lys-C, IdeS, IdeZ, PNGase F, thermolysin, pepsin, elastase, Arg-C, TEV, Glu-C, Asp-N, and Factor Xa. In some embodiments, sample digestion comprises chemical digestion, such as acid hydrolysis. In some embodiments, the digestion-based polypeptide processing technique comprises desalting a polypeptide sample. In some embodiments, the digestion-based polypeptide processing technique comprises concentrating a polypeptide sample. In some embodiments, the digestion-based polypeptide processing technique comprises purifying a peptide in a polypeptide sample. In some embodiments, modifying or adjusting a solvent of a polypeptide sample, e.g., adding an acid to the polypeptide sample, such as trifluoroacetic acid or formic acid.

In some embodiments, the polypeptide sample is divided into a first aliquot and a second aliquot, wherein the first aliquot is processed using a first polypeptide processing technique, wherein the second aliquot is processed using a second polypeptide processing technique, and wherein the first polypeptide processing technique and the second polypeptide processing technique are the same. In some embodiments, the polypeptide sample is divided into a first aliquot and a second aliquot, wherein the first aliquot is processed using a first polypeptide processing technique, wherein the second aliquot is processed using a second polypeptide processing technique, and wherein the first polypeptide processing technique and the second polypeptide processing technique are different.

E. Measuring Glycans

In particular embodiments, the changes or differences in expression of enzymes, e.g., glycotransferases, can be assessed, analyzed, or determined by detecting N-glycans presence on the surface of the cells. In some aspects, glycans are attached to proteins by post translational modification, such as to result in glycoproteins or proteoglycans. In general, glycans are found on the exterior surface of cells, such as conjugated to surface proteins. In some aspects, the glycan contains an oligosaccharide or a large number of monosaccharides that are linked glycosidically.

Particular embodiments contemplate that since specific glycan species are conjugated to proteins by specific enzymes, e.g., specific glycotransferases, detection of the presence, absence, level, or amount of one or more specific glycans indicate the presence, absence, level, amount, or activity of specific enzymes, e.g., specific glycotransferases, with corresponding activity, e.g., conjugation of the specific glycan to proteins as a post-translational modification. In some embodiments, post-translational modification of proteins by the addition of specific glycans are mediated by specific glycotransferases. Such glycotransferases include, but are not limited to, those encoded by the genes MGAT1, MGAT2, MGAT3, MGAT4A, MGAT4B, MGAT5, and MGAT5B. In some embodiments, the presence, absence, level, or amount of glycans, e.g., N-glycans, present on the cell surface are detected or measured as a readout of the presence, absence, level, or amount of one or more glycotransferases. In particular embodiments, the presence, absence, level, or amount of glycans, e.g., N-glycans, present on the cell surface are detected or measured as a readout of the presence, absence, level, or amount of one or more glycotransferases encoded by MGAT1, MGAT2, MGAT3, MGAT4A, MGAT4B, MGAT5, or MGAT5B.

In certain embodiments, the detection of the glycans may be performed by a technique capable of identifying and/or quantifying amounts of individual species of glycans. In certain embodiments, a species of glycans includes glycans that have identical structures that are different from the structures of other glycan species. In particular embodiments, the technique is a mass spectrometry technique and/or a liquid chromatography (LC) technique, such as high performance liquid chromatography (HPLC) or ultra performance liquid chromatography (UPLC). In some embodiments, the glycans are detecting using any suitable technique provided herein, e.g., in Section I.

In certain embodiments, a composition of cells is incubated, cultured, or treated under conditions suitable to remove, release, or detach glycans, e.g., N-glycans, from the surface of the cells of the composition. In certain embodiments, a composition of cells is treated, incubated, and/or contacted with an agent to remove, separate, or detach glycans, e.g., N-glycans, from the surface of the cells. In particular embodiments, the cells are intact, i.e., the cells are not lysed or homogenized prior to treatment with the agent. In certain embodiments, the cells are live cells. In some embodiments, treating, incubating, and/or contacting the cells with the agent does not disrupt and/or rupture the cell membrane. In some embodiments, the cells are live cells, and treating, incubating, or contacting the cells with the agent does not kill the cells. In certain embodiments, the cells are live cells, and treating, incubating, or contacting the cells with the agent does not induce cell death, e.g., apoptosis or necrosis in the cells.

In some embodiments, the composition of cells is treated, incubated, and/or contacted with an agent such as an. N-glycosidase, e.g. PNGase F, resulting in a removal, separation, and/or detachment of glycans, e.g., N-glycans, from surface exposed glycoconjugate. In some embodiments, the glycoconjugate is a protein, e.g., a glycoprotein. In particular embodiments, the treating, contacting, and/or incubating the composition of the cells with the agent results in the removal, separation, and/or detachment of glycans from a surface exposed protein. In particular embodiments, the released, removed, and/or detached N-glycans are intact. In some embodiments, the removal, separation, and/or detachment of the glycans from the surface exposed protein does not damage, digest, and/or otherwise alter the structure of the glycan. In particular embodiments, the removal, separation, and/or detachment of the glycans from the surface exposed protein does not damage, digest, and/or otherwise alter the structure of the moiety, e.g., protein, from which the glycan has been released. In some embodiments, the removal, separation, and/or detachment of the glycans from the surface exposed protein results in the conversion of asparagine to aspartate, but does not otherwise damage, digest, and/or alter the structure of the protein from which the glycan has been released.

In some embodiments, the agent is any agent that facilitates the removal, separation, and/or detachment of glycans, e.g., N-glycans, from a glycoconjugate, e.g., a glycoprotein. In certain embodiments, the agent chemically removes the glycan from the glycoconjugate, for example but not limited to hydrazinolysis or alkali β-elimination.

In certain embodiments, the agent is an enzyme. In particular embodiments, the agent is an enzyme that specifically removes, separates, and/or detaches N- or O-linked glycans from a glycoconjugate. In certain embodiments, the agent is an amidase. In some embodiments, the agent is or includes a glycosidase, such as an N-glycosidase. In particular embodiments, the agent is or includes Endoglycosidase H (Endo H), Endoglycosidase F (EndoF), N-Glycosidase A (PNGase A), or N-Glycosidase F (PNGase F) or combinations thereof. In some embodiments, the agent is or includes an amidase of the peptide-N4-(N-acetyl-beta-glucosaminyl) asparagine amidase class. In particular embodiments the agent is or includes a PNGase F.

In some embodiments, the agent is an enzyme that releases or is capable of releasing full-length oligosaccharides from proteins and peptides having N-linked carbohydrates. In some embodiments, the agent is a PNGase F that releases, or is capable of releasing, full-length oligosaccharides from proteins and peptides having N-linked carbohydrates. In certain embodiments, the agent is not or does not include endoglycosidases, such as Endo F, Endo H, and Endo D. In some embodiments, endoglycosidases, such as Endo F, Endo H, and Endo D do not release full-length oligosaccharides and/or do not cleave all common classes of N-linked oligosaccharides from glycoproteins.

In certain embodiments, the agent is not a protease. In some embodiments, the agent does not include a protease. In particular embodiments, the agent is not serine protease, a cysteine protease, a threonine protease, an aspartic protease, a glutamic protease, a metalloprotease, or asparagine peptide lyases. In certain embodiments, the agent is not and does not include an endopeptidase, e.g., trypsin, chymotrypsin, pepsin, papain, and elastase. In particular embodiments, the agent is not and does not include trypsin.

In particular embodiments, incubation under conditions that are suitable to remove, release, or detach glycans from the surface of cells includes contacting, treating, and/or incubating the cells with an agent. In particular embodiments, the agent is or includes a PNGase F. PNGase F is an amidase of the peptide-N4-(N-acetyl-beta-glucosaminyl) asparagine amidase class. In some embodiments, PNGase F is a bacterial enzyme that releases N-glycans from an asparagine. In particular embodiments, the PNGase F releases the entire, i.e., intact, N-glycan from the asparagine. In certain embodiments, PNGase F removes oligomannose, hybrid, and complex N-glycans attached to asparagine. In particular embodiments, PNGase F releases N-glycans attached to the nitrogen of asparagine, thereby converting asparagine to aspartate. In certain embodiments, the cleavage occurs at a position of the carbohydrate that is adjacent to the asparagine residue. In particular embodiments, the agent is or includes an enzyme that exhibits peptide-N-(N-acetyl-β-N-glucosaminyl) asparagine aminidase activity. In certain embodiments, a composition of cells is treated, contacted, or incubated with an agent that is or includes a PNGase F.

In some embodiments, the PNGase F is a recombinant PGNase F. In certain embodiments, the PNGase F a mutant PNGase F. In some embodiments, the PNGase F is a recombinant PNGase F that is cloned from *Flavobacterium meningosepticum*. In particular embodiments, the PNGase F is cloned from the entire PNGase F gene of *Flavobacterium meningosepticum*. In certain embodiments, the entire PNGase F gene of *Flavobacterium meningosepticum* is the PNGase F gene described in Tarentino et al., Journal of Biological Chemistry, 265(12): 6961-6966 (1990). In particular embodiments, the entire PNGase F gene is a PNGase F gene that encodes a PNGase F polypeptide that is designated with the Uniprot Accession number P21163.2. In some embodiments, the entire PNGase F gene is a PNGase F gene that encodes a PNGase F polypeptide with the amino acid sequence set forth in SEQ ID NO: 61.

In particular embodiments, the agent is or includes the PNGase F that is produced from a polynucleotide that is cloned from the entire PNGase is entire Peptide N-Glycosidase F(PNGase F) gene from the genome of *Flavobacterium meningosepticum*, expressed and purified into the T7 expression vectors pET 29-b (Novagen) and pQE-T7(Qiagen). In certain embodiments, the polynucleotide that encodes the PNGase F contains an in-frame C-terminal histidine tag. In some embodiments, the polynucleotide encoding the PNGase F HIS-tagged construct is transformed into bacterial strain BL21 Star (DE3) that carries the gene for the T7 RNA polymerase under control of the lacUV5 promoter which allows for high level isopropyl-beta-D-thiogalactopyranoside (IPTG) inducible expression of gene products from T7expression vectors such as pET and pQE. In particular embodiments, bacterial transformation and cell culture growth is performed, bacterial cells are harvested by centrifugation, and cell pellets are washed with buffers containing protease inhibitors (SigmaFast EDTA-free). In particular embodiments, the total cellular protein lysates are made using an Avestin C5 high pressure homogenizer. In some embodiments, FPLC purification methods for the recombinant PNGase F histidine tagged protein use Ni-NTA (Qiagen) and IMAC HisTrap HP (GE Healthcare) columns. In some embodiments, bacterial cell lysate from IPTG induced cultures are loaded onto the column and bound the PNGase F polypeptide with the C-terminal His tag is washed and eluted using an imidazole step gradient in binding buffer. In some embodiments, purified PNGase F with the C-terminal is dialyzed and stored in PBS buffer. In particular embodiments, the agent is or includes a PNGase that is a recombinant PNGase F with a C-terminal His tag or is a PNGase F that is identical to a PNGase F produced by the methods described in Powers et al. Analytical Chemistry, 85(20): 9799-806 (2013).

In some embodiments, the agent is or includes a PNGase F that is a commercially available PNGase F. Commercially available PNGase F includes, but is not limited to, PNGase F Proteomics Grade (Catalog # P 7367, Sigma); PNGase F (Catalog # P0704S and P0704L, New England Biolabs), PNGase F (Catalog # V4831, Promega), N-GLYCANASE (Catalog #: GKE-5006A, GKE-5006B, GKE-5006D, GKE-5016A, GKE-5016B, GKE-5016D, GKE-5010B, GKE-5016D, GKE-5020B, GKE-5020D, and GKE-5003, ProZyme), and PNGase F (Catalog #: E-PNG01, QA Bio), RAPID PNGase F (Catalog # P0710S, New England Biolabs), PNGASE F PRIME (N-Zyme Scientifics). In certain embodiments, the PNGase F is or is identical to PNGASE F PRIME (N-Zyme Scientifics).

In particular embodiments, the cells are removed from a sample, solution, or media that contains released surface glycans. In certain embodiments, the glycans are removed and/or separated from the media or solution. In some embodiments, the solution or media is evaporated. In particular embodiments, the solution or media is evaporated by vacuum centrifugation, e.g., with a speedvac. In particular embodiments, the glycans are removed and/or separated from the media or solution and are then resuspended. In some embodiments, the glycans may be resuspended in a volume of a buffer or solution. In some embodiments, the buffer or solution is suitable for storage. In certain embodiments, the buffer is suitable for use with a technique for the detection, identification, and/or detection of the glycans. In certain embodiments, the buffer or solution is suitable for a chemical reaction, e.g., a derivation reaction such as the addition of a detectable label.

In certain embodiments, glycans, e.g. N-glycans, are modified to improve and/or enhance the detection of the glycans. In many instances, glycans may not be readily detectable due to the absence of a strong chromophore or fluorophore or active moiety that is detectable by liquid chromatography and/or mass spectrometry. In some embodiments, the absorbance and fluorescence response of a glycan may be relatively weak or below a threshold for detection. In some embodiments, one tactic to maximize the sensitivity of an assay is to convert the compound of interest, i.e., the glycan, into a derivative that exhibits a better response for the particular detection method being utilized. In certain embodiments, the derivatizing agent affects or influences the ultimate sensitivity and accuracy of an analysis by maximizing the sensitivity, yield and/or stability of the derivatized molecules. Thus, in some embodiments, the glycans (e.g., N-glycans) that have been released from cellular surfaces are derivatized prior to any procedures for analysis or detection.

In some embodiments, the glycans are derivatized prior to an analysis by HPLC and/or mass spectrometry. In some embodiments, the sensitivity of the detection of N-glycans by existing techniques, e.g., high performance liquid chromatography (HPLC) and/or optical or mass spectrometric (MS) detection, can be improved and/or enhanced by a derivation step.

In some embodiments, a glycan, e.g., an N-glycan, is derivatized to allow for or improve detection by mass spectrometry. In certain embodiments, the glycan is derivatized to allow for the glycan to more easily accept a charge. In certain embodiments, a glycan and/or a derivatized glycan that is capable of accepting charge is detectable by a mass spectrometer. In some embodiments, the glycan is derivatized by adding an amino group, e.g., a tertiary amino group.

In some embodiments, the derivatization is or includes adding a detectable label to the glycans, e.g., N-glycans. In some embodiments, the addition is a covalent attachment. In certain embodiments, the attached detectable label increases signal and/or reduce background noise during the detection of the N-glycans as compared to detection of N-glycans that do not contain an attached detectable label. In certain embodiments, any of a variety of detectable labels can be used in accordance with the present disclosure, including but not limited to, fluorescent labels, radiolabels and/or chemiluminescent labels. In certain embodiments, the detectable label is a fluorescence label. In certain embodiments, attachment, e.g., covalent attachment, of the fluorescence label does not alter migration of the N-glycan in a column, e.g., a column suitable for HPLC. In particular embodiments, the label is a fluorescence label and allows for the glycan to more easily accept a charge as compared to an unlabeled glycan.

In some embodiments, the derivatization of the N-glycans is performed by a standard technique in the art. A large number of N-glycan derivatization techniques have been described and are reviewed in Ruhaak et al., Analytical and Bioanalytical Chemistry 397(8): 3457-3481 (2010). In some embodiments, the derivatization is performed by a chemical reaction that includes two or more reaction steps. In some embodiments, derivatization is performed by reaction reductive amination, permethylation, Michael addition, or hydrazide labeling. In certain embodiments, various compounds which provide the required functional group for the labeling reaction can be used. In certain embodiments, the derivatization is performed by a chemical reaction with a single reaction step. Labeling agents that add a label to a glycan by Chemical reaction with a single reaction step that are suitable for derivatization and/or covalently attaching a detectable label to an N-glycan includes agents that contain a functional group that rapidly reacts with amines (such as an isocyanate, or succidimidylcarbamate). Such labeling agents and fluorescence labels are described in U.S. Pat. App. No: US 20140242709.

In certain embodiments, the N-glycans are labeled by reductive amination. In this reaction, a label containing a primary amine group reacts in a condensation reaction with the aldehyde group of the glycan, resulting in an imine or Schiff base, which is reduced by a reducing agent to yield a secondary amine. In some embodiments, the reaction is performed in dimethyl sulfoxide containing acetic acid, tetrahydrofuran, or methanol. In some embodiments, reductive amination results in the stoichiometric attachment of one label per N-glycan allowing a direct quantitation based on fluorescence or UV-absorbance intensity.

Various labels have been used for the reductive amination of glycans. In some embodiments, fluorescent label that is or includes 2-aminobenzamide (2-AB), 2-aminobenzoic acid (2-AA), 2-aminopyridine (PA), 2-Aminoacridone (AMAC), 2-aminonaphthalene trisulfonic acid (ANTS), and 1-aminopyrene-3,6,8-trisulfonic acid (APTS), 3-(Acetylamino)-6-aminoacridin (AA-Ac), 6-Aminoquinoline (6-AQ), 7-Aminomethyl-coumarin (AMC), 2-Amino (6-amido-biotinyl) pyridine (BAP), 9-Fluorenylmethoxycarbonyl (FMOC)-hydrazide, 1,2-Diamino-4,5-methylenedioxy-benzene (DMB), or o-Phenylenediamine (OPD) is added to the glycans.

In particular embodiments, the N-glycans are labeled with a commercially available label. Labeling kits are available for the tags 2-AB, 2-AA, and PA (Ludger) as well as for labeling with APTS (Beckmancoulter) and ANTS (Prozyme). In some embodiments, the labeling agent and/or the fluorescence label is RapiFluor-MS (Waters Technologies Corporation).

In some embodiments, the labeling agent contains a fluorescent moiety, and a functional group that rapidly reacts with amines (such as an isocyanate, or succidimidylcarbamate). In some embodiments, the labeling agent contains one or more of a tertiary amino group or other MS active atom, a fluorescent moiety, and a functional group that rapidly reacts with amines (such as an isocyanate, or succidimidylcarbamate).

In particular embodiments, a sample of the extracellular solution that contains the glycans is prepared for analysis, e.g., mass spectrometry analysis. In some embodiments, the sample of glycans, e.g. N-glycans, is purified prior to the analysis. In some embodiments, the purification includes any method capable of separating N-glycans from any entities which will or will potentially disrupt, hinder, and/or weaken the detection of the N-glycans. In some embodiments, the purification step is performed to remove the N-glycans from cellular debris, deglycosylated protein, PNGase F, buffer/formulation components, surfactants, labeling reaction byproducts, and/or excess labeling and/or derivatization reagents. In particular embodiments, the purification step is performed on labeled glycans, e.g. N-glycans, e.g., glycans with covalently attached detectable labels. In certain embodiments, the purification is performed by any suitable technique for purifying glycans, including but not limited to solid phase extraction (SPE), liquid-liquid extraction, gel filtration, paper chromatography, and precipitation.

In certain embodiments, the glycans, e.g., the N glycans, are analyzed by mass spectrometry, such as by any suitable mass spectrometry technique described herein, e.g., in Section I. In particular embodiments, a cell composition, e.g., a test T cell composition, is analyzed by removing glycans from the surface of the cells, purifying and derivatizing the glycans, and measuring the glycans with a mass spectrometry technique, e.g., LC-MS. In some embodiments, the presence, absence, level, or amount of glycans, e.g., N-glycans, present on the cell surface are detected or measured as a readout of the presence, absence, level, or amount of one or more glycotransferases. In particular embodiments, the presence, absence, level, or amount of glycans, e.g., N-glycans, present on the cell surface are detected or measured are correlated to the presence, absence, level, or amount of one or more glycotransferases as detected in the sample, for example a genomic technique such as RNA-seq or Assay for Transposase-Accessible Chromatin using sequencing (ATAC-seq). In particular embodiments, the presence, absence, level, or amount of glycans, e.g., N-glycans, present on the cell surface are detected or measured as a readout of the presence, absence, level, or amount of one or more glycotransferases encoded by MGAT1, MGAT2, MGAT3, MGAT4A, MGAT4B, MGAT5, or MGAT5B.

II. Cell Compositions

In some embodiments, the provided methods herein can be used to determine, measure, or assess the presence, level, amount, or expression of proteins, e.g., surface proteins, of a cell composition by identifying a mass spectrometry profile of the cell composition. In some embodiments, the mass spectrometry profile is identified by any of the provided methods described herein, e.g., in Section I. In certain embodiments, the methods are or include a mass spectrometry technique. In some embodiments, the provided methods can be used to assess or analyze the presence, absence, amount, level and/or relative abundance of one more proteins on the surface of the cells of the composition.

In certain embodiments, a mass spectrometry profile (e.g., a test mass spectrometry profile) is generated from a test cell composition. In particular embodiments, a test cell composition may be any cell composition where one or more markers, features, properties, phenotypes, or attributes are measured or a desired to be measured by any of the methods provided herein, e.g., in Section I, such as by generating a mass spectrometry profile. In some embodiments, the test composition is a composition of mammalian cells. In particular the test composition is a composition of human cells. In particular embodiments, the composition of test cells are or contain cells that are suitable for genetic engineering (e.g., to produce a cell therapy), are collected during a process for genetic engineering (e.g., to produce a cell therapy), or have been genetically engineered (e.g., a cell therapy containing genetically engineered cells).

In particular embodiments, the mass spectrometry profile is generated from a test cell composition, e.g., an immune cell composition containing CAR T cells, to assess or evaluate levels, amounts, or changes of proteins, e.g., surface proteins. In some embodiments, the levels, amounts, or changes in proteins, e.g., surface proteins, indicate functional and/or phenotypic characteristics, properties, or attributes of the cells, such as in connection with one or more of viability, metabolic activity, differentiation state, proliferative capacity, activation state, or cytolytic activity.

In some embodiments, the test cell composition is cell therapy. In particular embodiments, the test cell composition is a cell therapy that is a candidate for administration to a subject, e.g., a human subject. In certain embodiments, the test cell composition is an autologous cell therapy. In certain embodiments, the test cell composition is an immune cell therapy. In certain embodiments, the test cell composition is an autologous CAR T cell therapy. In some embodiments, the test cell composition is a cell composition that will be developed, processed, or engineered into a cell therapy. In particular embodiments, the test cell therapy is a cell composition that will be developed, processed, or engineered into an autologous CAR T cell therapy. In certain embodiments, the test cell composition is a composition of cells collected during a process to generate or engineer a cell therapy. In various embodiments, the test cell composition is a composition of cells collected during an process to engineer an autologous T cell therapy.

In some embodiments, the test cell composition is a composition of human cells, e.g., human immune cells such as T cells, that will undergo a process for generic engineering, such as to generate a composition of engineered T cells. In certain embodiments, the cells are suitable for or will undergo any one of the processes for genetic engineering described herein, e.g., in Section-III. In certain embodiments, the test cell composition is a composition of human cells, e.g., human immune cells, that include genetically engineered cells that have undergone a process for generic engineering, such as to generate a composition of engineered T cells. In certain embodiments, the cells have undergone any one of the processes for genetic engineering described herein, e.g., in Section-III. In particular embodiments, the test cell composition is a T cell composition that is suitable for or that will undergo any one of the processes for genetic engineering described herein, e.g., in Section-III, to produce an engineered T cell composition containing T cells expressing a recombinant receptor, e.g., a CAR. In certain embodiments, the test cell composition is a an engineered T cell composition containing T cells expressing a recombinant receptor, e.g., a CAR. In certain embodiments, the engineered T cell composition has undergone a process for genetically engineering cells described herein, e.g., in Section-III.

In various embodiments, the test cell composition is a composition of human cells, e.g., human immune cells such as T cells, that are collected during a process to generate a composition of engineered T cells. In certain embodiments, the cells are collected during any stage or time point of any one of the processes for generating engineered cells described herein, e.g., in Section-III. In particular embodiments, the test cell composition contains activated or stimulated T cells. In certain embodiments, the activated or stimulated T cells have been incubated under stimulatory conditions, such as any of those described herein, e.g., in Section III-B. In certain embodiments, the test cell composition contains transformed or transfected T cells. In certain embodiments, a heterologous polynucleotide, such as one encoding a recombinant receptor or CAR, has been introduced or delivered to the T cells. In particular embodiments, the described herein, e.g., in Section III-C. In particular embodiments, the test cell composition contains cultivated or expanded T cells. In certain embodiments, the T cells have been cultivated or expanded according to any method provided herein, e.g., in Section III-D.

In some embodiments, the test cell composition includes or contains immune cells that express a recombinant receptor. In particular embodiments, the test cell composition contains T cells, e.g., CD4+ or CD8+ T cells that express a recombinant receptor. In certain embodiments, the recombinant receptor is an antigen receptor. In particular embodiments, the recombinant receptor is a CAR. In certain embodiments, the recombinant receptor is any CAR that is described herein, e.g., in Section II-C-1-a or II-C-1-b. In particular embodiments, the recombinant receptor is a recombinant TCR, e.g., a recombinant TCR described herein such as in Section II-C-1-c. In some embodiments, the recombinant receptor is an anti-CD19 CAR. In certain embodiments, the recombinant receptor is an anti-BCMA CAR.

In certain embodiments, mass spectrometry profiles are generated from more than one test cell compositions. In certain embodiments, mass spectrometry profiles are generated from two, three, four, five, more than five, more than ten, more than twenty, more than fifty, or more than 100 test cell compositions. In certain embodiments, mass spectrometry profiles are generated from more than one test cell compositions to determine a mean, median, or average level or amount of one or more proteins, e.g., surface proteins, of a plurality of test cell compositions. In some embodiments, mass spectrometry profiles are generated from more than one test cell compositions to determine a variability or variance in the level or amount of one or more proteins, e.g., surface proteins, among a plurality of test cell compositions.

In some embodiments, the test cell composition contains cells expressing a recombinant receptor. In some embodiments, the mass spectrometry profile of a test cell composition is compared to a profile of a composition of cells that express a different recombinant receptor. In certain embodiments, the mass spectrometry profile of the test cell composition is compared to a composition of cells that do not express a recombinant receptor. In some embodiments, the mass spectrometry profile from the test cell composition may be compared to a mass spectrometry profile from a composition of cells that is produced by a different process. In some embodiments, the mass spectrometry profile of a test cell composition is compared to a different cell composition from a different stage or step of a manufacturing process.

In particular embodiments, the mass spectrometry profile of a test cell composition is compared to a mass spectrometry profile of a cell composition of cells that were collected at an earlier stage of an engineering process, e.g., earlier than when the cells of the test cell composition were collected. In some embodiments, the mass spectrometry profile of a test cell composition is compared to a mass spectrometry profile of a cell composition of cells that were collected at a later stage of an engineering process, e.g., later than when the cells of the test cell composition were collected. In some embodiments, a mass spectrometry profile from a test cell composition is compared to mass spectrometry profile from a cell composition that was at the same stage of a manufacturing process but was exposed to different conditions, e.g., different from the conditions cells from the test cell composition were exposed to.

In some embodiments, a mass spectrometry profile of a test cell composition, e.g., a test mass spectrometry profile is compared to a reference mass spectrometry profile. In certain embodiments, the reference mass spectrometry profile is a theoretical profile. In some embodiments, the theoretical profile is based on proteins (and levels, amounts, or modifications thereof) predicted to be in or expressed by cells of the cell composition. In particular embodiments, the theoretical profile is based on proteins (and levels, amounts, or modifications thereof) that are predicted to be in or expressed by cells of a cell composition that is considered to be an ideal cell composition.

In some embodiments, the reference mass spectrometry profile is obtained from a reference cell composition.

In certain embodiments, a reference cell composition contains cells expressing a recombinant receptor. In particular embodiments, the recombinant receptor is also expressed by cells contained by the test cell composition. In certain embodiments, a reference cell composition and the test cell composition each contain cells expressing the same recombinant receptor. In some embodiments, a reference cell composition is generated from cells that obtained from the same subject as a test composition. In certain embodiments, a reference cell composition is generated from cells that were obtained from a subject that was different from the subject from whom the cells for generating the test composition were obtained. In particular embodiments, the reference cell composition (i) was generated from the cells obtained from the same subject as the cells used to generate the test cell composition and (ii) contains cells that expresses a different recombinant receptor as cells in the test composition. In various embodiments, the reference cell composition (i) was generated from the cells obtained from a different subject as the cells used to generate the test cell composition and (ii) contains cells that expresses the same recombinant receptor as cells in the test composition. In certain embodiments, the recombinant receptor is a CAR.

In some embodiments, a reference cell composition contains cells that were collected at an earlier stage of an engineering process than the stage at which the cells of the test cell composition were collected. In certain embodiments, the reference cell composition contains cells that were collected at a later stage of an engineering process than when the cells of the test cell composition were collected. In certain embodiments, the reference cell composition contains cells that were collected at the same stage of a manufacturing process as the cells of the test composition. In particular embodiments, the reference cell composition contains cells that were collected at the same stage of a manufacturing process as the cells of the test composition but were exposed to different conditions.

In particular embodiments, the reference mass spectrometry profile is obtained from a plurality of reference cell compositions. In certain embodiments, the plurality includes, includes about, or includes at least 2, 3, 4, 5, 10, 15, 20, 25, 30, 40, 50, 100, 200, 500, or 1,000 reference cell compositions. In particular embodiments, the reference mass spectrometry profile is or includes the average, mean, or median value of the mass spectrometry profiles obtained from the reference mass spectrometry profile.

A. Cells Types

Particular embodiments contemplate that any composition containing cells can be assessed according to the provided method. In some embodiments, the population of cells is or comprises a cell line or primary cells. In some embodiments, the population of cells is or comprises primary cells, such as primary cells obtained from a subject, e.g. human subject. In some embodiments, the population of cells is or comprises stem cells, such as induced pluripotent stem cells. In some embodiments, the composition of cells, e.g. source composition or a portion thereof, such as a test cell composition, is a composition that is associated with a process for manufacturing a cell composition, including in connection with engineering cells with a recombinant nucleic acid. In some embodiments, the composition of cells is a pharmaceutical composition.

In certain embodiments, the cells are or include eukaryotic cells. In certain embodiments, the cells of the cell composition are animal cells. In some embodiments, the cells of the composition are mammalian cells. In certain embodiments, the cells are mouse cells, hamster cells, rat cells, or non-human primate cells. In some embodiments, the cells are human cells.

In some embodiments, the cells are cells of a cell line, e.g., e Chinese hamster ovary (CHO) cells, monkey kidney CV1 line transformed by 5V40 (C057); human embryonic kidney line 293; baby hamster kidney cells (BHK); mouse sertoli cells (TM4); monkey kidney cells (CVI-76); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor cells (MMT); rat hepatoma cells (HTC); HIH/3T3 cells, and TRI cells. For an extensive list of mammalian cell lines, those of skill in the art may refer to the American Type Culture Collection catalog (ATCC, Mamassas, Va.). In some embodiments, the cells may be of a variety of cell types, e.g., fibroblasts, myoblasts, macrophages, or epithelial cells.

In particular embodiments, the cells of a composition are or include stem cells. In certain embodiments, cells of the cell composition are pluripotent stem cells, multipotent stem cells, oligopotent stem cells, and/or unipotent stem cells. In particular embodiments, the cells are induced, e.g., induced pluripotent stem cells (ipsc). In particular embodiments, the cells of the composition are cells, e.g., that are in the process of being reprogrammed, e.g., towards pluripotency. In some embodiments, the cells are stem cells are in the process of differentiation.

In some embodiments, the cells of the composition are immune cells. In particular embodiments, a cell composition contains one or more of T cells, B cells, and/or NK cells. In some embodiments the cells of the cell composition are CD3+ T cells. In some embodiments, the cells are CD4+ T cells. In certain embodiments, the cells are CD8+ T cells. In some embodiments, one or more of effector T cells, Helper T cells, cytotoxic T cells, memory T cells, and suppresser T cells. In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cell composition is or includes T cells. In particular embodiments, T cells are or include the sub-types and subpopulations of T cells such as one or more of naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In some embodiments, the cell is a regulatory T cell (Treg). In some embodiments, the cell further comprises a recombinant FOXP3 or variant thereof. In some embodiments, the cell composition is or includes CD3+ T cells. In certain embodiments, the cell composition is or includes CD4+ T cells. In certain embodiments, the cell composition is or includes CD8+ T cells.

In certain embodiments, the surface proteins of primary cells are assessed. In some embodiments, the composition of cells contains primary cells, such as those isolated directly from a subject and/or isolated from a subject and frozen. In some embodiments, the cells include one or more subsets of T cells or other cell types, such as whole T cell populations, CD4+ T cells, CD8+ T cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous.

In some embodiments, one or more cells of the composition are engineered cells. In some cases, the one or more cells are engineered to contain a recombinant nucleic acid, e.g., contain heterologous nucleic acid and/or express a heterologous protein. In some embodiments, the recombinant nucleic acid encodes a recombinant protein. In some cases, the recombinant protein can be any protein that is desired to be expressed or produced by a recombinant cell composition. In some embodiments, the recombinant protein is a recombinant receptor. In some embodiments, the recombinant nucleic acid is or includes a viral vector, e.g. lentiviral or retroviral vector, that is transferred or introduced into the cell for expression of the recombinant protein.

B. Engineered Cell Compositions

In certain embodiments, the engineered cells contain a heterologous polynucleotide that encodes a recombinant receptor. In some embodiments, the recombinant receptor is a chimeric receptor or an antigen receptor, such as a chimeric antigen receptor (CAR) or a T cell receptor (TCR). In certain embodiments, the engineered cells are produced, manufactured, or generated by any method described herein, e.g., in Section III. In certain embodiments, a mass spectrometry profile is measured, determined, or obtained from engineered cells that have been produced, manufactured, or generated from a method described herein, e.g., in Section-III In some embodiments, all or a portion of the cells in a composition contain or are engineered to contain an engineered receptor, such as a chimeric antigen receptor (CAR), or a T cell receptor (TCR). In particular embodiments, all or a portion of the cells in a composition express the engineered receptor. In some embodiments, compositions containing engineered cells are enriched for such cells. In certain embodiments, the cells of a certain type such as T cells or CD8+ or CD4+ T cells are enriched or selected. In particular embodiments, the cell composition is a therapeutic and/or a pharmaceutical cell composition, such as for adoptive cell therapy. In some embodiments, a mass spectrometry profile is measured, determined, or obtained from a therapeutic cell composition, e.g., a cell therapy. In some embodiments, a mass spectrometry profile is measured, determined, or obtained from an engineered cell composition containing CAR+ T cells.

1. Recombinant Receptors

In some embodiments, a mass spectrometry profile is measured, determined, or obtained from engineered cells, such as immune cells, such as T cells, that express one or more recombinant receptor(s). Among the receptors are antigen receptors and receptors containing one or more component thereof. The recombinant receptors may include chimeric receptors, such as those containing ligand-binding domains or binding fragments thereof and intracellular signaling domains or regions, functional non-TCR antigen receptors, chimeric antigen receptors (CARs), T cell receptors (TCRs), such as recombinant or transgenic TCRs, chimeric autoantibody receptor (CAAR) and components of any of the foregoing. The recombinant receptor, such as a CAR, generally includes the extracellular antigen (or ligand) binding domain linked to one or more intracellular signaling components, in some aspects via linkers and/or transmembrane domain(s). In some embodiments, the engineered cells express two or more receptors that contain different components, domains or regions. In some aspects, two or more receptors allows spatial or temporal regulation or control of specificity, activity, antigen (or ligand) binding, function and/or expression of the recombinant receptors.

In some embodiments, mass spectrometry profiles obtained from different cell compositions expressing the same recombinant receptor, e.g., a CAR or recombinant TCR, are compared. In certain embodiments, mass spectrometry profiles obtained from different cell compositions expressing the same recombinant receptor that were generated by the different engineering processes are compared. In some embodiments, the mass spectrometry profiles may be compared to evaluate changes in cell properties in response to different engineering processes. In some embodiments, the mass spectrometry profiles are compared to detect similarities or differences in levels or amounts of the recombinant receptor present on the cell surface. In particular embodiments, the mass spectrometry profiles are compared to detect similarities or differences in levels or amounts of post translational modifications, e.g., conjugation of glycans, to the recombinant receptor.

In some embodiments, mass spectrometry profiles obtained from different cell compositions expressing the same recombinant receptor, e.g., a CAR or recombinant TCR, are collected, such as to determine or calculate an average, median, or mean mass spectrometry profile or portion thereof. In particular embodiments, mass spectrometry profiles obtained from different cell compositions expressing the same recombinant receptor are collected, such as to determine or calculate an average, median, or mean level or amount of one or more individual proteins expressed on the surface of the cells of the compositions. In particular embodiments, mass spectrometry profiles obtained from different cell compositions expressing the same recombinant receptor are collected, to determine or calculate an average, median, or mean level or amount of one or more individual post translational modification to one or more proteins that are expressed on the cell surface. In some embodiments, the average, mean, or median mass spectrometry profile or portion thereof may serve as a reference protein profile.

In particular embodiments, mass spectrometry profiles obtained from different cell compositions expressing the same recombinant receptor, e.g., a CAR or recombinant TCR, are collected to determine or calculate the variability or variance across the mass spectrometry profiles or portions thereof. In particular embodiments, mass spectrometry profiles obtained from different cell compositions expressing the same recombinant receptor are collected to determine or calculate the variability or variance across the cell compositions for the amount of one or more individual proteins expressed on the cell surface. In some embodiments, mass spectrometry profiles obtained from different cell compositions expressing the same recombinant receptor are collected to determine or calculate the variability or variance across the cell compositions for the amount of one or more individual post translational modifications.

a. Chimeric Antigen Receptors (CARs)

In some embodiments, the engineered cells, such as T cells, express a recombinant receptor such as a chimeric antigen receptor (CAR) with specificity for a particular antigen (or marker or ligand), such as an antigen expressed on the surface of a particular cell type. In some embodiments, the antigen is a polypeptide. In some embodiments, the antigen is a carbohydrate or other molecule. In some embodiments, the antigen is selectively expressed or overexpressed on cells of the disease or condition, e.g., the tumor or pathogenic cells, as compared to normal or non-targeted cells or tissues, e.g., in healthy cells or tissues. In other embodiments, the antigen is expressed on normal cells and/or is expressed on the engineered cells. In some aspects, the recombinant receptor, e.g., a CAR, includes one or more regions or domains selected from an extracellular ligand-(e.g., antigen-) binding or regions or domains, e.g., any of the antibody or fragment described here, and in an intracellular signaling region. In some embodiments, the ligand-(e.g., antigen-) binding region or domain is or includes an scFv or a single-domain $V_H$ antibody and the intracellular signaling region or domain is or contains an ITAM. In some aspects, the intracellular signaling region or domain includes a signaling domain of a CD3-zeta (CD3ζ) chain or a portion thereof. In some aspects, the extracellular ligand- (e.g., antigen-) binding region or domain(s) and the intracellular signaling region or domain(s) are linked or connected via one or more linkers and/or transmembrane domain(s). In some embodiments, the chimeric antigen receptor includes a transmembrane domain disposed between the extracellular domain and the intracellular signaling region.

Exemplary antigen receptors, including CARs, and methods for engineering and introducing such receptors into cells, include those described, for example, in International Pat. App. Pub. International Pat. App. Pub. Nos. WO2000/14257, WO2013/126726, WO2012/129514, WO2014/031687, WO2013/166321, WO2013/071154, WO2013/123061, U.S. Pat. App. Pub. Nos. US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European Pat. App. No. EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; and Wu et al., Cancer, 2012 March 18(2): 160-75. In some aspects, the antigen receptors include a CAR as described in U.S. Pat. No. 7,446,190, and those described in International Pat. App. Pub. No. WO 2014/055668. Examples of the CARs include CARs as disclosed in any of the aforementioned references, such as WO2014/031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177).

In some embodiments, the recombinant receptor, e.g., antigen receptor contains an extracellular antigen- or ligand-binding domain that binds, e.g., specifically binds, to an antigen, a ligand and/or a marker. Among the antigen receptors are functional non-TCR antigen receptors, such as chimeric antigen receptors (CARs), In some embodiments, the antigen receptor is a CAR that contains an extracellular antigen-recognition domain that specifically binds to an antigen. In some embodiments, the CAR is constructed with a specificity for a particular antigen, marker or ligand, such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more ligand- (e.g., antigen-) binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy ($V_H$) and variable light ($V_L$) chains of a monoclonal antibody (mAb), or a single domain antibody (sdAb), such as sdFv, nanobody, $V_H$H and $V_{NAR}$. In some embodiments, an antigen-binding fragment comprises antibody variable regions joined by a flexible linker.

In some embodiments, the CAR contains an antibody or an antigen-binding fragment (e.g. scFv) that specifically recognizes an antigen or ligand, such as an intact antigen, expressed on the surface of a cell. In some embodiments, the antigen or ligand, is a protein expressed on the surface of cells. In some embodiments, the antigen or ligand is a polypeptide. In some embodiments, it is a carbohydrate or other molecule. In some embodiments, the antigen or ligand is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In some embodiments, among the antigens targeted by the chimeric receptors are those expressed in the context of a disease, condition, or cell type to be targeted via the adoptive cell therapy. Among the diseases and conditions are proliferative, neoplastic, and malignant diseases and disorders, including cancers and tumors, including hematologic cancers, cancers of the immune system, such as lymphomas, leukemias, and/or myelomas, such as B, T, and myeloid leukemias, lymphomas, and multiple myelomas.

In some embodiments, the antigen or ligand is a tumor antigen or cancer marker. In some embodiments, the antigen or ligand the antigen is or includes αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Ra), IL-13 receptor alpha 2 (IL-βRα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30. In some embodiments, the antigen is or includes a pathogen-specific or pathogen-expressed antigen, such as a viral antigen (e.g., a viral antigen from HIV, HCV, HBV), bacterial antigens, and/or parasitic antigens.

In some embodiments, the antibody or an antigen-binding fragment (e.g. scFv or $V_H$ domain) specifically recognizes an antigen, such as CD19. In some embodiments, the antibody or antigen-binding fragment is derived from, or is a variant of, antibodies or antigen-binding fragment that specifically binds to CD19.

In some embodiments the scFv and/or $V_H$ domains is derived from FMC63. FMC63 generally refers to a mouse monoclonal IgG1 antibody raised against Nalm-1 and -16 cells expressing CD19 of human origin (Ling, N. R., et al. (1987). Leucocyte typing III. 302). The FMC63 antibody comprises CDR H1 set forth in SEQ ID NO: 38; CDR H2 set forth in SEQ ID NO:39; CDR H3 set forth in SEQ ID NOS: 40 or 54; and CDR L1 set forth in SEQ ID NO: 35; CDR L2 set forth in SEQ ID NO:36 or 55; and CDR L3 set forth in SEQ ID NO:37 or 56. The FMC63 antibody comprises the heavy chain variable region ($V_H$) comprising the amino acid sequence of SEQ ID NO: 41 and the light chain variable region ($V_L$) comprising the amino acid sequence of SEQ ID NO: 42. In some embodiments, the scFv comprises a variable light chain containing a CDR L1 sequence of SEQ ID NO:35, a CDR L2 sequence of SEQ ID NO:36, and a CDR L3 sequence of SEQ ID NO:37 and/or a variable heavy chain containing a CDR H1 sequence of SEQ ID NO:38, a CDR H2 sequence of SEQ ID NO:39, and a CDR H3 sequence of SEQ ID NO:40, or a variant of any of the foregoing having at least 85%, 86%, 87%, 88%, 89%, 90%, 91%, 92%, 93%, 94%, 95%, 96%, 97%, 98%, 99% or more sequence identity thereto. In some embodiments, the scFv comprises a variable heavy chain region of FMC63 set forth in SEQ ID NO:41 and a variable light chain region of FMC63 set forth in SEQ ID NO:42, or a variant of any of the foregoing having at least 85%, 86%, 87%, 88%, 89%, 90%, 91%, 92%, 93%, 94%, 95%, 96%, 97%, 98%, 99% or more sequence identity thereto. In some embodiments, the variable heavy and variable light chains are connected by a linker. In some embodiments, the linker is set forth in SEQ ID NO:58. In some embodiments, the scFv comprises, in order, a $V_H$, a linker, and a $V_L$. In some embodiments, the scFv comprises, in order, a $V_L$, a linker, and a $V_H$. In some embodiments, the scFv is encoded by a sequence of nucleotides set forth in SEQ ID NO:57 or a sequence that exhibits at least 85%, 86%, 87%, 88%, 89%, 90%, 91%, 92%, 93%, 94%, 95%, 96%, 97%, 98%, or 99% sequence identity to SEQ ID NO:57. In some embodiments, the scFv comprises the sequence of amino acids set forth in SEQ ID NO:43 or a sequence that exhibits at least 85%, 86%, 87%, 88%, 89%, 90%, 91%, 92%, 93%, 94%, 95%, 96%, 97%, 98%, or 99% sequence identity to SEQ ID NO:43.

In some embodiments, the scFv and/or $V_H$ domain is derived from SJ25C1. SJ25C1 is a mouse monoclonal IgG1 antibody raised against Nalm-1 and -16 cells expressing CD19 of human origin (Ling, N. R., et al. (1987). Leucocyte typing III. 302). The SJ25C1 antibody comprises CDR H1, H2 and H3 set forth in SEQ ID NOS: 47-49, respectively, and CDR L1, L2 and L3 sequences set forth in SEQ ID NOS: 44-46, respectively. The SJ25C1 antibody comprises the heavy chain variable region ($V_H$) comprising the amino acid sequence of SEQ ID NO: 50 and the light chain variable region ($V_L$) comprising the amino acid sequence of SEQ ID NO: 51. In some embodiments, the svFv comprises a variable light chain containing a CDR L1 sequence set forth in SEQ ID NO:44; a CDR L2 set forth in SEQ ID NO: 45; and a CDR L3 set forth in SEQ ID NO:46; and/or a variable heavy chain containing a CDR H1 set forth in SEQ ID NO:47, a CDR H2 set forth in SEQ ID NO:48, and a CDR H3 set forth in SEQ ID NO:49, or a variant of any of the foregoing having at least 85%, 86%, 87%, 88%, 89%, 90%, 91%, 92%, 93%, 94%, 95%, 96%, 97%, 98%, 99% or more sequence identity thereto. In some embodiments, the scFv comprises a variable heavy chain region of SJ25C1 set forth in SEQ ID NO:50 and a variable light chain region of SJ25C1 set forth in SEQ ID NO:51, or a variant of any of the foregoing having at least 85%, 86%, 87%, 88%, 89%, 90%, 91%, 92%, 93%, 94%, 95%, 96%, 97%, 98%, 99% or more sequence identity thereto. In some embodiments, the variable heavy and variable light chains are connected by a linker. In some embodiments, the linker is set forth in SEQ ID NO:52. In some embodiments, the scFv comprises, in order, a $V_H$, a linker, and a $V_L$. In some embodiments, the scFv comprises, in order, a $V_L$, a linker, and a $V_H$. In some embodiments, the scFv comprises the sequence of amino acids set forth in SEQ ID NO:53 or a sequence that exhibits at least 85%, 86%, 87%, 88%, 89%, 90%, 91%, 92%, 93%, 94%, 95%, 96%, 97%, 98%, or 99% sequence identity to SEQ ID NO:53.

In some aspects, the CAR contains a ligand- (e.g., antigen-) binding domain that binds or recognizes, e.g., specifically binds, a universal tag or a universal epitope. In some aspects, the binding domain can bind a molecule, a tag, a polypeptide and/or an epitope that can be linked to a different binding molecule (e.g., antibody or antigen-binding fragment) that recognizes an antigen associated with a disease or disorder. Exemplary tag or epitope includes a dye (e.g., fluorescein isothiocyanate) or a biotin. In some aspects, a binding molecule (e.g., antibody or antigen-binding fragment) linked to a tag, that recognizes the antigen associated with a disease or disorder, e.g., tumor antigen, with an engineered cell expressing a CAR specific for the tag, to effect cytotoxicity or other effector function of the engineered cell. In some aspects, the specificity of the CAR to the antigen associated with a disease or disorder is provided by the tagged binding molecule (e.g., antibody), and different tagged binding molecule can be used to target different antigens. Exemplary CARs specific for a universal tag or a universal epitope include those described, e.g., in U.S. Pat. No. 9,233,125, WO 2016/030414, Urbanska et al., (2012) Cancer Res 72: 1844-1852, and Tamada et al., (2012). Clin Cancer Res 18:6436-6445.

In some embodiments, the CAR contains a TCR-like antibody, such as an antibody or an antigen-binding fragment (e.g. scFv) that specifically recognizes an intracellular antigen, such as a tumor-associated antigen, presented on the cell surface as a major histocompatibility complex (MHC)-peptide complex. In some embodiments, an antibody or antigen-binding portion thereof that recognizes an MHC-peptide complex can be expressed on cells as part of a recombinant receptor, such as an antigen receptor. Among the antigen receptors are functional non-T cell receptor (TCR) antigen receptors, such as chimeric antigen receptors (CARs). In some embodiments, a CAR containing an antibody or antigen-binding fragment that exhibits TCR-like specificity directed against peptide-MHC complexes also may be referred to as a TCR-like CAR. In some embodiments, the CAR is a TCR-like CAR and the antigen is a processed peptide antigen, such as a peptide antigen of an intracellular protein, which, like a TCR, is recognized on the cell surface in the context of an MHC molecule. In some embodiments, the extracellular antigen-binding domain specific for an MHC-peptide complex of a TCR-like CAR is linked to one or more intracellular signaling components, in some aspects via linkers and/or transmembrane domain(s). In some embodiments, such molecules can typically mimic or approximate a signal through a natural antigen receptor, such as a TCR, and, optionally, a signal through such a receptor in combination with a costimulatory receptor.

Reference to "Major histocompatibility complex" (MHC) refers to a protein, generally a glycoprotein, that contains a polymorphic peptide binding site or binding groove that can, in some cases, complex with peptide antigens of polypeptides, including peptide antigens processed by the cell machinery. In some cases, MHC molecules can be displayed or expressed on the cell surface, including as a complex with peptide, i.e. MHC-peptide complex, for presentation of an antigen in a conformation recognizable by an antigen receptor on T cells, such as a TCRs or TCR-like antibody. Generally, MHC class I molecules are heterodimers having a membrane spanning a chain, in some cases with three a domains, and a non-covalently associated β2 microglobulin. Generally, MHC class II molecules are composed of two transmembrane glycoproteins, α and β, both of which typically span the membrane. An MHC molecule can include an effective portion of an MHC that contains an antigen binding site or sites for binding a peptide and the sequences necessary for recognition by the appropriate antigen receptor. In some embodiments, MHC class I molecules deliver peptides originating in the cytosol to the cell surface, where a MHC-peptide complex is recognized by T cells, such as generally CD8$^+$ T cells, but in some cases CD4$^+$ T cells. In some embodiments, MHC class II molecules deliver peptides originating in the vesicular system to the cell surface, where they are typically recognized by CD4$^+$ T cells. Generally, MHC molecules are encoded by a group of linked loci, which are collectively termed H-2 in the mouse and human leukocyte antigen (HLA) in humans. Hence, typically human MHC can also be referred to as human leukocyte antigen (HLA).

The term "MHC-peptide complex" or "peptide-MHC complex" or variations thereof, refers to a complex or association of a peptide antigen and an MHC molecule, such as, generally, by non-covalent interactions of the peptide in the binding groove or cleft of the MHC molecule. In some embodiments, the MHC-peptide complex is present or displayed on the surface of cells. In some embodiments, the MHC-peptide complex can be specifically recognized by an antigen receptor, such as a TCR, TCR-like CAR or antigen-binding portions thereof.

In some embodiments, a peptide, such as a peptide antigen or epitope, of a polypeptide can associate with an MHC molecule, such as for recognition by an antigen receptor. Generally, the peptide is derived from or based on a fragment of a longer biological molecule, such as a polypeptide or protein. In some embodiments, the peptide typically is about 8 to about 24 amino acids in length. In some embodiments, a peptide has a length of from or from about 9 to 22 amino acids for recognition in the MHC Class II complex. In some embodiments, a peptide has a length of from or from about 8 to 13 amino acids for recognition in the MHC Class I complex. In some embodiments, upon recognition of the peptide in the context of an MHC molecule, such as MHC-peptide complex, the antigen receptor, such as TCR or TCR-like CAR, produces or triggers an activation signal to the T cell that induces a T cell response, such as T cell proliferation, cytokine production, a cytotoxic T cell response or other response.

In some embodiments, a TCR-like antibody or antigen-binding portion, are known or can be produced by known methods (see e.g. US Published Application Nos. US 2002/0150914; US 2003/0223994; US 2004/0191260; US 2006/0034850; US 2007/00992530; US20090226474; US20090304679; and International App. Pub. No. WO 03/068201).

In some embodiments, an antibody or antigen-binding portion thereof that specifically binds to a MHC-peptide complex, can be produced by immunizing a host with an effective amount of an immunogen containing a specific MHC-peptide complex. In some cases, the peptide of the MHC-peptide complex is an epitope of antigen capable of binding to the MHC, such as a tumor antigen, for example a universal tumor antigen, myeloma antigen or other antigen as described below. In some embodiments, an effective amount of the immunogen is then administered to a host for eliciting an immune response, wherein the immunogen retains a three-dimensional form thereof for a period of time sufficient to elicit an immune response against the three-dimensional presentation of the peptide in the binding groove of the MHC molecule. Serum collected from the host is then assayed to determine if desired antibodies that recognize a three-dimensional presentation of the peptide in the binding groove of the MHC molecule is being produced. In some embodiments, the produced antibodies can be assessed to confirm that the antibody can differentiate the MHC-peptide complex from the MHC molecule alone, the peptide of interest alone, and a complex of MHC and irrelevant peptide. The desired antibodies can then be isolated.

In some embodiments, an antibody or antigen-binding portion thereof that specifically binds to an MHC-peptide complex can be produced by employing antibody library display methods, such as phage antibody libraries. In some embodiments, phage display libraries of mutant Fab, scFv or other antibody forms can be generated, for example, in which members of the library are mutated at one or more residues of a CDR or CDRs. See e.g. US Pat. App. Pub. No. US20020150914, US20140294841; and Cohen CJ. et al. (2003) *J Mol. Recogn.* 16:324-332.

The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, variable heavy chain (V$_H$) regions capable of specifically binding the antigen, single chain antibody fragments, including single chain variable fragments (scFv), and single domain antibodies (e.g., sdAb, sdFv, nanobody, V$_H$H or V$_{NAR}$) or fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD. In some aspects, the CAR is a bispecific CAR, e.g., containing two antigen-binding domains with different specificities.

In some embodiments, the antigen-binding proteins, antibodies and antigen binding fragments thereof specifically recognize an antigen of a full-length antibody. In some embodiments, the heavy and light chains of an antibody can be full-length or can be an antigen-binding portion (a Fab, F(ab')2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; variable heavy chain ($V_H$) regions, single-chain antibody molecules such as scFvs and single-domain $V_H$ single antibodies; and multispecific antibodies formed from antibody fragments. In particular embodiments, the antibodies are single-chain antibody fragments comprising a variable heavy chain region and/or a variable light chain region, such as scFvs.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Single-domain antibodies (sdAb) are antibody fragments comprising all or a portion of the heavy chain variable domain or all or a portion of the light chain variable domain of an antibody. In certain embodiments, a single-domain antibody is a human single-domain antibody. In some embodiments, the CAR comprises an antibody heavy chain domain that specifically binds the antigen, such as a cancer marker or cell surface antigen of a cell or disease to be targeted, such as a tumor cell or a cancer cell, such as any of the target antigens described herein or known. Exemplary single-domain antibodies include sdFv, nanobody, $V_H$H or $V_{NAR}$.

Antibody fragments can be made by various techniques, including but not limited to proteolytic digestion of an intact antibody as well as production by recombinant host cells. In some embodiments, the antibodies are recombinantly produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some embodiments, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Thus, in some embodiments, the chimeric antigen receptor, including TCR-like CARs, includes an extracellular portion containing an antibody or antibody fragment. In some embodiments, the antibody or fragment includes an scFv. In some aspects, the antibody or antigen-binding fragment can be obtained by screening a plurality, such as a library, of antigen-binding fragments or molecules, such as by screening an scFv library for binding to a specific antigen or ligand.

In some aspects, the recombinant receptor, e.g., a chimeric antigen receptor, includes an extracellular portion containing one or more ligand- (e.g., antigen-) binding domains, such as an antibody or fragment thereof, and one or more intracellular signaling region or domain (also interchangeably called a cytoplasmic signaling domain or region). In some aspects, the recombinant receptor, e.g., CAR, further includes a spacer and/or a transmembrane domain or portion. In some aspects, the spacer and/or transmembrane domain can link the extracellular portion containing the ligand- (e.g., antigen-) binding domain and the intracellular signaling region(s) or domain(s).

In some embodiments, the recombinant receptor such as the CAR further includes a spacer, which may be or include at least a portion of an immunoglobulin constant region or variant or modified version thereof, such as a hinge region, e.g., an IgG4 hinge region, and/or a $C_H1/C_L$ and/or Fc region. In some embodiments, the recombinant receptor further comprises a spacer and/or a hinge region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. In some embodiments, the spacer is less than 250 amino acids in length, less than 200 amino acids in length, less than 150 amino acids in length, less than 100 amino acids in length, less than 75 amino acids in length, less than 50 amino acids in length, less than 25 amino acids in length, less than 20 amino acids in length, less than 15 amino acids in length, less than 12 amino acids in length, or less than 10 amino acids in length. In some embodiments, the spacer is from or from about 10 to 250 amino acids in length, 10 to 150 amino acids in length, 10 to 100 amino acids in length, 10 to 50 amino acids in length, 10 to 25 amino acids in length, 10 to 15 amino acids in length, 15 to 250 amino acids in length, 15 to 150 amino acids in length, 15 to 100 amino acids in length, 15 to 50 amino acids in length, 15 to 25 amino acids in length, 25 to 250 amino acids in length, 25 to 100 amino acids in length, 25 to 50 amino acids in length, 50 to 250 amino acids in length, 50 to 150 amino acids in length, 50 to 100 amino acids in length, 100 to 250 amino acids in length, 100 to 150 amino acids in length, or 150 to 250 amino acids in length. Exemplary spacers include IgG4 hinge alone, IgG4 hinge linked to $C_H2$ and $C_H3$ domains, or IgG4 hinge linked to the $C_H3$ domain. Exemplary spacers include, but are not limited to, those described in Hudecek et al. (2013) Clin. Cancer Res., 19:3153, Hudecek et al. (2015) Cancer Immunol Res. 3(2): 125-135 or International Pat. App. Pub. No. WO2014031687.

In some aspects, the spacer contains only a hinge region of an IgG, such as only a hinge of IgG4 or IgG1, such as the hinge only spacer set forth in SEQ ID NO:1, and is encoded by the sequence set forth in SEQ ID NO: 2. In other embodiments, the spacer is an Ig hinge, e.g., and IgG4 hinge, linked to a $C_H2$ and/or $C_H3$ domains. In some embodiments, the spacer is an Ig hinge, e.g., an IgG4 hinge, linked to $C_H2$ and $C_H3$ domains, such as set forth in SEQ ID NO:4. In some embodiments, the spacer is an Ig hinge, e.g., an IgG4 hinge, linked to a $C_H3$ domain only, such as set forth in SEQ ID NO:3. In some embodiments, the spacer is or comprises a glycine-serine rich sequence or other flexible linker such as known flexible linkers. In some embodiments, the constant region or portion is of IgD. In some embodiments, the spacer has the sequence set forth in SEQ ID NO: 5. In some embodiments, the spacer has a sequence of amino acids that exhibits at least or at least about 85%, 86%, 87%, 88%, 89%, 90%, 91%, 92%, 93%, 94%, 95%, 96%, 97%, 98%, 99% or more sequence identity to any of SEQ ID NOS: 1, 3, 4 and 5.

In some embodiments, the spacer can be derived all or in part from IgG4 and/or IgG2. In some embodiments, the spacer can be a chimeric polypeptide containing one or more of a hinge, $C_H2$ and/or $C_H3$ sequence(s) derived from IgG4, IgG2, and/or IgG2 and IgG4. In some embodiments, the spacer can contain mutations, such as one or more single amino acid mutations in one or more domains. In some examples, the amino acid modification is a substitution of a proline (P) for a serine (S) in the hinge region of an IgG4. In some embodiments, the amino acid modification is a substitution of a glutamine (Q) for an asparagine (N) to reduce glycosylation heterogeneity, such as an N to Q substitution at a position corresponding to position 177 in the $C_H2$ region of the IgG4 heavy chain constant region sequence set forth in SEQ ID NO: 60 (Uniprot Accession No. P01861; position corresponding to position 297 by EU numbering and position 79 of the hinge-$C_H2$-$C_H3$ spacer sequence set forth in SEQ ID NO:4) or an N to Q substitution at a position corresponding to position 176 in the $C_H2$ region of the IgG2 heavy chain constant region sequence set forth in SEQ ID NO: 59 (Uniprot Accession No. P01859; position corresponding to position 297 by EU numbering).

In some aspects, the spacer is a polypeptide spacer such as one or more selected from: (a) comprises or consists of all or a portion of an immunoglobulin hinge or a modified version thereof or comprises about 15 amino acids or less, and does not comprise a CD28 extracellular region or a CD8 extracellular region, (b) comprises or consists of all or a portion of an immunoglobulin hinge, optionally an IgG4 hinge, or a modified version thereof and/or comprises about 15 amino acids or less, and does not comprise a CD28 extracellular region or a CD8 extracellular region, or (c) is at or about 12 amino acids in length and/or comprises or consists of all or a portion of an immunoglobulin hinge, optionally an IgG4, or a modified version thereof; or (d) consists or comprises the sequence of amino acids set forth in SEQ ID NOS: 1, 3-5 or 27-34, or a variant of any of the foregoing having at least 85%, 86%, 87%, 88%, 89%, 90%, 91%, 92%, 93%, 94%, 95%, 96%, 97%, 98%, 99% or more sequence identity thereto, or (e) comprises or consists of the formula $X_1PPX_2P$, where $X_1$ is glycine, cysteine or arginine and $X_2$ is cysteine or threonine.

In some embodiments, the ligand- (e.g., antigen-) binding or recognition domain of the CAR is linked to one or more intracellular signaling components, such as an intracellular signaling region or domain, and/or signaling components that mimic activation through an antigen receptor complex, such as a TCR complex, and/or signal via another cell surface receptor. Thus, in some embodiments, the antigen binding component (e.g., antibody) is linked to one or more transmembrane and intracellular signaling region(s) or domain(s). In some embodiments, the transmembrane domain is fused to the extracellular domain. In some embodiments, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e., comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 (4-1BB), or CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s). In some aspects, the transmembrane domain contains a transmembrane portion of CD28 or a variant thereof. The extracellular domain and transmembrane can be linked directly or indirectly. In some embodiments, the extracellular domain and transmembrane are linked by a spacer, such as any described herein.

In some embodiments, the transmembrane domain of the receptor, e.g., the CAR is a transmembrane domain of human CD28 or variant thereof, e.g., a 27-amino acid transmembrane domain of a human CD28 (Accession No.: P10747.1), or is a transmembrane domain that comprises the sequence of amino acids set forth in SEQ ID NO: 8 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO:8; in some embodiments, the transmembrane-domain containing portion of the recombinant receptor comprises the sequence of amino acids set forth in SEQ ID NO: 9 or a sequence of amino acids having at least or at least about 85%, 86%, 87%, 88%, 89%, 90%, 91%, 92%, 93%, 94%, 95%, 96%, 97%, 98%, 99% or more sequence identity thereto.

In some aspects, the recombinant receptor, e.g., CAR, includes an intracellular signaling region or domain (also interchangeably called a cytoplasmic signaling domain or region). In some embodiments, the intracellular signaling region comprises an intracellular signaling domain. In some embodiments, the intracellular signaling region or domain is or comprises a primary signaling domain, a signaling domain that is capable of stimulating and/or inducing a primary activation signal in a T cell, a signaling domain of a T cell receptor (TCR) component (e.g. an intracellular signaling domain or region of a CD3-zeta (CD3) chain or a functional variant or signaling portion thereof), and/or a signaling domain comprising an immunoreceptor tyrosine-based activation motif (ITAM). In some embodiments, the recombinant receptor, e.g., CAR, includes an extracellular portion containing the antibody or fragment and an intracellular signaling region or domain.

In some embodiments, the recombinant receptor, e.g., CAR, includes at least one intracellular signaling component or components, such as an intracellular signaling region or domain Among the intracellular signaling region are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

In some embodiments, upon ligation of the CAR, the cytoplasmic domain or intracellular signaling region of the CAR stimulates and/or activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling region or domain of an antigen receptor component or costimulatory molecule is used in place of an intact immunostimulatory chain, for example, if it transduces the effector function signal. In some embodiments, the intracellular signaling regions, e.g., comprising intracellular domain or domains, include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability. In some embodiments, the intracellular signaling regions, e.g., comprising intracellular domain or domains, include the cytoplasmic sequences of a region or domain that is involved in providing costimulatory signal.

In some embodiments, the receptor includes an intracellular component of a TCR complex, such as a TCR CD3 chain that mediates T-cell activation and cytotoxicity, e.g., CD3 zeta chain. Thus, in some aspects, the antigen-binding or antigen-recognition domain is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor gamma (FcR γ), CD8 alpha, CD8 beta, CD4, CD25, or CD16. For example, in some aspects, the CAR includes a chimeric molecule between CD3 zeta (CD3) or FcR γ and one or more of CD8 alpha, CD8 beta, CD4, CD25 or CD16.

In the context of a natural TCR, full activation generally requires not only signaling through the TCR, but also a costimulatory signal. T cell activation is in some aspects described as being mediated by two classes of cytoplasmic signaling sequences: those that initiate antigen-dependent primary activation through the TCR (primary cytoplasmic signaling region(s) or domain(s)), and those that act in an antigen-independent manner to provide a secondary or co-stimulatory signal (secondary cytoplasmic signaling region(s) or domain(s)). In some aspects, the CAR includes one or both of such signaling components.

In some aspects, the CAR includes a primary cytoplasmic signaling region that regulates primary stimulation and/or activation of the TCR complex. Primary cytoplasmic signaling region(s) that act in a stimulatory manner may contain signaling motifs which are known as immunoreceptor tyrosine-based activation motifs or ITAMs. Examples of ITAM containing primary cytoplasmic signaling region(s) include those derived from TCR or CD3 zeta (CD3), Fc receptor (FcR) gamma or FcR beta. In some embodiments, cytoplasmic signaling regions or domains in the CAR contain(s) a cytoplasmic signaling domain, portion thereof, or sequence derived from CD3 zeta. In some embodiments, the intracellular (or cytoplasmic) signaling region comprises a human CD3 chain, optionally a CD3 zeta stimulatory signaling domain or functional variant thereof, such as an 112 AA cytoplasmic domain of isoform 3 of human CD3 (Accession No.: P20963.2) or a CD3 zeta signaling domain as described in U.S. Pat. No. 7,446,190 or 8,911,993. In some embodiments, the intracellular signaling region comprises the sequence of amino acids set forth in SEQ ID NO: 13, 14 or 15 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 13, 14 or 15.

Thus, in some embodiments, to promote full stimulation and/or activation, one or more components for generating secondary or costimulatory signal is also included in the CAR. In other embodiments, the CAR does not include a component for generating a costimulatory signal. In some aspects, an additional CAR is expressed in the same cell and provides the component for generating the secondary or costimulatory signal.

In some embodiments, the CAR includes a signaling region and/or transmembrane portion of a costimulatory receptor, such as CD28, 4-1BB, OX40 (CD134), CD27, DAP10, DAP12, ICOS and/or other costimulatory receptors. In some aspects, the same CAR includes both the primary cytoplasmic signaling region and costimulatory signaling components.

In some embodiments, one or more different recombinant receptors can contain one or more different intracellular signaling region(s) or domain(s). In some embodiments, the primary cytoplasmic signaling region is included within one CAR, whereas the costimulatory component is provided by another receptor, e.g., another CAR recognizing another antigen. In some embodiments, the CARs include activating or stimulatory CARs, and costimulatory CARs, both expressed on the same cell (see WO2014/055668).

In certain embodiments, the intracellular signaling region comprises a CD28 transmembrane and signaling domain linked to a CD3 (e.g., CD3 zeta) intracellular domain. In some embodiments, the intracellular signaling region comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and primary cytoplasmic signaling region, in the cytoplasmic portion. Exemplary CARs include intracellular components, such as intracellular signaling region(s) or domain(s), of CD3-zeta, CD28, CD137 (4-1BB), OX40 (CD134), CD27, DAP10, DAP12, NKG2D and/or ICOS. In some embodiments, the chimeric antigen receptor contains an intracellular signaling region or domain of a T cell costimulatory molecule, e.g., from CD28, CD137 (4-1BB), OX40 (CD134), CD27, DAP10, DAP12, NKG2D and/or ICOS, in some cases, between the transmembrane domain and intracellular signaling region or domain. In some aspects, the T cell costimulatory molecule is one or more of CD28, CD137 (4-1BB), OX40 (CD134), CD27, DAP10, DAP12, NKG2D and/or ICOS.

In some embodiments, the intracellular signaling region or domain comprises an intracellular costimulatory signaling domain of human CD28 or functional variant or portion thereof, such as a 41 amino acid domain thereof and/or such a domain with an LL to GG substitution at positions 186-187 of a native CD28 protein. In some embodiments, the intracellular signaling domain can comprise the sequence of amino acids set forth in SEQ ID NO: 10 or 11 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 10 or 11. In some embodiments, the intracellular region comprises an intracellular costimulatory signaling region or domain of CD137(4-1BB) or functional variant or portion thereof, such as a 42-amino acid cytoplasmic domain of a human 4-1BB (Accession No. Q07011.1) or functional variant or portion thereof, such as the sequence of amino acids set forth in SEQ ID NO: 12 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 12.

In some cases, CARs are referred to as first, second, third or fourth generation CARs. In some aspects, a first generation CAR is one that solely provides a primary stimulation or activation signal, e.g., via CD3-chain induced signal upon antigen binding; in some aspects, a second-generation CAR is one that provides such a signal and costimulatory signal, such as one including an intracellular signaling region(s) or domain(s) from one or more costimulatory receptor such as CD28, CD137 (4-1BB), OX40 (CD134), CD27, DAP10, DAP12, NKG2D, ICOS and/or other costimulatory receptors; in some aspects, a third generation CAR is one that includes multiple costimulatory domains of different costimulatory receptors, e.g., selected from CD28, CD137 (4-1BB), OX40 (CD134), CD27, DAP10, DAP12, NKG2D, ICOS and/or other costimulatory receptors; in some aspects, a fourth generation CAR is one that includes three or more costimulatory domains of different costimulatory receptors, e.g., selected from CD28, CD137 (4-1BB), OX40 (CD134), CD27, DAP10, DAP12, NKG2D, ICOS and/or other costimulatory receptors.

In some embodiments, the cell is engineered to express one or more additional molecules and/or polypeptides and/or combinatorial and/or multiple-targeting approaches are used to regulate, control, or modulate function and/or activity of the CAR. Exemplary approaches employed for CARs and combinatorial approaches are described, e.g., in the combinatorial approaches and multi-targeting section described below.

In some embodiments, the CAR contains an antibody, e.g., an antibody fragment, a transmembrane domain that is or contains a transmembrane portion of CD28 or a functional variant thereof, and an intracellular signaling region containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

b. Chimeric Auto-Antibody Receptor (CAAR)

In some embodiments, the recombinant receptor is a chimeric autoantibody receptor (CAAR). In some embodiments, the CAAR binds, e.g., specifically binds, or recognizes, an autoantibody. In some embodiments, a cell expressing the CAAR, such as a T cell engineered to express a CAAR, can be used to bind to and kill autoantibody-expressing cells, but not normal antibody expressing cells. In some embodiments, CAAR-expressing cells can be used to treat an autoimmune disease associated with expression of self-antigens, such as autoimmune diseases. In some embodiments, CAAR-expressing cells can target B cells that ultimately produce the autoantibodies and display the autoantibodies on their cell surfaces, mark these B cells as disease-specific targets for therapeutic intervention. In some embodiments, CAAR-expressing cells can be used to efficiently targeting and killing the pathogenic B cells in autoimmune diseases by targeting the disease-causing B cells using an antigen-specific chimeric autoantibody receptor. In some embodiments, the recombinant receptor is a CAAR, such as any described in U.S. Patent Application Pub. No. US 2017/0051035.

In some embodiments, the CAAR comprises an autoantibody binding domain, a transmembrane domain, and one or more intracellular signaling region or domain (also interchangeably called a cytoplasmic signaling domain or region). In some embodiments, the intracellular signaling region comprises an intracellular signaling domain. In some embodiments, the intracellular signaling domain is or comprises a primary signaling domain, a signaling domain that is capable of stimulating and/or inducing a primary activation signal in a T cell, a signaling domain of a T cell receptor (TCR) component (e.g. an intracellular signaling domain or region of a CD3-zeta (CD3) chain or a functional variant or signaling portion thereof), and/or a signaling domain comprising an immunoreceptor tyrosine-based activation motif (ITAM).

In some embodiments, the autoantibody binding domain comprises an autoantigen or a fragment thereof. The choice of autoantigen can depend upon the type of autoantibody being targeted. For example, the autoantigen may be chosen because it recognizes an autoantibody on a target cell, such as a B cell, associated with a particular disease state, e.g. an autoimmune disease, such as an autoantibody-mediated autoimmune disease. In some embodiments, the autoimmune disease includes pemphigus vulgaris (PV). Exemplary autoantigens include desmoglein 1 (Dsg1) and Dsg3.

c. T Cell Receptors (TCRs)

In some embodiments, engineered cells, such as T cells, express a T cell receptor (TCR) or antigen-binding portion thereof that recognizes an intracellular and/or a peptide epitope or T cell epitope of a target polypeptide, such as an antigen of a tumor, viral or autoimmune protein. In some aspects, the recombinant receptor is or includes a recombinant TCR.

In some embodiments, a "T cell receptor" or "TCR" is a molecule that contains a variable α and β chains (also known as TCRα and TCRβ, respectively) or a variable γ and δ chains (also known as TCRα and TCRβ, respectively), or antigen-binding portions thereof, and which is capable of specifically binding to a peptide bound to an MHC molecule. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α ($V_α$) chain and variable β ($V_β$) chain of a TCR, or antigen-binding fragments thereof sufficient to form a binding site for binding to a specific MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., Immunobiology: The Immune System in Health and Disease, 3rd Ed., Current Biology Publications, p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Vα or Vβ; typically amino acids 1 to 116 based on Kabat numbering Kabat et al., "Sequences of Proteins of Immunological Interest, US Dept. Health and Human Services, Public Health Service National Institutes of Health, 1991, 5th ed.) and a constant domain (e.g., α-chain constant domain or $C_α$, typically positions 117 to 259 of the chain based on Kabat numbering or β chain constant domain or $C_β$, typically positions 117 to 295 of the chain based on Kabat) adjacent to the cell membrane. For example, in some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ζ chains) contain one or more immunoreceptor tyrosine-based activation motif or ITAM that are involved in the signaling capacity of the TCR complex.

In some embodiments, the TCR contains various domains or regions. In some cases, the exact domain or region can vary depending on the particular structural or homology modeling or other features used to describe a particular domain. It is understood that reference to amino acids, including to a specific sequence set forth as a SEQ ID NO used to describe domain organization of a recombinant receptor, e.g., TCR, are for illustrative purposes and are not meant to limit the scope of the embodiments provided. In some cases, the specific domain (e.g. variable or constant) can be several amino acids (such as one, two, three or four) longer or shorter. In some aspects, residues of a TCR are known or can be identified according to the International Immunogenetics Information System (IMGT) numbering system (see e.g. www.imgt.org; see also, Lefranc et al. (2003) Developmental and Comparative Immunology, 2&; 55-77; and The T Cell Factsbook 2nd Edition, Lefranc and LeFranc Academic Press 2001). Using this system, the CDR1 sequences within a TCR Vα chains and/or Vβ chain correspond to the amino acids present between residue numbers 27-38, inclusive, the CDR2 sequences within a TCR Vα chain and/or Vβ chain correspond to the amino acids present between residue numbers 56-65, inclusive, and the CDR3 sequences within a TCR Vα chain and/or Vβ chain correspond to the amino acids present between residue numbers 105-117, inclusive.

In some embodiments, the α chain and β chain of a TCR each further contain a constant domain. In some embodiments, the α chain constant domain (Cα) and β chain constant domain (Cβ) individually are mammalian, such as is a human or murine constant domain. In some embodiments, the constant domain is adjacent to the cell membrane. For example, in some cases, the extracellular portion of the TCR formed by the two chains contains two membrane-proximal constant domains, and two membrane-distal variable domains, which variable domains each contain CDRs.

In some embodiments, each of the Cα and Cβ domains is human. In some embodiments, the Cα is encoded by the TRAC gene (IMGT nomenclature) or is a variant thereof. In some embodiments, the Cβ is encoded by TRBC1 or TRBC2 genes (IMGT nomenclature) or is a variant thereof. In some embodiments, any of the provided TCRs or antigen-binding fragments thereof can be a human/mouse chimeric TCR. In some cases, the TCR or antigen-binding fragment thereof have α chain and/or αβ chain comprising a mouse constant region. In some aspects, the Cα and/or Cβ regions are mouse constant regions. In some of any such embodiments, the TCR or antigen-binding fragment thereof is encoded by a nucleotide sequence that has been codon-optimized.

In some of any such embodiments, the binding molecule or TCR or antigen-binding fragment thereof is isolated or purified or is recombinant. In some of any such embodiments, the binding molecule or TCR or antigen-binding fragment thereof is human.

In some embodiments, the TCR may be a heterodimer of two chains α and β that are linked, such as by a disulfide bond or disulfide bonds. In some embodiments, the constant domain of the TCR may contain short connecting sequences in which a cysteine residue forms a disulfide bond, thereby linking the two chains of the TCR. In some embodiments, a TCR may have an additional cysteine residue in each of the α β and chains, such that the TCR contains two disulfide bonds in the constant domains. In some embodiments, each of the constant and variable domains contains disulfide bonds formed by cysteine residues.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the recombinant receptors include recombinant TCRs and/or TCRs cloned from naturally occurring T cells. In some embodiments, a high-affinity T cell clone for a target antigen (e.g., a cancer antigen) is identified, isolated from a patient, and introduced into the cells. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) Clin Cancer Res. 15:169-180 and Cohen et al. (2005) J Immunol. 175:5799-5808. In some embodiments, phage display is used to isolate TCRs against a target antigen (see, e.g., Varela-Rohena et al. (2008) Nat Med. 14:1390-1395 and Li (2005) Nat Biotechnol. 23:349-354.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T-cells can be a cultured T-cell hybridoma or clone. In some embodiments, the TCR or antigen-binding portion thereof or antigen-binding fragment thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Vα and Vβ from T cells isolated from a subject, including cells present in PBMCs, spleen or other lymphoid organ. In some cases, T cells can be amplified from tumor-infiltrating lymphocytes (TILs). In some embodiments, TCR libraries can be generated from CD4+ or CD8+ cells. In some embodiments, the TCRs can be amplified from a T cell source of a normal of healthy subject, i.e. normal TCR libraries. In some embodiments, the TCRs can be amplified from a T cell source of a diseased subject, i.e., diseased TCR libraries. In some embodiments, degenerate primers are used to amplify the gene repertoire of Vα and Vβ, such as by RT-PCR in samples, such as T cells, obtained from humans. In some embodiments, libraries, such as single-chain TCR (scTv) libraries, can be assembled from naïve Vα and Vβ libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule.

In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) Nat Immunol, 4, 55-62; Holler et al. (2000)

Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments, the antigen is a tumor antigen that can be a glioma-associated antigen, β-human chorionic gonadotropin, alphafetoprotein (AFP), B-cell maturation antigen (BCMA, BCM), B-cell activating factor receptor (BAFFR, BR3), and/or transmembrane activator and CAML interactor (TACI), Fe Receptor-like 5 (FCRL5, FcRH5), lectin-reactive AFP, thyroglobulin, RAGE-1, MN-CA IX, human telomerase reverse transcriptase, RU1, RU2 (AS), intestinal carboxyl esterase, mut hsp70-2, M-CSF, Melanin-A/MART-1, WT-1, S-100, MBP, CD63, MUC1 (e.g. MUC1-8), p53, Ras, cyclin B1, HER-2/neu, carcinoembryonic antigen (CEA), gp100, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A11, MAGE-B1, MAGE-B2, MAGE-B3, MAGE-B4, MAGE-C1, BAGE, GAGE-1, GAGE-2, p15, tyrosinase, tyrosinase-related protein 1 (TRP-1), tyrosinase-related protein 2 (TRP-2), β-catenin, NY-ESO-1, LAGE-1a, PP1, MDM2, MDM4, EGVFvIII, Tax, SSX2, telomerase, TARP, pp65, CDK4, vimentin, 5100, eIF-4A1, IFN-inducible p'78, and melanotransferrin (p9'7), Uroplakin II, prostate specific antigen (PSA), human kallikrein (huK2), prostate specific membrane antigen (PSM), and prostatic acid phosphatase (PAP), neutrophil elastase, ephrin B2, BA-46, beta-catenin, Bcr-abl, E2A-PRL, H4-RET, IGH-IGK, MYL-RAR, Caspase 8 or a B-Raf antigen. Other tumor antigens can include any derived from FRa, CD24, CD44, CD133, CD 166, epCAM, CA-125, HE4, Oval, estrogen receptor, progesterone receptor, uPA, PAI-1, CD19, CD20, CD22, ROR1, mesothelin, CD33/IL3Ra, c-Met, PSMA, Glycolipid F77, GD-2, insulin growth factor (IGF)-I, IGF-II and IGF-I receptor. Specific tumor-associated antigens or T cell epitopes are known (see e.g. van der Bruggen et al. (2013) Cancer Immun, available at www.cancerimmunity.org/peptide/; Cheever et al. (2009) Clin Cancer Res, 15, 5323-37).

In some embodiments, the antigen is a viral antigen. Many viral antigen targets have been identified and are known, including peptides derived from viral genomes in HIV, HTLV and other viruses (see e.g., Addo et al. (2007) PLoS ONE, 2, e321; Tsomides et al. (1994) J Exp Med, 180, 1283-93; Utz et al. (1996) J Virol, 70, 843-51). Exemplary viral antigens include, but are not limited to, an antigen from hepatitis A, hepatitis B (e.g., HBV core and surface antigens (HBVc, HBVs)), hepatitis C (HCV), Epstein-Barr virus (e.g. EBVA), human papillomavirus (HPV; e.g. E6 and E7), human immunodeficiency type-1 virus (HIV1), Kaposi's sarcoma herpes virus (KSHV), human papilloma virus (HPV), influenza virus, Lassa virus, HTLN-1, HIN-1, HIN-II, CMN, EBN or HPN. In some embodiments, the target protein is a bacterial antigen or other pathogenic antigen, such as Mycobacterium tuberculosis (MT) antigens, trypanosome, e.g., Trypansoma cruzi (T. cruzi), antigens such as surface antigen (TSA), or malaria antigens. Specific viral antigen or epitopes or other pathogenic antigens or T cell epitopes are known (see e.g., Addo et al. (2007) PLoS ONE, 2:e321; Anikeeva et al. (2009) Clin Immunol, 130:98-109).

In some embodiments, the antigen is an antigen derived from a virus associated with cancer, such as an oncogenic virus. For example, an oncogenic virus is one in which infection from certain viruses are known to lead to the development of different types of cancers, for example, hepatitis A, hepatitis B (e.g., HBV core and surface antigens (HBVc, HBVs)), hepatitis C (HCV), human papilloma virus (HPV), hepatitis viral infections, Epstein-Barr virus (EBV), human herpes virus 8 (HHV-8), human T-cell leukemia virus-1 (HTLV-1), human T-cell leukemia virus-2 (HTLV-2), or a cytomegalovirus (CMV) antigen.

In some embodiments, the viral antigen is an HPV antigen, which, in some cases, can lead to a greater risk of developing cervical cancer. In some embodiments, the antigen can be a HPV-16 antigen, and HPV-18 antigen, and HPV-31 antigen, an HPV-33 antigen or an HPV-35 antigen. In some embodiments, the viral antigen is an HPV-16 antigen (e.g., seroreactive regions of the E1, E2, E6 and/or E7 proteins of HPV-16, see e.g., U.S. Pat. No. 6,531,127) or an HPV-18 antigen (e.g., seroreactive regions of the L1 and/or L2 proteins of HPV-18, such as described in U.S. Pat. No. 5,840,306). In some embodiments, the viral antigen is an HPV-16 antigen that is from the E6 and/or E7 proteins of HPV-16. In some embodiments, the TCR is a TCR directed against an HPV-16 E6 or HPV-16 E7. In some embodiments, the TCR is a TCR described in, e.g., WO 2015/184228, WO 2015/009604 and WO 2015/009606.

In some embodiments, the viral antigen is a HBV or HCV antigen, which, in some cases, can lead to a greater risk of developing liver cancer than HBV or HCV negative subjects. For example, in some embodiments, the heterologous antigen is an HBV antigen, such as a hepatitis B core antigen or a hepatitis B envelope antigen (US2012/0308580).

In some embodiments, the viral antigen is an EBV antigen, which, in some cases, can lead to a greater risk for developing Burkitt's lymphoma, nasopharyngeal carcinoma and Hodgkin's disease than EBV negative subjects. For example, EBV is a human herpes virus that, in some cases, is found associated with numerous human tumors of diverse tissue origin. While primarily found as an asymptomatic infection, EBV-positive tumors can be characterized by active expression of viral gene products, such as EBNA-1, LMP-1 and LMP-2A. In some embodiments, the heterologous antigen is an EBV antigen that can include Epstein-Barr nuclear antigen (EBNA)-1, EBNA-2, EBNA-3A, EBNA-3B, EBNA-3C, EBNA-leader protein (EBNA-LP), latent membrane proteins LMP-1, LMP-2A and LMP-2B, EBV-EA, EBV-MA or EBV-VCA.

In some embodiments, the viral antigen is an HTLV-1 or HTLV-2 antigen, which, in some cases, can lead to a greater risk for developing T-cell leukemia than HTLV-1 or HTLV-2 negative subjects. For example, in some embodiments, the heterologous antigen is an HTLV-antigen, such as TAX.

In some embodiments, the viral antigen is a HHV-8 antigen, which, in some cases, can lead to a greater risk for developing Kaposi's sarcoma than HHV-8 negative subjects. In some embodiments, the heterologous antigen is a CMV antigen, such as pp65 or pp64 (see U.S. Pat. No. 8,361,473).

In some embodiments, the antigen is an autoantigen, such as an antigen of a polypeptide associated with an autoimmune disease or disorder. In some embodiments, the autoimmune disease or disorder can be multiple sclerosis (MS), rheumatoid arthritis (RA), Sjogren syndrome, scleroderma, polymyositis, dermatomyositis, systemic lupus erythematosus, juvenile rheumatoid arthritis, ankylosing spondylitis, myasthenia gravis (MG), bullous pemphigoid (antibodies to basement membrane at dermal-epidermal junction), pemphigus (antibodies to mucopolysaccharide protein complex or intracellular cement substance), glomerulonephritis (antibodies to glomerular basement membrane), Goodpasture's syndrome, autoimmune hemolytic anemia (antibodies to erythrocytes), Hashimoto's disease (antibodies to thyroid), pernicious anemia (antibodies to intrinsic factor), idiopathic thrombocytopenic purpura (antibodies to platelets), Grave's disease, or Addison's disease (antibodies to thyroglobulin). In some embodiments, the autoantigen, such as an autoantigen associated with one of the foregoing autoimmune disease, can be collagen, such as type II collagen, mycobacterial heat shock protein, thyroglobulin, acetyl choline receptor (AcHR), myelin basic protein (MBP) or proteolipid protein (PLP). Specific autoimmune associated epitopes or antigens are known (see e.g., Bulek et al. (2012) Nat Immunol, 13:283-9; Harkiolaki et al. (2009) Immunity, 30:348-57; Skowera et al. (2008) J Clin Invest, 1(18): 3390-402).

In some embodiments, peptides of a target polypeptide for use in producing or generating a TCR of interest are known or can be readily identified. In some embodiments, peptides suitable for use in generating TCRs or antigen-binding portions can be determined based on the presence of an HLA-restricted motif in a target polypeptide of interest, such as a target polypeptide described below. In some embodiments, peptides are identified using available computer prediction models. In some examples, HLA-A0201-binding motifs and the cleavage sites for proteasomes and immune-proteasomes using computer prediction models are known. In some embodiments, for predicting MHC class I binding sites, such models include, but are not limited to, ProPred1 (Singh and Raghava (2001) Bioinformatics 17(12):1236-1237, and SYFPEITHI (see Schuler et al. (2007) Immunoinformatics Methods in Molecular Biology, 409(1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal A TCR may be cell-bound or in soluble form. In some embodiments, for purposes of the provided methods, the TCR is in cell-bound form expressed on the surface of a cell.

In some embodiments, the recombinant TCR is a full-length TCR. In some embodiments, the recombinant TCR is an antigen-binding portion. In some embodiments, the TCR is a dimeric TCR (dTCR). In some embodiments, the TCR is a single-chain TCR (scTCR). In some embodiments, a dTCR or scTCR have the structures as described in, e.g., International Pat. App. Pub. No. WO 03/020763, WO 04/033685 and WO 2011/044186.

In some embodiments, the recombinant TCR contains a sequence corresponding to the transmembrane sequence. In some embodiments, the TCR does contain a sequence corresponding to cytoplasmic sequences. In some embodiments, the TCR is capable of forming a TCR complex with CD3. In some embodiments, any of the recombinant TCRs, including a dTCR or scTCR, can be linked to signaling domains that yield an active TCR on the surface of a T cell. In some embodiments, the recombinant TCR is expressed on the surface of cells. In some embodiments of the dTCR or scTCR containing introduced or engineered inter-chain disulfide bonds, the native disulfide bonds are not present. In some embodiments, the one or more of the native cysteines forming a native inter-chain disulfide bonds are substituted to another residue, such as to a serine or alanine. In some embodiments, an introduced or engineered disulfide bond can be formed by mutating non-cysteine residues on the first and second segments to cysteine. Exemplary non-native disulfide bonds of a TCR are described in published International PCT No. WO2006/000830.

In certain embodiments, the TCR contains one or more modifications(s) to introduce one or more cysteine residues that are capable of forming one or more non-native disulfide bridges between the TCRα chain and TCRβ chain. In some embodiments, the TCR contains a TCRα chain or a portion thereof containing a TCRα constant domain containing one or more cysteine residues capable of forming a non-native disulfide bond with a TCRβ chain. In some embodiments, the transgene encodes a TCRβ chain or a portion thereof containing a TCRβ constant domain containing one or more cysteine residues capable of forming a non-native disulfide bond with a TCRα chain. In some embodiments, the TCR comprises a TCRα and/or TCRβ chain and/or a TCRα and/or TCRβ chain constant domains containing one or more modifications to introduce one or more disulfide bonds. In some embodiments, the transgene encodes a TCRα and/or TCRβ chain and/or a TCRα and/or TCRβ with one or more modifications to remove or prevent a native disulfide bond, e.g., between the TCRα by the transgene and the endogenous TCRβ chain, or between the TCRβ by the transgene and the endogenous TCR α chain. In some embodiments, one or more native cysteines that form and/or are capable of forming a native inter-chain disulfide bond are substituted to another residue, e.g., serine or alanine. In some embodiments, the cysteine is introduced at one or more of residue Thr48, Thr45, Tyr10, Thr45, and Ser15 with reference to numbering of a TCRα constant domain. In certain embodiments, cysteines can be introduced at residue Ser57, Ser77, Ser17, Asp59, of Glu15 of the TCRβ chain constant domain. Exemplary non-native disulfide bonds of a TCR are described in published International PCT No. WO2006/000830, WO 2006/037960 and Kuball et al. (2007) Blood, 109:2331-2338.

In some embodiments, the recombinant TCR is a dimeric TCR (dTCR). In some embodiments, the dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR chain variable region sequence is fused to the N terminus a sequence corresponding to a TCR chain constant region extracellular sequence, the first and second polypeptides being linked by a disulfide bond. In some embodiments, the bond can correspond to the native inter-chain disulfide bond present in native dimeric αβ TCRs. In some embodiments, the inter-chain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, the dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs interact to form a covalent bond between an amino acid in the first dimerization motif and an amino acid in the second dimerization motif linking the TCR α chain and TCR β chain together.

In some embodiments, the recombinant TCR is a single-chain TCR (scTCR or scTv). Typically, a scTCR can be generated using known methods, See e.g., Soo Hoo, W. F. et al. PNAS (USA) 89, 4759 (1992); Wülfing, C. and Plückthun, A., J. Mol. Biol. 242, 655 (1994); Kurucz, I. et al. PNAS (USA) 90 3830 (1993); International Pat. App. Pub. Nos. WO 96/13593, WO 96/18105, WO 99/60120, WO 99/18129, WO 03/020763, WO 2011/044186; and Schlueter, C. J. et al. J. Mol. Biol. 256, 859 (1996). In some embodiments, the scTCR contains an introduced non-native disulfide inter-chain bond to facilitate the association of the TCR chains (see e.g. International Pat. App. Pub. No. WO 03/020763). In some embodiments, the scTCR is a non-disulfide linked truncated TCR in which heterologous leucine zippers fused to the C-termini thereof facilitate chain association (see e.g. International Pat. App. Pub. No. WO 99/60120). In some embodiments, the scTCR contains a TCRα variable domain covalently linked to a TCRβ variable domain via a peptide linker (see e.g., International Pat. App. Pub. No. WO 99/18129).

In some embodiments, the scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment. In some embodiments, the scTCR contains a first segment constituted by an α chain variable region sequence fused to the N terminus of an α chain extracellular constant domain sequence, and a second segment constituted by α chain variable region sequence fused to the N terminus of a sequence chain extracellular constant and transmembrane sequence, and, optionally, a linker sequence linking the C terminus of the first segment to the N terminus of the second segment. In some embodiments, the scTCR contains a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and, optionally, a linker sequence linking the C terminus of the first segment to the N terminus of the second segment.

In some embodiments, the linker of the scTCRs that links the first and second TCR segments can be any linker capable of forming a single polypeptide strand, while retaining TCR binding specificity. In some embodiments, the linker sequence may, for example, have the formula -P-AA-P- wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, the linker has the formula -PGGG-(SGGGG)$_5$-P- wherein P is proline, G is glycine and S is serine (SEQ ID NO:22). In some embodiments, the linker has the sequence GSADDAKKDAAKKDGKS (SEQ ID NO:23)

In some embodiments, the scTCR contains a covalent disulfide bond linking a residue of the immunoglobulin region of the constant domain of the α chain to a residue of the immunoglobulin region of the constant domain of the β chain. In some embodiments, the interchain disulfide bond in a native TCR is not present. For example, in some embodiments, one or more cysteines can be incorporated into the constant region extracellular sequences of the first and second segments of the scTCR polypeptide. In some cases, both a native and a non-native disulfide bond may be desirable.

In some embodiments, the TCR or antigen-binding fragment thereof exhibits an affinity with an equilibrium dissociation constant ($K_D$) for a target antigen of between or between about $10^{-5}$ and $10^{-12}$ M and all individual values and ranges therein. In some embodiments, the target antigen is an MHC-peptide complex or ligand.

III. Methods for Producing Engineered Cells

In some aspects, provided herein are methods for stimulating, activating, engineering, cultivating, and/or expanding one or more populations of cell, e.g., enriched T cells. In some embodiments, the one or more populations of cells are stimulated or activated, such as by incubating the cells under stimulating conditions and/or in the presence of a stimulatory reagent. In certain embodiments, the one or more populations of enriched T cells are genetically engineered, such as by introducing a heterologous polynucleotide to the cells of the one or more populations. In certain embodiments, the one or more populations of enriched T cells are cultivated, e.g., cultivated under conditions that promote or allow for T cell division, growth, or expansion, such as for a fixed amount of time or until a threshold limit for expansion is achieved. In some embodiments, the engineering process includes the steps of stimulating and then transducing the cells. In particular embodiments, the engineering process includes the steps of stimulating, transducing, and then expanding the cells. In certain embodiments, the cells are not expanded.

In particular embodiments, provided herein are methods for generating genetically engineered T cell composition from one or more initial, e.g., source, populations of T cells. In some embodiments, a population of enriched T cells is incubated under stimulating conditions, thereby generating a stimulated population. In certain embodiments, a heterologous polynucleotide is introduced to cells of the stimulated population, thereby generating a transformed population. In certain embodiments, the transformed population is then expanded, such as for a set amount of time or until a threshold expansion is achieved, thereby resulting in an expanded population. In particular embodiments, the transformed population or the expanded population is harvested or collected, and optionally formulated, such as for administration to a subject or for cryopreservation. In some embodiments, the population is or contains CD4+ T cells and CD8+ T cells.

In certain embodiments, provided herein are methods for generating genetically engineered T cell composition from two initial, e.g., source populations of T cells. In some embodiments, the two populations of enriched T cells are separately incubated under stimulating conditions, thereby generating two separate stimulated populations. In certain embodiments, a heterologous polynucleotide is introduced to cells of the two separate stimulated populations, thereby generating two separate transformed populations. In certain embodiments, the two separate transformed populations are then expanded, such as for a set amount of time or until a threshold expansion is achieved, thereby resulting in two separate expanded populations. In particular embodiments, the two separate transformed populations or the two separate expanded populations are harvested or collected, and optionally formulated, such as for administration to a subject or for cryopreservation. In particular embodiments, the two separate populations originate or are derived from the same biological sample or different biological samples from the same individual subject. In some embodiments, the two separate populations are or contain a population of enriched CD4+ T cells and a separate population of CD8+ T cells.

In some embodiments, the provided methods herein can be used to determine, measure, or assess the presence, level, amount, or expression of proteins, e.g., surface proteins, of cells prior to, during, or after the completion of a process for generating engineered cells. In some embodiments, the mass spectrometry profile is obtained by any of the provided methods described herein, e.g., in Section I. In some embodiments, the provided methods can be used to measure, monitor, or assess the effects of an engineering process on the presence, absence, amount, level and/or relative abundance of one more proteins, e.g., surface proteins.

In certain embodiments, a mass spectrometry profile is obtained from cells of an engineered cell composition. In particular embodiments, a mass spectrometry profile is obtained from cells that will undergo or that are undergoing the process for engineering cells, e.g., such as any engineering process described herein such as in Section-III. In certain embodiments, the cells have undergone any one of the processes for genetic engineering described herein, e.g., in Section-III. In some embodiments, the process for engineering cells is or includes steps for generating cells expressing a recombinant receptor. In particular embodiments, the recombinant receptor is a CAR. In certain embodiments, the recombinant receptor is any CAR that is described herein, e.g., in Section II-C-1-a or II-C-1-b. In particular embodiments, the recombinant receptor is a recombinant TCR, e.g., a recombinant TCR described herein such as in Section II-C-1-c. In some embodiments, the recombinant receptor is an anti-CD19 CAR. In certain embodiments, the recombinant receptor is an anti-BCMA CAR. In certain embodiments, the mass spectrometry profile is obtained from a cell composition to measure or identify a CAR expressed by the engineered cells. In particular embodiments, the mass spectrometry profile is obtained from a cell composition during a process for engineering CAR expressing cells.

In particular embodiments, mass spectrometry profiles are obtained from two or more cell compositions containing cells collected at different stages or time points of an engineering process. In some embodiments, the two or more cell compositions are generated from the same subject or subjects. In certain embodiments, the mass spectrometry profiles may be analyzed or compared to each other to identify effects of the engineering process on the cells, e.g., expression of surface proteins, or in some aspects, changes in characteristics, properties, or attributes such as but not limited to viability, differentiation, or proliferative potential.

In particular embodiments, mass spectrometry profiles are obtained from two or more cell compositions containing cells collected at the same stages or time points of different engineering processes, e.g., different engineering processes for generating cells expressing the same recombinant receptor. In particular embodiments, the two or more cell compositions are generated from the same subject or subjects. In certain embodiments, the mass spectrometry profiles may be analyzed or compared to each other to identify effects of the different engineering process on the cells.

In some embodiments, mass spectrometry profiles expressing the same recombinant receptor, e.g., CAR, generated from different engineering processes are generated, such as to compare or determine the effects of the engineering processes on the resulting engineered cells. In certain embodiments, the manufacturing processes are different with respect to one or more steps, or reagents of the process. In some embodiments, the processes differs in by the use of at least one reagent. In some embodiments, the reagent is a stimulatory reagent, such as any stimulatory reagent described herein, e.g., in Section III-B. In some embodiments, the reagent may include the antibodies, e.g., anti-CD3 antibodies, cytokines, e.g., IL-2, soluble anti-CD3 and/or anti-CD28 antibodies, bead or oligomeric particle based stimulatory reagents, or irradiated antigen expressing cells. In some embodiments, the reagent is a vector for gene delivery, e.g., a viral vector.

Particular embodiments contemplate that the provided methods may also be employed to analyze or characterize reagents that are used in association with the production or maintenance of engineered T cell compositions. In certain embodiments, the reagents, such as any of the reagents described herein, e.g., in Section-III, may contain proteins and may thus be investigated by mass spectrometry according to the methods described herein.

In some aspects, variability among unit doses of a cell composition can be due to one or more aspects of manufacturing processes employed in the generation or manufacture of an engineered cell therapy. In some cases, changes to raw materials or handling or storage thereof may impact variables observed herein to impact risk of toxicity and/or outcomes. In some aspects, lot-to-lot variability or storage/handling of raw materials and/or the use of different raw materials among processes carried out across a number of subjects, may impact, such as by increasing the variability of or increasing or decreasing, certain aspects of the generated cell compositions, such as aspects that, if varied, may result in variability in toxicity risk or clinical outcomes among subjects administered cell therapies, particularly among such subjects differing in certain patient-specific attributes.

In some embodiments, provided are approaches involving the assessment, testing for, and/or controlling for potential impact on or variability in one or more such product attributes or risks or likelihoods, as a result of a (such as any or all) raw material(s), lot(s), reagent(s) or storage or handling thereof, or change thereto by any of the provided methods. In some embodiments, such approaches include assays such as those carried out prior to the use of such raw material, lot, storage or handling, in production of a cell composition to be administered to a subject or before such administration. In some aspects, the assays assess the impact of the raw material, lot, change, or handling or storage method, on one or more attributes in a cell composition such as those observed herein to impact risk of toxicity or outcome or to exacerbate the impact of patient-to-patient variability in such outcomes. In some aspects, the assays assess whether an acceptably low degree of variability or variance in, compared to another material, lot, or storage or handling method, or an acceptably low impact, on such one or more attributes. In certain embodiments, the assays are or include the use of mass spectrometry, such as any of the methods provided herein, e.g., in Section-I. In certain embodiments, the assays are or include the generation of mass spectrometry profiles.

In some aspects, the raw material, lot, or method for storage or handling, is released for use in manufacturing of the cell therapy to be administered to the patient—or such cell therapy is administered to the patient—if, such as only if or only after, the assay, e.g., those involving mass spectrometry such as by the methods described herein, confirms that such variability or variance or impact is within the acceptable range or value or limit. In some embodiments, determining that variability in one or more such attribute is below a certain level with a new raw material or lot or storage or handling method, can mitigate risk of toxicity or reduction in response following implementation of such new raw material or lot or storage or handling method. In some embodiments, among such provided methods are methods that assay a composition prior to release of product and/or adjust the dosing strategy based on such parameters.

The observations were consistent with the interpretation that it can be advantageous—e.g., in identifying a safe and effective cell composition dose—to consider (e.g., assay for prior to release of product and/or factor into the dosing strategy) the degree of variability in factors that may contribute to certain cell/antigen-specific activities in a composition, from the perspective of compositions produced from cells derived from different subjects, and/or in the presence of one or more different storage or handling conditions of raw material or reagents, e.g. using different lots of reagents or other raw materials. In some aspects, it is advantageous to reduce the variability in such parameters and/or confirm acceptable range of variability among such different conditions/lots such as when introducing a new lot or reagent stored or handled under different conditions, such as using a mass spectrometry assay as described herein, e.g., in Section I.

In some embodiments, the provided methods, articles of manufacture, compositions, doses and dosing strategies are advantageous in that they take into account and, where relevant, adjust or correct for, potential sources of variability, including those deriving from change in reagents and/or patient-to-patient variability. For example, in some embodiments, it can be advantageous to produce engineered T cells by a process that involves the use of a T cell stimulation/expansion reagent (or lot thereof) that has been verified by a release assay to be below or within an acceptable range of variability or variance as compared to a threshold level of a parameter, e.g., a mass spectrometry profile or a level, amount, concentration, or modification of one or more proteins of the reagent, In some embodiments, the reagent is a reagent that is or contains proteins. In particular embodiments, the reagent is used during the engineering process to stimulate, activate, transduce, transfect, transform, cultivate, or expand the cells. In some embodiments, the protein profile is or is A. Isolation or Selection of Cells from Samples In some embodiments, the processing steps include isolation of cells or compositions thereof from biological samples, such as those obtained from or derived from a subject, such as one having a particular disease or condition or in need of a cell therapy or to which cell therapy will be administered. In some aspects, the subject is a human, such as a subject who is a patient in need of a particular therapeutic intervention, such as the adoptive cell therapy for which cells are being isolated, processed, and/or engineered. Accordingly, the cells in some embodiments are primary cells, e.g., primary human cells. In some embodiments, the cells comprise CD4+ and CD8+ T cells. In some embodiments, the cells comprise CD4+ or CD8+ T cells. The samples include tissue, fluid, and other samples taken directly from the subject. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In some embodiments, the cell is a regulatory T cell (Treg). In some embodiments, the cell further comprises a recombinant FOXP3 or variant thereof.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, preparation of the engineered cells includes one or more culture and/or preparation steps. The cells for engineering may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, or pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contain cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished in a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the preparation methods include steps for freezing, e.g., cryopreserving, the cells, either before or after isolation, selection and/or enrichment and/or incubation for transduction and engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

In some embodiments, isolation of the cells or populations includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components. In some embodiments, the methods include density-based cell separation methods, such as the preparation of white blood cells from peripheral blood by lysing the red blood cells and centrifugation through a Percoll or Ficoll gradient.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with a selection regent, such as an antibody or binding partner that specifically binds to such markers, followed generally by washing steps and separation of cells having bound the antibody or binding partner, from those cells having not bound to the antibody or binding partner.

In some embodiments, at least a portion of the selection step includes incubation of cells with a selection reagent. The incubation with a selection reagent or reagents, e.g., as part of selection methods which may be performed using one or more selection reagents for selection of one or more different cell types based on the expression or presence in or on the cell of one or more specific molecules, such as surface markers, e.g., surface proteins, intracellular markers, or nucleic acid. In some embodiments, any known method using a selection reagent or reagents for separation based on such markers may be used. In some embodiments, the selection reagent or reagents result in a separation that is affinity- or immunoaffinity-based separation. For example, the selection in some aspects includes incubation with a reagent or reagents for separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner. In some embodiments, the selection and/or other aspects of the process is as described in International Patent Application Publication Number WO/2015/164675.

In some aspects of such processes, a volume of cells is mixed with an amount of a desired affinity-based selection reagent. The immunoaffinity-based selection can be carried out using any system or method that results in a favorable energetic interaction between the cells being separated and the molecule specifically binding to the marker on the cell, e.g., the antibody or other binding partner on the solid surface, e.g., particle. In some embodiments, methods are carried out using particles such as beads, e.g. magnetic beads, that are coated with a selection agent (e.g. antibody) specific to the marker of the cells. The particles (e.g. beads) can be incubated or mixed with cells in a container, such as a tube or bag, while shaking or mixing, with a constant cell density-to-particle (e.g., bead) ratio to aid in promoting energetically favored interactions. In other cases, the methods include selection of cells in which all or a portion of the selection is carried out in the internal cavity of a centrifugal chamber, for example, under centrifugal rotation. In some embodiments, incubation of cells with selection reagents, such as immunoaffinity-based selection reagents, is performed in a centrifugal chamber. In certain embodiments, the isolation or separation is carried out using a system, device, or apparatus described in International Patent Application, Publication Number WO2009/072003, or US 20110003380 A1. In one example, the system is a system as described in International Publication Number WO2016/073602.

In some embodiments, by conducting such selection steps or portions thereof (e.g., incubation with antibody-coated particles, e.g., magnetic beads) in the cavity of a centrifugal chamber, the user is able to control certain parameters, such as volume of various solutions, addition of solution during processing and timing thereof, which can provide advantages compared to other available methods. For example, the ability to decrease the liquid volume in the cavity during the incubation can increase the concentration of the particles (e.g. bead reagent) used in the selection, and thus the chemical potential of the solution, without affecting the total number of cells in the cavity. This in turn can enhance the pairwise interactions between the cells being processed and the particles used for selection. In some embodiments, carrying out the incubation step in the chamber, e.g., when associated with the systems, circuitry, and control as described herein, permits the user to effect agitation of the solution at desired time(s) during the incubation, which also can improve the interaction.

In some embodiments, at least a portion of the selection step is performed in a centrifugal chamber, which includes incubation of cells with a selection reagent. In some aspects of such processes, a volume of cells is mixed with an amount of a desired affinity-based selection reagent that is far less than is normally employed when performing similar selections in a tube or container for selection of the same number of cells and/or volume of cells according to manufacturer's instructions. In some embodiments, an amount of selection reagent or reagents that is/are no more than 5%, no more than 10%, no more than 15%, no more than 20%, no more than 25%, no more than 50%, no more than 60%, no more than 70% or no more than 80% of the amount of the same selection reagent(s) employed for selection of cells in a tube or container-based incubation for the same number of cells and/or the same volume of cells according to manufacturer's instructions is employed.

In some embodiments, for selection, e.g., immunoaffinity-based selection of the cells, the cells are incubated in the cavity of the chamber in a composition that also contains the selection buffer with a selection reagent, such as a molecule that specifically binds to a surface marker on a cell that it desired to enrich and/or deplete, but not on other cells in the composition, such as an antibody, which optionally is coupled to a scaffold such as a polymer or surface, e.g., bead, e.g., magnetic bead, such as magnetic beads coupled to monoclonal antibodies specific for CD4 and CD8. In some embodiments, as described, the selection reagent is added to cells in the cavity of the chamber in an amount that is substantially less than (e.g. is no more than 5%, 10%, 20%, 30%, 40%, 50%, 60%, 70% or 80% of the amount) as compared to the amount of the selection reagent that is typically used or would be necessary to achieve about the same or similar efficiency of selection of the same number of cells or the same volume of cells when selection is performed in a tube with shaking or rotation. In some embodiments, the incubation is performed with the addition of a selection buffer to the cells and selection reagent to achieve a target volume with incubation of the reagent of, for example, 10 mL to 200 mL, such as at least or about at least or about or 10 mL, 20 mL, 30 mL, 40 mL, 50 mL, 60 mL, 70 mL, 80 mL, 90 mL, 100 mL, 150 mL or 200 mL. In some embodiments, the selection buffer and selection reagent are pre-mixed before addition to the cells. In some embodiments, the selection buffer and selection reagent are separately added to the cells. In some embodiments, the selection incubation is carried out with periodic gentle mixing condition, which can aid in promoting energetically favored interactions and thereby permit the use of less overall selection reagent while achieving a high selection efficiency.

In some embodiments, the total duration of the incubation with the selection reagent is from or from about 5 minutes to 6 hours, such as 30 minutes to 3 hours, for example, at least or about at least 30 minutes, 60 minutes, 120 minutes or 180 minutes.

In some embodiments, the incubation generally is carried out under mixing conditions, such as in the presence of spinning, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm), such as at an RCF at the sample or wall of the chamber or other container of from or from about 80 g to 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, such process is carried out within the entirely closed system to which the chamber is integral. In some embodiments, this process (and in some aspects also one or more additional step, such as a previous wash step washing a sample containing the cells, such as an apheresis sample) is carried out in an automated fashion, such that the cells, reagent, and other components are drawn into and pushed out of the chamber at appropriate times and centrifugation effected, so as to complete the wash and binding step in a single closed system using an automated program.

In some embodiments, after the incubation and/or mixing of the cells and selection reagent and/or reagents, the incubated cells are subjected to a separation to select for cells based on the presence or absence of the particular reagent or reagents. In some embodiments, the separation is performed in the same closed system in which the incubation of cells with the selection reagent was performed. In some embodiments, after incubation with the selection reagents, incubated cells, including cells in which the selection reagent has bound are transferred into a system for immunoaffinity-based separation of the cells. In some embodiments, the system for immunoaffinity-based separation is or contains a magnetic separation column.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

In some embodiments, the process steps further include negative and/or positive selection of the incubated and cells, such as using a system or apparatus that can perform an affinity-based selection. In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker+) at a relatively higher level (marker$_{high}$) on the positively or negatively selected cells, respectively.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., CD28$^+$ CD62L$^-$ CCR7$^-$ CD27$^-$ CD127$^-$ CD4$^-$ CD8$^-$ CD45RA$^-$ and/or CD45RO$^+$ T cells, are isolated by positive or negative selection techniques. In some embodiments, such cells are selected by incubation with one or more antibody or binding partner that specifically binds to such markers. In some embodiments, the antibody or binding partner can be conjugated, such as directly or indirectly, to a solid support or matrix to effect selection, such as a magnetic bead or paramagnetic bead.

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker$^+$) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a CD4$^+$ or CD8$^+$ selection step is used to separate CD4$^+$ helper and CD8$^+$ cytotoxic T cells. Such CD4$^+$ and CD8$^+$ populations can be further sorted into sub-populations by positive or negative selection for markers expressed or expressed to a relatively higher degree on one or more naive, memory, and/or effector T cell subpopulations.

In some embodiments, CD8$^+$ cells are further enriched for or depleted of naive, central memory, effector memory, and/or central memory stem cells, such as by positive or negative selection based on surface antigens associated with the respective subpopulation. In some embodiments, enrichment for central memory T (T$_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) *J Immunother.* 35(9):689-701. In some embodiments, combining T$_{CM}$-enriched CD8$^+$ T cells and CD4$^+$ T cells further enhances efficacy.

In embodiments, memory T cells are present in both CD62L$^+$ and CD62L$^-$ subsets of CD8$^+$ peripheral blood lymphocytes. PBMC can be enriched for or depleted of CD62L$^-$CD8$^+$ and/or CD62L$^+$CD8$^+$ fractions, such as using anti-CD8 and anti-CD62L antibodies.

In some embodiments, the enrichment for central memory T (T$_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8$^+$ population enriched for T$_{CM}$ cells is carried out by depletion of cells expressing CD4, CD14, CD45RA, and positive selection or enrichment for cells expressing CD62L. In one aspect, enrichment for central memory T (T$_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8$^+$ cell population or subpopulation, also is used to generate the CD4$^+$ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4+ cells, where both the negative and positive fractions are retained. The negative fraction then is subjected to negative selection based on expression of CD14 and CD45RA or ROR1, and positive selection based on a marker characteristic of central memory T cells, such as CD62L or CCR7, where the positive and negative selections are carried out in either order.

CD4+ T helper cells are sorted into naïve, central memory, and effector cells by identifying cell populations that have cell surface antigens. CD4+ lymphocytes can be obtained by standard methods. In some embodiments, naive CD4+ T lymphocytes are CD45RO−, CD45RA− CD62L− CD4+ T cells. In some embodiments, central memory CD4+ cells are CD62L+ and CD45RO+. In some embodiments, effector CD4+ cells are CD62L− and CD45RO−.

In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In vitro and In vivo, p 17-25 Edited by: S. A. Brooks and U. Schumacher © Humana Press Inc., Totowa, N.J.).

In some aspects, the sample or composition of cells to be separated is incubated with a selection reagent, such as containing small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some aspects, separation is achieved in a procedure in which the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In some embodiments, the affinity-based selection is via magnetic-activated cell sorting (MACS) (Miltenyi Biotec, Auburn, Calif.). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain aspects, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International PCT Publication No. WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood may be automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood. 1:72-82, and Wang et al. (2012) *J Immunother.* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10:1567-1573; and Godin et al. (2008) J Biophoton. 1(5):355-376). In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° per minute and stored in the vapor phase of a liquid nitrogen storage tank.

In some embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

B. Activation and Stimulation of T Cells

In some embodiments, the one or more processing steps include a step of stimulating the isolated cells, such as selected cell populations. The incubation may be prior to or in connection with genetic engineering, such as prior to or in connection of transducing cells with a nucleic acid or vector encoding the recombinant receptor (e.g. CAR). In some embodiments, the stimulation results in activation and/or proliferation of the cells, for example, prior to transduction. In some embodiments, the cells are incubated under stimulating conditions.

In some embodiments, the provided methods for producing engineered cell include one or more of a cultivation, incubation, culture, and/or genetic engineering steps. For example, in some embodiments, provided are methods for incubating and/or engineering the depleted cell populations and culture-initiating compositions. In some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant receptor, e.g., CAR.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling region of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2, IL-15 and/or IL-7. In some aspects, the IL-2 concentration is at least about 10 units/mL. In some aspects, the IL-2 concentration is at least about 50 units/mL, at least about 100 units/mL or at least about 200 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood.1:72-82, and/or Wang et al. (2012) J Immunother. 35(9):689-701.

In some embodiments, the T cells are stimulated by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the cells are stimulated in the presence of antigen-expressing cells, such as non-dividing antigen expressing cells. In some cases, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In some embodiments, at least a portion of the incubation in the presence of one or more stimulating conditions or stimulatory agents is carried out in the internal cavity of a centrifugal chamber, for example, under centrifugal rotation, such as described in International Publication Number WO2016/073602. In some embodiments, at least a portion of the incubation performed in a centrifugal chamber includes mixing with a reagent or reagents to induce stimulation and/or activation. In some embodiments, cells, such as selected cells, are mixed with a stimulating condition or stimulatory agent in the centrifugal chamber. In some aspects of such processes, a volume of cells is mixed with an amount of one or more stimulating conditions or agents that is far less than is normally employed when performing similar stimulations in a cell culture plate or other system.

In some embodiments, the stimulating agent is added to cells in the cavity of the chamber in an amount that is substantially less than (e.g. is no more than 5%, 10%, 20%, 30%, 40%, 50%, 60%, 70% or 80% of the amount) as compared to the amount of the stimulating agent that is typically used or would be necessary to achieve about the same or similar efficiency of selection of the same number of cells or the same volume of cells when selection is performed without mixing in a centrifugal chamber, e.g. in a tube or bag with periodic shaking or rotation. In some embodiments, the incubation is performed with the addition of an incubation buffer to the cells and stimulating agent to achieve a target volume with incubation of the reagent of, for example, 10 mL to 200 mL, such as at least or about at least or about or 10 mL, 20 mL, 30 mL, 40 mL, 50 mL, 60 mL, 70 mL, 80 mL, 90 mL, 100 mL, 150 mL, or 200 mL. In some embodiments, the incubation buffer and stimulating agent are pre-mixed before addition to the cells. In some embodiments, the incubation buffer and stimulating agent are separately added to the cells. In some embodiments, the stimulating incubation is carried out with periodic gentle mixing condition, which can aid in promoting energetically favored interactions and thereby permit the use of less overall stimulating agent while achieving stimulating and activation of cells.

In some embodiments, the incubation generally is carried out under mixing conditions, such as in the presence of spinning, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm), such as at an RCF at the sample or wall of the chamber or other container of from or from about 80 g to 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, the total duration of the incubation, e.g. with the stimulating agent, is between or between about 1 hour and 96 hours, 1 hour and 72 hours, 1 hour and 48 hours, 4 hours and 36 hours, 8 hours and 30 hours or 12 hours and 24 hours, such as at least or about at least 6 hours, 12 hours, 18 hours, 24 hours, 36 hours or 72 hours. In some embodiments, the further incubation is for a time between or about between 1 hour and 48 hours, 4 hours and 36 hours, 8 hours and 30 hours or 12 hours and 24 hours, inclusive.

In particular embodiments, the stimulating conditions include incubating, culturing, and/or cultivating the cells with a stimulatory reagent. In certain embodiments, the stimulatory reagent contains or includes a bead. In certain embodiments, the initiation of the stimulation occurs when the cells are incubated or contacted with the stimulatory reagent. In particular embodiments, the stimulatory reagent contains or includes an oligomeric reagent, e.g., a streptavidin mutein oligomer. In particular embodiments, the stimulatory reagent activates and/or is capable of activating one or more intracellular signaling domains of one or more components of a TCR complex and/or one or more intracellular signaling domains of one or more costimulatory molecules.

In some embodiments, the stimulating conditions or stimulatory reagents include one or more agent, e.g., ligand, which is capable of activating an intracellular signaling domain of a TCR complex. In some embodiments, an agent as contemplated herein can include, but is not limited to, RNA, DNA, proteins (e.g., enzymes), antigens, polyclonal antibodies, monoclonal antibodies, antibody fragments, carbohydrates, lipids lectins, or any other biomolecule with an affinity for a desired target. In some embodiments, the desired target is a T cell receptor and/or a component of a T cell receptor. In certain embodiments, the desired target is CD3. In certain embodiment, the desired target is a T cell costimulatory molecule, e.g., CD28, CD137 (4-1-BB), OX40, or ICOS. The one or more agents may be attached directly or indirectly to the bead by a variety of methods known and available in the art. The attachment may be covalent, noncovalent, electrostatic, or hydrophobic and may be accomplished by a variety of attachment means, including for example, a chemical means, a mechanical means, or an enzymatic means. In some embodiments, the agent is an antibody or antigen binding fragment thereof, such as a Fab. In some embodiments, a biomolecule (e.g., a biotinylated anti-CD3 antibody) may be attached indirectly to the bead via another biomolecule (e.g., anti-biotin antibody) that is directly attached to the bead.

In some embodiments, the stimulatory reagent contains one or more agents (e.g. antibody) that is attached to a bead (e.g., a paramagnetic bead) and specifically binds to one or more of the following macromolecules on a cell (e.g., a T cell): CD2, CD3, CD4, CD5, CD8, CD25, CD27, CD28, CD29, CD31, CD44, CD45RA, CD45RO, CD54 (ICAM-1), CD127, MHCI, MHCII, CTLA-4, ICOS, PD-1, OX40, CD27L (CD70), 4-1BB (CD137), 4-1BBL, CD30L, LIGHT, IL-2R, IL-12R, IL-1R, IL-15R; IFN-gammaR, TNF-alphaR, IL-4R, IL-10R, CD18/CD11a (LFA-1), CD62L (L-selectin), CD29/CD49d (VLA-4), Notch ligand (e.g. Delta-like 1/4, Jagged 1/2, etc.), CCR1, CCR2, CCR3, CCR4, CCR5, CCR7, and CXCR3 or fragment thereof including the corresponding ligands to these macromolecules or fragments thereof. In some embodiments, an agent (e.g. antibody) attached to the bead specifically binds to one or more of the following macromolecules on a cell (e.g. a T cell): CD28, CD62L, CCR7, CD27, CD127, CD3, CD4, CD8, CD45RA, and/or CD45RO.

In some embodiments, one or more of the agents attached to the bead is an antibody. The antibody can include a polyclonal antibody, monoclonal antibody (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')2, and Fv). In some embodiments, the stimulatory reagent is an antibody fragment (including antigen-binding fragment), e.g., a Fab, Fab'-SH, Fv, scFv, or (Fab')2 fragment. It will be appreciated that constant regions of any isotype can be used for the antibodies contemplated herein, including IgG, IgM, IgA, IgD, and IgE constant regions, and that such constant regions can be obtained from any human or animal species (e.g., murine species). In some embodiments, the agent is an antibody that binds to and/or recognizes one or more components of a T cell receptor. In particular embodiments, the agent is an anti-CD3 antibody. In certain embodiments, the agent is an antibody that binds to and/or recognizes a co-receptor. In some embodiments, the stimulatory reagent comprises an anti-CD28 antibody.

In certain embodiments, the stimulatory reagent contains a particle, e.g., a bead, that is conjugated or linked to one or more agents, e.g., biomolecules, that are capable of activating and/or expanding cells, e.g., T cells. In some embodiments, the one or more agents are bound to a bead. In some embodiments, the bead is biocompatible, i.e., composed of a material that is suitable for biological use. In some embodiments, the beads are non-toxic to cultured cells, e.g., cultured T cells. In some embodiments, the beads may be any particles which are capable of attaching agents in a manner that permits an interaction between the agent and a cell.

In some embodiments, the stimulatory reagent contains a bead and one or more agents that directly interact with a macromolecule on the surface of a cell. In certain embodiments, the bead (e.g., a paramagnetic bead) interacts with a cell via one or more agents (e.g., an antibody) specific for one or more macromolecules on the cell (e.g., one or more cell surface proteins). In certain embodiments, the bead (e.g., a paramagnetic bead) is labeled with a first agent described herein, such as a primary antibody (e.g., an anti-biotin antibody) or other biomolecule, and then a second agent, such as a secondary antibody (e.g., a biotinylated anti-CD3 antibody) or other second biomolecule (e.g., streptavidin), is added, whereby the secondary antibody or other second biomolecule specifically binds to such primary antibodies or other biomolecule on the particle.

In some embodiments, the stimulatory reagent comprises one or more agents that are attached to a bead comprising a metal oxide core (e.g., an iron oxide inner core) and a coat (e.g., a protective coat), wherein the coat comprises polystyrene. In certain embodiments, the beads are monodisperse, paramagnetic (e.g., superparamagnetic) beads comprising a paramagnetic (e.g., superparamagnetic) iron core, e.g., a core comprising magnetite (Fe3O4) and/or maghemite (γFe2O3) c and a polystyrene coat or coating. In some embodiments, the bead is non-porous. In some embodiments, the beads contain a functionalized surface to which the one or more agents are attached. In certain embodiments, the one or more agents are covalently bound to the beads at the surface. In some embodiments, the one or more agents include an antibody or antigen-binding fragment thereof. In some embodiments, the one or more agents include an anti-CD3 antibody and an anti-CD28 antibody. In some embodiments, the one or more agents include an anti-CD3 antibody and/or an anti-CD28 antibody, and an antibody or antigen fragment thereof capable of binding to a labeled antibody (e.g., biotinylated antibody), such as a labeled anti-CD3 or anti-CD28 antibody. In certain embodiments, the beads have a density of about 1.5 g/cm3 and a surface area of about 1 m2/g to about 4 m2/g. In particular embodiments; the beads are monodisperse superparamagnetic beads that have a diameter of about 4.5 μm and a density of about 1.5 g/cm3. In some embodiments, the beads the beads are monodisperse superparamagnetic beads that have a mean diameter of about 2.8 μm and a density of about 1.3 g/cm3.

In particular embodiments, the stimulatory reagent contains an oligomeric reagent, e.g., a streptavidin mutein reagent, that is conjugated, linked, or attached to one or more agent, e.g., ligand, which is capable of activating an intracellular signaling domain of a TCR complex. In some embodiments, the one or more agents have an attached binding domain or binding partner (e.g., a binding partner C) that is capable of binding to oligomeric reagent at a particular binding sites (e.g., binding site Z). In some embodiments, a plurality of the agent is reversibly bound to the oligomeric reagent. In various embodiments, the oligomeric reagent has a plurality of the particular binding sites which, in certain embodiments, are reversibly bound to a plurality of agents at the binding domain (e.g., binding partner C). In some embodiments, the amount of bound agents are reduced or decreased in the presence of a competition reagent, e.g., a reagent that is also capable of binding to the particular binding sites (e.g., binding site Z).

In some embodiments, the stimulatory reagent is or includes a reversible systems in which at least one agent (e.g., an agent that is capable of producing a signal in a cell such as a T cell) is associated, e.g., reversibly associated, with the oligomeric reagent. In some embodiments, the reagent contains a plurality of binding sites capable of binding, e.g., reversibly binding, to the agent. In some cases, the reagent is a oligomeric particle reagent having at least one attached agent capable of producing a signal in a cell such as a T cell. In some embodiments, the agent contains at least one binding site, e.g., a binding site B, that can specifically bind an epitope or region of the molecule and also contains a binding partner, also referred to herein as a binding partner C, that specifically binds to at least one binding site of the reagent, e.g., binding site Z of the reagent. In some embodiments, the binding interaction between the binding partner C and the at least one binding site Z is a non-covalent interaction. In some cases, the binding interaction between the binding partner C and the at least one binding site Z is a covalent interaction. In some embodiments, the binding interaction, such as non-covalent interaction, between the binding partner C and the at least one binding site Z is reversible.

Substances that may be used as oligomeric reagents in such reversible systems are known, see e.g., U.S. Pat. Nos. 5,168,049; 5,506,121; 6,103,493; 7,776,562; 7,981,632; 8,298,782; 8,735,540; 9,023,604; and International published PCT Appl. Nos. WO2013/124474 and WO2014/076277. Non-limiting examples of reagents and binding partners capable of forming a reversible interaction, as well as substances (e.g. competition reagents) capable of reversing such binding, are described.

In some embodiments, the stimulatory reagent is an oligomeric particle reagent that is composed of and/or contains a plurality of streptavidin or streptavidin mutein tetramers. In certain embodiments, the oligomeric particle reagent provided herein contains a plurality of binding sites that reversibly bind or are capable of reversibly binding to one or more agents, e.g., a stimulatory agent and/or a selection agent. In some embodiments, the oligomeric particle has a radius, e.g., an average radius, of between 80 nm and 120 nm, inclusive; a molecular weight, e.g., an average molecular weight of between $7.5 \times 10^6$ g/mol and $2 \times 10^8$ g/mol, inclusive; and/or an amount, e.g., an average amount, of between 500 and 10,000 streptavidin or streptavidin mutein tetramers, inclusive. In some embodiments, the oligomeric particle reagent is bound, e.g., reversibly bound, to one or more agents, such as an agent that binds to a molecule, e.g. receptor, on the surface of a cell. In certain embodiments, the one or more agents are agents described herein, e.g., in Section II-C-3. In some embodiments, the agent is an anti-CD3 and/or an anti-CD28 Fab, such as a Fab that contains a binding partner, e.g., a streptavidin binding peptide, e.g. Strep-Tag® II. In particular embodiments, the one or more agents is an anti-CD3 and/or an anti CD28 Fab containing a binding partner, e.g., a streptavidin binding peptide, e.g. Strep-Tag® II.

C. Methods for Introducing a Heterologous Polynucleotide

In some embodiments, the processing steps include introduction of a nucleic acid molecule encoding a recombinant protein. Various methods for the introduction of genetically engineered components, e.g., recombinant receptors, e.g., CARs or TCRs, are well known and may be used with the provided methods and compositions. Exemplary methods include those for transfer of nucleic acids encoding the polypeptides or receptors, including via viral vectors, e.g., retroviral or lentiviral, non-viral vectors or transposons, e.g. Sleeping Beauty transposon system. Methods of gene transfer can include transduction, electroporation or other method that results into gene transfer into the cell.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, it may be desired to safeguard against the potential that overexpression of a stimulatory factor (for example, a lymphokine or a cytokine) could potentially result in an unwanted outcome or lower efficacy in a subject, such as a factor associated with toxicity in a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell 2:223, 1977) which confers ganciclovir sensitivity; the cellular hypoxanthine phosphribosyltransferase (HPRT) gene, the cellular adenine phosphoribosyltransferase (APRT) gene, bacterial cytosine deaminase (Mullen et al., Proc. Natl. Acad. Sci. USA. 89:33 (1992)).

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109).

Methods of lentiviral transduction are known. Exemplary methods are described in, e.g., Wang et al. (2012) *J. Immunother.* 35(9): 689-701; Cooper et al. (2003) *Blood.* 101: 1637-1644; Verhoeyen et al. (2009) *Methods Mol Biol.* 506: 97-114; and Cavalieri et al. (2003) Blood. 102(2): 497-505.

In some embodiments, recombinant nucleic acids are transferred into T cells via electroporation (see, e.g., Chicaybam et al, (2013) *PLoS ONE* 8(3): e60298 and Van Tedeloo et al. (2000) *Gene Therapy* 7(16): 1431-1437). In some embodiments, recombinant nucleic acids are transferred into T cells via transposition (see, e.g., Manuri et al. (2010) Hum Gene Ther 21(4): 427-437; Sharma et al. (2013) *Molec Ther Nucl Acids* 2, e74; and Huang et al. (2009) *Methods Mol Biol* 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion, e.g. with nucleic acids encoding a recombinant receptor, e.g., a T cell receptor (TCR) or a chimeric antigen receptor (CAR). This transfection for the introduction of the gene of the desired polypeptide or receptor can be carried out with any suitable retroviral vector, for example. The genetically modified cell population can then be liberated from the initial stimulus (the CD3/CD28 stimulus, for example) and subsequently be stimulated with a second type of stimulus (e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

In some cases, a vector may be used that does not require that the cells, e.g., T cells, are activated. In some such instances, the cells may be selected and/or transduced prior to activation. Thus, the cells may be engineered prior to, or subsequent to culturing of the cells, and in some cases at the same time as or during at least a portion of the culturing.

In some aspects, the cells further are engineered to promote expression of cytokines or other factors. Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

As described above, in some embodiments, the cells are incubated and/or cultured prior to or in connection with genetic engineering. The incubation steps can include culture, cultivation, stimulation, activation, propagation and/or freezing for preservation, e.g. cryopreservation.

In some embodiments, the introducing is carried out by contacting one or more cells of a composition with a nucleic acid molecule encoding the recombinant protein, e.g. recombinant receptor. In some embodiments, the contacting can be effected with centrifugation, such as spinoculation (e.g. centrifugal inoculation). Such methods include any of those as described in International Publication Number WO2016/073602. Exemplary centrifugal chambers include those produced and sold by Biosafe SA, including those for use with the Sepax® and Sepax® 2 system, including an A-200/F and A-200 centrifugal chambers and various kits for use with such systems. Exemplary chambers, systems, and processing instrumentation and cabinets are described, for example, in U.S. Pat. Nos. 6,123,655, 6,733,433 and Published U.S. Patent Application, Publication No.: US 2008/0171951, and published international patent application, publication no. WO 00/38762, the contents of each of which are incorporated herein by reference in their entirety. Exemplary kits for use with such systems include, but are not limited to, single-use kits sold by BioSafe SA under product names CS-430.1, CS-490.1, CS-600.1 or CS-900.2.

In some embodiments, the system is included with and/or placed into association with other instrumentation, including instrumentation to operate, automate, control and/or monitor aspects of the transduction step and one or more various other processing steps performed in the system, e.g. one or more processing steps that can be carried out with or in connection with the centrifugal chamber system as described herein or in International Publication Number WO2016/073602. This instrumentation in some embodiments is contained within a cabinet. In some embodiments, the instrumentation includes a cabinet, which includes a housing containing control circuitry, a centrifuge, a cover, motors, pumps, sensors, displays, and a user interface. An exemplary device is described in U.S. Pat. Nos. 6,123,655, 6,733,433 and US 2008/0171951.

In some embodiments, the system comprises a series of containers, e.g., bags, tubing, stopcocks, clamps, connectors, and a centrifuge chamber. In some embodiments, the containers, such as bags, include one or more containers, such as bags, containing the cells to be transduced and the viral vector particles, in the same container or separate containers, such as the same bag or separate bags. In some embodiments, the system further includes one or more containers, such as bags, containing medium, such as diluent and/or wash solution, which is pulled into the chamber and/or other components to dilute, resuspend, and/or wash components and/or compositions during the methods. The containers can be connected at one or more positions in the system, such as at a position corresponding to an input line, diluent line, wash line, waste line and/or output line.

In some embodiments, the chamber is associated with a centrifuge, which is capable of effecting rotation of the chamber, such as around its axis of rotation. Rotation may occur before, during, and/or after the incubation in connection with transduction of the cells and/or in one or more of the other processing steps. Thus, in some embodiments, one or more of the various processing steps is carried out under rotation, e.g., at a particular force. The chamber is typically capable of vertical or generally vertical rotation, such that the chamber sits vertically during centrifugation and the side wall and axis are vertical or generally vertical, with the end wall(s) horizontal or generally horizontal.

In some embodiments, the composition containing cells, viral particles and reagent can be rotated, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm). In some embodiments, the rotation is carried at a force, e.g., a relative centrifugal force, of from or from about 100 g to 3200 g (e.g. at or about or at least at or about 100 g, 200 g, 300 g, 400 g, 500 g, 1000 g, 1500 g, 2000 g, 2500 g, 3000 g or 3200 g), as measured for example at an internal or external wall of the chamber or cavity. The term "relative centrifugal force" or RCF is generally understood to be the effective force imparted on an object or substance (such as a cell, sample, or pellet and/or a point in the chamber or other container being rotated), relative to the earth's gravitational force, at a particular point in space as compared to the axis of rotation. The value may be determined using well-known formulas, taking into account the gravitational force, rotation speed and the radius of rotation (distance from the axis of rotation and the object, substance, or particle at which RCF is being measured).

In some embodiments, during at least a part of the genetic engineering, e.g. transduction, and/or subsequent to the genetic engineering the cells are transferred to a container such as a bag for culture of the genetically engineered cells, such as for cultivation or expansion of the cells, as described above. In some embodiments, the container for cultivation or expansion of the cells is a bioreactor bag, such as a perfusion bag.

1. Nucleic Acids and Vectors

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, the recombinant receptors are encoded by one or more polynucleotides (e.g., nucleic acid molecules). In some embodiments, the cells that are used in adoptive cell therapy are engineered using, vectors for genetic engineering.

In some aspects, the polynucleotide contains a single coding sequence. In other instances, the polynucleotide contains at least two different coding sequences. In some aspects, the recombinant receptor is or contains a chimeric antigen receptor (CAR). In some aspects, the recombinant receptor is or contains a T cell receptor (TCR), e.g., a transgenic TCR. In some embodiments, the polynucleotides and vectors are used for expression in cells the recombinant receptor.

In some cases, the nucleic acid sequence encoding the recombinant receptor contains a signal sequence that encodes a signal peptide. In other aspects, the signal sequence may encode a heterologous or non-native signal peptide, such as the exemplary signal peptide of the GMCSFR alpha chain set forth in SEQ ID NO: 25 and encoded by the nucleotide sequence set forth in SEQ ID NO:24. In some cases, the nucleic acid sequence encoding the recombinant receptor, e.g., chimeric antigen receptor (CAR) contains a signal sequence that encodes a signal peptide. Non-limiting exemplary examples of signal peptides include, for example, the GMCSFR alpha chain signal peptide set forth in SEQ ID NO: 25 and encoded by the nucleotide sequence set forth in SEQ ID NO:24, or the CD8 alpha signal peptide set forth in SEQ ID NO:26.

In some embodiments, the polynucleotide encoding the recombinant receptor contains at least one promoter that is operatively linked to control expression of the recombinant receptor. In some examples, the polynucleotide contains two, three, or more promoters operatively linked to control expression of the recombinant receptor.

In certain cases where nucleic acid molecules encode two or more different polypeptide chains, each of the polypeptide chains can be encoded by a separate nucleic acid molecule. For example, two separate nucleic acids are provided, and each can be individually transferred or introduced into the cell for expression in the cell.

In some embodiments, such as those where the polynucleotide contains a first and second nucleic acid sequence, the coding sequences encoding each of the different polypeptide chains can be operatively linked to a promoter, which can be the same or different. In some embodiments, the nucleic acid molecule can contain a promoter that drives the expression of two or more different polypeptide chains. In some embodiments, such nucleic acid molecules can be multicistronic (bicistronic or tricistronic, see e.g., U.S. Pat. No. 6,060,273). In some embodiments, transcription units can be engineered as a bicistronic unit containing an IRES (internal ribosome entry site), which allows coexpression of gene products ((e.g. encoding a cell surface marker or modified form thereof and encoding the recombinant receptor) by a message from a single promoter. Alternatively, in some cases, a single promoter may direct expression of an RNA that contains, in a single open reading frame (ORF), two or three genes (e.g. encoding a cell surface marker and encoding the recombinant receptor) separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as a T2A, can cause the ribosome to skip (ribosome skipping) synthesis of a peptide bond at the C-terminus of a 2A element, leading to separation between the end of the 2A sequence and the next peptide downstream (see, for example, de Felipe, *Genetic Vaccines and Ther.* 2:13 (2004) and de Felipe et al. *Traffic* 5:616-626 (2004)). Various 2A elements are known. Examples of 2A sequences that can be used in the methods and system disclosed herein, without limitation, 2A sequences from the foot-and-mouth disease virus (F2A, e.g., SEQ ID NO: 21), equine rhinitis A virus (E2A, e.g., SEQ ID NO: 20), Thosea assign virus (T2A, e.g., SEQ ID NO: 6 or 17), and porcine teschovirus-1 (P2A, e.g., SEQ ID NO: 18 or 19) as described in U.S. Patent Publication No. 20070116690.

In some embodiments, the nucleic acid encoding a cell surface marker and the nucleic acid encoding the recombinant receptor are operably linked to the same promoter and are optionally separated by an internal ribosome entry site (IRES), or a nucleic acid encoding a self-cleaving peptide or a peptide that causes ribosome skipping, which optionally is a T2A, a P2A, a E2A or a F2A. In some embodiments, the nucleic acid encoding a cell surface marker and the nucleic acid encoding the recombinant receptor are operably linked to two different promoters. In some embodiments, the nucleic acid encoding a cell surface marker and the nucleic acid encoding the recombinant receptor are present or inserted at different locations within the genome of the cell.

In some embodiments, the vector contains a nucleic acid sequence encoding one or more marker(s). In some embodiments, the one or more marker(s) is a transduction marker, surrogate marker and/or a selection marker.

In some embodiments, the marker is a transduction marker or a surrogate marker. A transduction marker or a surrogate marker can be used to detect cells that have been introduced with the polynucleotide, e.g., a polynucleotide encoding a recombinant receptor. In some embodiments, the transduction marker can indicate or confirm modification of a cell. In some embodiments, the surrogate marker is a protein that is made to be co-expressed on the cell surface with the recombinant receptor, e.g. CAR. In particular embodiments, such a surrogate marker is a surface protein that has been modified to have little or no activity. In certain embodiments, the surrogate marker is encoded on the same polynucleotide that encodes the recombinant receptor. In some embodiments, the nucleic acid sequence encoding the recombinant receptor is operably linked to a nucleic acid sequence encoding a marker, optionally separated by an internal ribosome entry site (IRES), or a nucleic acid encoding a self-cleaving peptide or a peptide that causes ribosome skipping, such as a 2A sequence, such as a T2A, a P2A, an E2A or an F2A. Extrinsic marker genes may in some cases be utilized in connection with engineered cell to permit detection or selection of cells and, in some cases, also to promote cell suicide.

Exemplary surrogate markers can include truncated forms of cell surface polypeptides, such as truncated forms that are non-functional and to not transduce or are not capable of transducing a signal or a signal ordinarily transduced by the full-length form of the cell surface polypeptide, and/or do not or are not capable of internalizing Exemplary truncated cell surface polypeptides including truncated forms of growth factors or other receptors such as a truncated human epidermal growth factor receptor 2 (tHER2), a truncated epidermal growth factor receptor (tEGFR, exemplary tEGFR sequence set forth in SEQ ID NO: 7 or 16) or a prostate-specific membrane antigen (PSMA) or modified form thereof. tEGFR may contain an epitope recognized by the antibody cetuximab (Erbitux®) or other therapeutic anti-EGFR antibody or binding molecule, which can be used to identify or select cells that have been engineered with the tEGFR construct and an encoded exogenous protein, and/or to eliminate or separate cells expressing the encoded exogenous protein. See U.S. Pat. No. 8,802,374 and Liu et al., Nature Biotech. 2016 April; 34(4): 430-434). In some aspects, the marker, e.g. surrogate marker, includes all or part (e.g., truncated form) of CD34, a NGFR, a CD19 or a truncated CD19, e.g., a truncated non-human CD19, or epidermal growth factor receptor (e.g., tEGFR). In some embodiments, the marker is or comprises a fluorescent protein, such as green fluorescent protein (GFP), enhanced green fluorescent protein (EGFP), such as super-fold GFP (sfGFP), red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. In some embodiments, the marker is or comprises an enzyme, such as a luciferase, the lacZ gene from E. coli, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a modified form thereof.

In some embodiments, the nucleic acid encoding the marker is operably linked to a polynucleotide encoding for a linker sequence, such as a cleavable linker sequence, e.g., a T2A. For example, a marker, and optionally a linker sequence, can be any as disclosed in PCT Pub. No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 7 or 16 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 16.

Any of the recombinant receptors described herein can be encoded by polynucleotides containing one or more nucleic acid sequences encoding a cell surface marker and/or recombinant receptors, in any combinations or arrangements. For example, one, two, three or more polynucleotides can encode one, two, three or more different polypeptides, e.g., a cell surface marker and/or recombinant receptors. In some embodiments, one vector or construct contains a nucleic acid sequence encoding a cell surface marker, and a separate vector or construct contains a nucleic acid sequence encoding a recombinant receptor, e.g., CAR. In some embodiments, the nucleic acid encoding the a cell surface marker and the nucleic acid encoding the recombinant receptor are operably linked to two different promoters. In some embodiments, the nucleic acid encoding the recombinant receptor is present downstream of the nucleic acid encoding the a cell surface marker.

2. Viral Vectors and Preparation of Viral Vectors

In some embodiments, the polynucleotide encoding the recombinant receptor is introduced into a composition containing cultured cells, such as by retroviral transduction, transfection, or transformation.

Also provided are vectors or constructs containing such nucleic acids and/or polynucleotides. In some embodiments, the vectors or constructs contain one or more promoters operatively linked to the nucleic acid encoding the recombinant receptor to drive expression thereof. In some embodiments, the promoter is operatively linked to one or more than one nucleic acid molecules or polynucleotides. Thus, also provided are vectors, such as those that contain any of the polynucleotides provided herein. In some embodiments, the vector includes a first polynucleotide encoding a cell surface marker and a second polynucleotide encoding a recombinant receptor, e.g., CAR.

In some cases, the vector is a viral vector, such as a retroviral vector, e.g., a lentiviral vector or a gammaretroviral vector. Also provided a set or combination of vectors. In some embodiments, the set or combination of vectors comprises a first vector and a second vector, wherein the first vector comprises the first polynucleotide, e.g., a first polynucleotide encoding a cell surface marker, and the second vector comprises the second polynucleotide encoding a recombinant receptor, e.g., CAR. Also provided are compositions containing such set or combination of vectors. In some embodiments, the set or combination of vectors, are used together for engineering of cells. In some embodiments, the first and the second vectors in the set are introduced simultaneously or sequentially, in any order into a cell for engineering.

In some embodiments, the vectors include viral vectors, e.g., retroviral or lentiviral, non-viral vectors or transposons, e.g. Sleeping Beauty transposon system, vectors derived from simian virus 40 (SV40), adenoviruses, adeno-associated virus (AAV), lentiviral vectors or retroviral vectors, such as gamma-retroviral vectors, retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV) or adeno-associated virus (AAV).

The viral vector genome is typically constructed in a plasmid form that can be transfected into a packaging or producer cell line. In any of such examples, the nucleic acid encoding a recombinant protein, such as a recombinant receptor, is inserted or located in a region of the viral vector, such as generally in a non-essential region of the viral genome. In some embodiments, the nucleic acid is inserted into the viral genome in the place of certain viral sequences to produce a virus that is replication defective.

Any of a variety of known methods can be used to produce retroviral particles whose genome contains an RNA copy of the viral vector genome. In some embodiments, at least two components are involved in making a virus-based gene delivery system: first, packaging plasmids, encompassing the structural proteins as well as the enzymes necessary to generate a viral vector particle, and second, the viral vector itself, i.e., the genetic material to be transferred. Biosafety safeguards can be introduced in the design of one or both of these components.

In some embodiments, the packaging plasmid can contain all retroviral, such as HIV-1, proteins other than envelope proteins (Naldini et al., 1998). In other embodiments, viral vectors can lack additional viral genes, such as those that are associated with virulence, e.g. vpr, vif, vpu and nef, and/or Tat, a primary transactivator of HIV. In some embodiments, lentiviral vectors, such as HIV-based lentiviral vectors, comprise only three genes of the parental virus: gag, pol and rev, which reduces or eliminates the possibility of reconstitution of a wild-type virus through recombination.

In some embodiments, the viral vector genome is introduced into a packaging cell line that contains all the components necessary to package viral genomic RNA, transcribed from the viral vector genome, into viral particles. Alternatively, the viral vector genome may comprise one or more genes encoding viral components in addition to the one or more sequences, e.g., recombinant nucleic acids, of interest. In some aspects, in order to prevent replication of the genome in the target cell, however, endogenous viral genes required for replication are removed and provided separately in the packaging cell line.

In some embodiments, a packaging cell line is transfected with one or more plasmid vectors containing the components necessary to generate the particles. In some embodiments, a packaging cell line is transfected with a plasmid containing the viral vector genome, including the LTRs, the cis-acting packaging sequence and the sequence of interest, i.e. a nucleic acid encoding an antigen receptor, such as a CAR; and one or more helper plasmids encoding the virus enzymatic and/or structural components, such as Gag, pol and/or rev. In some embodiments, multiple vectors are utilized to separate the various genetic components that generate the retroviral vector particles. In some such embodiments, providing separate vectors to the packaging cell reduces the chance of recombination events that might otherwise generate replication competent viruses. In some embodiments, a single plasmid vector having all of the retroviral components can be used.

In some embodiments, the retroviral vector particle, such as lentiviral vector particle, is pseudotyped to increase the transduction efficiency of host cells. For example, a retroviral vector particle, such as a lentiviral vector particle, in some embodiments is pseudotyped with a VSV-G glycoprotein, which provides a broad cell host range extending the cell types that can be transduced. In some embodiments, a packaging cell line is transfected with a plasmid or polynucleotide encoding a non-native envelope glycoprotein, such as to include xenotropic, polytropic or amphotropic envelopes, such as Sindbis virus envelope, GALV or VSV-G.

In some embodiments, the packaging cell line provides the components, including viral regulatory and structural proteins, that are required in trans for the packaging of the viral genomic RNA into lentiviral vector particles. In some embodiments, the packaging cell line may be any cell line that is capable of expressing lentiviral proteins and producing functional lentiviral vector particles. In some aspects, suitable packaging cell lines include 293 (ATCC CCL X), 293T, HeLA (ATCC CCL 2), D17 (ATCC CCL 183), MDCK (ATCC CCL 34), BHK (ATCC CCL-10) and Cf2Th (ATCC CRL 1430) cells.

In some embodiments, the packaging cell line stably expresses the viral protein(s). For example, in some aspects, a packaging cell line containing the gag, pol, rev and/or other structural genes but without the LTR and packaging components can be constructed. In some embodiments, a packaging cell line can be transiently transfected with nucleic acid molecules encoding one or more viral proteins along with the viral vector genome containing a nucleic acid molecule encoding a heterologous protein, and/or a nucleic acid encoding an envelope glycoprotein.

In some embodiments, the viral vectors and the packaging and/or helper plasmids are introduced via transfection or infection into the packaging cell line. The packaging cell line produces viral vector particles that contain the viral vector genome. Methods for transfection or infection are well known. Non-limiting examples include calcium phosphate, DEAE-dextran and lipofection methods, electroporation and microinjection.

When a recombinant plasmid and the retroviral LTR and packaging sequences are introduced into a special cell line (e.g., by calcium phosphate precipitation for example), the packaging sequences may permit the RNA transcript of the recombinant plasmid to be packaged into viral particles, which then may be secreted into the culture media. The media containing the recombinant retroviruses in some embodiments is then collected, optionally concentrated, and used for gene transfer. For example, in some aspects, after cotransfection of the packaging plasmids and the transfer vector to the packaging cell line, the viral vector particles are recovered from the culture media and titered by standard methods used by those of skill in the art.

In some embodiments, a retroviral vector, such as a lentiviral vector, can be produced in a packaging cell line, such as an exemplary HEK 293T cell line, by introduction of plasmids to allow generation of lentiviral particles. In some embodiments, a packaging cell is transfected and/or contains a polynucleotide encoding gag and pol, and a polynucleotide encoding a recombinant receptor, such as an antigen receptor, for example, a CAR. In some embodiments, the packaging cell line is optionally and/or additionally transfected with and/or contains a polynucleotide encoding a rev protein. In some embodiments, the packaging cell line is optionally and/or additionally transfected with and/or contains a polynucleotide encoding a non-native envelope glycoprotein, such as VSV-G. In some such embodiments, approximately two days after transfection of cells, e.g. HEK 293T cells, the cell supernatant contains recombinant lentiviral vectors, which can be recovered and titered.

Recovered and/or produced retroviral vector particles can be used to transduce target cells using the methods as described. Once in the target cells, the viral RNA is reverse-transcribed, imported into the nucleus and stably integrated into the host genome. One or two days after the integration of the viral RNA, the expression of the recombinant protein, e.g. antigen receptor, such as CAR, can be detected.

D. Cultivating and/or Expansion

In some embodiments, the provided methods include one or more steps for cultivating engineered cells, e.g., cultivating cells under conditions that promote proliferation and/or expansion. In certain embodiments, the provided methods do not include steps for cultivating engineered cells. In certain embodiments, there is a greater number of engineered cells following the completion of the process as compared to the initial source cells from which the cells were generated. In various embodiments, there is a smaller number of engineered cells following the completion of the process as compared to the initial source cells from which the cells were generated. In some embodiments, engineered cells are cultivated under conditions that promote proliferation and/or expansion subsequent to a step of genetically engineering, e.g., introducing a recombinant polypeptide to the cells by transduction or transfection. In particular embodiments, the cells are cultivated after the cells have been incubated under stimulating conditions and transduced or transfected with a recombinant polynucleotide, e.g., a polynucleotide encoding a recombinant receptor. In some embodiments, the cultivation produces an output composition containing a composition of enriched T cells that express the recombinant receptor (e.g. CAR).

In some embodiments, the engineered cells are cultured in a container that can be filled, e.g. via the feed port, with cell media and/or cells for culturing of the added cells. The cells can be from any cell source for which culture of the cells is desired, for example, for expansion and/or proliferation of the cells.

In some aspects, the culture media is an adapted culture medium that supports that growth, cultivation, expansion or proliferation of the cells, such as T cells. In some aspects, the medium can be a liquid containing a mixture of salts, amino acids, vitamins, sugars or any combination thereof. In some embodiments, the culture media further contains one or more stimulating conditions or agents, such as to stimulate the cultivation, expansion or proliferation of cells during the incubation. In some embodiments, the stimulating condition is or includes one or more cytokine selected from IL-2, IL-7 or IL-15. In some embodiments, the cytokine is a recombinant cytokine. In some embodiments, the concentration of the one or more cytokine in the culture media during the culturing or incubation, independently, is from or from about 1 IU/mL to 1500 IU/mL, such as from or from about 1 IU/mL to 100 IU/mL, 2 IU/mL to 50 IU/mL, 5 IU/mL to 10 IU/mL, 10 IU/mL to 500 IU/mL, 50 IU/mL to 250 IU/mL or 100 IU/mL to 200 IU/mL, 50 IU/mL to 1500 IU/mL, 100 IU/mL to 1000 IU/mL or 200 IU/mL to 600 IU/mL. In some embodiments, the concentration of the one or more cytokine, independently, is at least or at least about 1 IU/mL, 5 IU/mL, 10 IU/mL, 50 IU/mL, 100 IU/mL, 200 IU/mL, 500 IU/mL, 1000 IU/mL or 1500 IU/mL.

In some aspects, the cells are incubated for at least a portion of time after transfer of the engineered cells and culture media. In some embodiments, the stimulating conditions generally include a temperature suitable for the growth of primary immune cells, such as human T lymphocytes, for example, at least about 25 degrees Celsius, generally at least about 30 degrees, and generally at or about 37 degrees Celsius. In some embodiments, the cells are incubated at a temperature of 25 to 38 degrees Celsius, such as 30 to 37 degrees Celsius, for example at or about 37 degrees Celsius ±2 degrees Celsius. In some embodiments, the incubation is carried out for a time period until the culture, e.g. cultivation or expansion, results in a desired or threshold density, number or dose of cells. In some embodiments, the incubation is greater than or greater than about or is for about or 24 hours, 48 hours, 72 hours, 96 hours, 5 days, 6 days, 7 days, 8 days, 9 days or more.

In some embodiments, the cells are incubated under conditions to maintain a target amount of carbon dioxide in the cell culture. In some aspects, this ensures optimal cultivation, expansion and proliferation of the cells during the growth. In some aspects, the amount of carbon dioxide ($CO_2$) is between 10% and 0% (v/v) of said gas, such as between 8% and 2% (v/v) of said gas, for example an amount of or about 5% (v/v) $CO_2$.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In some embodiments, cells are incubated using containers, e.g., bags, which are used in connection with a bioreactor. In some cases, the bioreactor can be subject to motioning or rocking, which, in some aspects, can increase oxygen transfer. Motioning the bioreactor may include, but is not limited to rotating along a horizontal axis, rotating along a vertical axis, a rocking motion along a tilted or inclined horizontal axis of the bioreactor or any combination thereof. In some embodiments, at least a portion of the incubation is carried out with rocking. The rocking speed and rocking angle may be adjusted to achieve a desired agitation. In some embodiments the rock angle is or is about 20°, 19°, 18°, 17°, 16°, 15°, 14°, 13°, 12°, 11°, 10°, 9°, 8°, 7°, 6°, 5°, 4°, 3°, 2° or 1°. In certain embodiments, the rock angle is between 6-16°. In other embodiments, the rock angle is between 7-16°. In other embodiments, the rock angle is between 8-12°. In some embodiments, the rock rate is 1, 2, 3, 4, 5, 6, 7, 8, 9, 10, 11, 1 12, 13, 14 15, 16, 17, 18, 19, 20, 21, 22, 23, 24, 25, 26, 27, 28, 29, 30, 31, 32, 33, 34, 35, 36, 37, 38, 39, 40 rpm. In some embodiments, the rock rate is between 4 and 12 rpm, such as between 4 and 6 rpm, inclusive. At least a portion of the cell culture expansion is performed with a rocking motion, such as at an angle of between 5° and 10°, such as 6°, at a constant rocking speed, such as a speed of between 5 and 15 RPM, such as 6 RMP or 10 RPM. The CD4+ and CD8+ cells are each separately expanded until they each reach a threshold amount or cell density.

In some embodiments, at least a portion of the incubation is carried out under static conditions. In some embodiments, at least a portion of the incubation is carried out with perfusion, such as to perfuse out spent media and perfuse in fresh media during the culture. In some embodiments, the method includes a step of perfusing fresh culture medium into the cell culture, such as through a feed port. In some embodiments, the culture media added during perfusion contains the one or more stimulating agents, e.g. one or more recombinant cytokine, such as IL-2, IL-7 and/or IL-15. In some embodiments, the culture media added during perfusion is the same culture media used during a static incubation.

In some embodiments, the cells are expanding or cultivated in the presence of one or more anti-idiotype antibodies, such as an anti-idiotypic antibody that binds to or recognizes the recombinant receptor that is expressed by the engineered cells.

In some embodiments, subsequent to the incubation, the container, e.g., bag, is re-connected to a system for carrying out the one or more other processing steps of for manufacturing, generating or producing the cell therapy, such as is re-connected to the system containing the centrifugal chamber. In some aspects, cultured cells are transferred from the bag to the internal cavity of the chamber for formulation of the cultured cells.

E. Compositions and Formulations

In particular embodiments, the mass spectrometry profile is obtained from an engineered cell composition such as a formulated cell composition, e.g., a cell therapy. In certain embodiments, the mass spectrometry profile is obtained from the cell composition to verify that at least a portion of the mass spectrometry profile falls within a tolerable range, e.g., does not fall outside a threshold variability or variance. In particular embodiments, the mass spectrometry profile is obtained from the cell composition to identify or verify the presence of a recombinant receptor expressed by cells of the cell composition, e.g., a formulated cell composition or cell therapy.

In some embodiments, the dose of cells comprising cells engineered with a recombinant antigen receptor, e.g. CAR or TCR, is provided as a composition or formulation, such as a pharmaceutical composition or formulation. Such compositions can be used in accord with the provided methods, and/or with the provided articles of manufacture or compositions, such as in the prevention or treatment of diseases, conditions, and disorders, or in detection, diagnostic, and prognostic methods.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell or agent and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulation or composition may also contain more than one active ingredient useful for the particular indication, disease, or condition being prevented or treated with the cells or agents, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the agents or cells are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The pharmaceutical composition in some embodiments contains agents or cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The agents or cells can be administered by any suitable means, for example, by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells or agent. In some embodiments, it is administered by multiple bolus administrations of the cells or agent, for example, over a period of no more than 3 days, or by continuous infusion administration of the cells or agent.

For the prevention or treatment of disease, the appropriate dosage may depend on the type of disease to be treated, the type of agent or agents, the type of cells or recombinant receptors, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

The cells or agents may be administered using standard administration techniques, formulations, and/or devices. Provided are formulations and devices, such as syringes and vials, for storage and administration of the compositions. With respect to cells, administration can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell or an agent that treats or ameliorates symptoms of neurotoxicity), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the agent or cell populations are administered parenterally. The term "parenteral," as used herein, includes intravenous, intramuscular, subcutaneous, rectal, vaginal, and intraperitoneal administration. In some embodiments, the agent or cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the agent or cells in a solvent, such as in admixture with a suitable carrier, diluent, or excipient such as sterile water, physiological saline, glucose, dextrose, or the like.

The formulations to be used for in vivo administration are generally sterile. Sterility may be readily accomplished, e.g., by filtration through sterile filtration membranes.

IV. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known. Reference to "about" a value or parameter herein includes (and describes) embodiments that are directed to that value or parameter per se. For example, description referring to "about X" includes description of "X".

As used herein, recitation that nucleotides or amino acid positions "correspond to" nucleotides or amino acid positions in a disclosed sequence, such as set forth in the Sequence listing, refers to nucleotides or amino acid positions identified upon alignment with the disclosed sequence to maximize identity using a standard alignment algorithm, such as the GAP algorithm. By aligning the sequences, corresponding residues can be identified, for example, using conserved and identical amino acid residues as guides. In general, to identify corresponding positions, the sequences of amino acids are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New.Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carrillo et al. (1988) SIAM J Applied Math 48: 1073).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Among the vectors are viral vectors, such as retroviral, e.g., gammaretroviral and lentiviral vectors.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

As used herein, "percent (%) amino acid sequence identity" and "percent identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various known ways, for instance, using publicly available computer software such as BLAST, BLAST-2, ALIGN or Megalign (DNASTAR) software. Appropriate parameters for aligning sequences can be determined, including any algorithms needed to achieve maximal alignment over the full length of the sequences being compared.

An amino acid substitution may include replacement of one amino acid in a polypeptide with another amino acid. The substitution may be a conservative amino acid substitution or a non-conservative amino acid substitution. Amino acid substitutions may be introduced into a binding molecule, e.g., antibody, of interest and the products screened for a desired activity, e.g., retained/improved antigen binding, decreased immunogenicity, or improved ADCC or CDC.

Amino acids generally can be grouped according to the following common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

In some embodiments, conservative substitutions can involve the exchange of a member of one of these classes for another member of the same class. In some embodiments, non-conservative amino acid substitutions can involve exchanging a member of one of these classes for another class.

As used herein, a composition refers to any mixture of two or more products, substances, or compounds, including cells. It may be a solution, a suspension, liquid, powder, a paste, aqueous, non-aqueous or any combination thereof.

As used herein, a "subject" is a mammal, such as a human or other animal, and typically is human.

V. Exemplary Embodiments

Among the provided embodiments are:
1. A method for identifying a mass spectrometry (MS) profile of a genetically engineered cell composition, the method comprising:
(a) determining a test mass spectrometry profile of a sample from a test engineered cell composition or a subset thereof using a mass spectrometry technique, said test engineered cell composition comprising immune cells comprising a recombinant receptor;
(b) comparing the test mass spectrometry profile to a reference mass spectrometry profile; and
(c) identifying one or more differences in the presence, absence or level of at least one data component in the test mass spectrometry profile compared to the reference mass spectrometry profile, thereby identifying a mass spectrometry profile of the cell composition comprising the recombinant receptor.
2. The method of embodiment 1, wherein the reference mass spectrometry profile is of a sample from a reference composition or is an average mass spectra profile of a number of samples from a plurality of reference compositions.
3. The method of embodiment 1 or claim 2, wherein the test engineered cell composition is for use in an autologous cell therapy.
4. The method of any of embodiments 1-3, wherein the test engineered cell composition is produced by a process comprising:
(i) selecting or isolating immune cells from a sample from a subject, thereby generating a source composition, optionally wherein the biological sample is a leukapheresis sample, apheresis sample or a whole blood sample;
(ii) incubating the cells of the source composition with a stimulatory reagent, thereby generating a stimulated composition, wherein the incubating is optionally carried out in the presence of one or more cytokines;
(iii) introducing a nucleic acid encoding the recombinant receptor into immune cells of the stimulated composition, thereby generating a transformed composition; and
(iv) culturing the stimulated composition at 37° C. for at least 24 hours, thereby generating the test engineered cell composition, wherein the culturing is optionally carried out in the presence of one or more cytokines.
5. The method of any of embodiments 2-4, wherein the reference composition or each of the plurality of reference cell compositions has not been introduced with a nucleic acid molecule encoding the recombinant receptor.
6. The method of any of embodiments 1-5, wherein the reference mass spectrometry profile is of a sample from a reference composition and the reference cell composition is a source cell composition comprising the immune cells from which the test cell composition has been derived or obtained.
7. The method of any of embodiments 1-6, wherein the reference mass spectrometry profile is of a sample from a reference composition, wherein:
the test engineered cell composition comprises immune cells obtained from a subject, said immune cells comprising a nucleic acid molecule encoding the recombinant receptor; and
the reference cell composition is an input composition comprising the immune cells obtained from the subject that do not comprise the nucleic acid encoding the recombinant receptor.
8. The method of any of embodiments 1-7, wherein the reference mass spectrometry profile is of a sample from a reference composition and the reference cell composition is a composition obtained after, prior to or during a stage of the manufacturing process for producing the test engineered cell composition.
9. The method of any of embodiments 1-8, wherein the test engineered cell composition is a sample obtained from a subject previously administered the engineered cell composition.
10. The method of embodiment 9, wherein the sample obtained from the subject comprises immune cells engineered with the recombinant receptor, optionally as detected by flow cytometry or polymerase chain reaction (PCR).
11. The method of embodiment 9 or embodiment 10, wherein the sample obtained from the subject is a blood sample or a tumor sample.
12. The method of any of embodiments 9-11, wherein the sample obtained from the subject is obtained between or between about 6 and 30 days, between or between about 14 and 29 days, or between or between about 17 and 22 days after administration of the engineered cells to the subject.
13. The method of any of embodiments 9-12, wherein the sample is obtained from the subject at a time at or about or immediately after peak cells expressing the recombinant receptor are detectable in the blood of the subject.
14. The method of any of embodiments 1-8, wherein the test engineered cell composition comprises cells that have been contacted by an agent to produce a recombinant receptor-dependent activity, optionally wherein the agent is a target antigen that is capable of being bound by the recombinant receptor or is an anti-idiotypic antibody specific to the antibody.

15. The method of any of embodiments 2-14, wherein the reference mass spectrometry profile is an average mass spectra profile of a number of samples from a plurality of reference compositions.

16. The method of embodiment 15, wherein each of the plurality of reference compositions comprise cells comprising the recombinant receptor.

17. The method of embodiment 15 or embodiment 16, wherein each of the plurality of reference compositions was produced by the same process or substantially the same process as the engineered cell composition.

18. A method for assessing a process for producing a genetically engineered cell composition, the method comprising:
(a) obtaining an average mass spectrometry profile of a sample of a plurality of reference engineered cell compositions or a subset thereof, wherein each of the plurality of the reference compositions comprise a recombinant receptor produced by the same process or substantially the same process; and
(b) determining the presence, absence or level of variance of the average mass spectrometry profile.

19. The method of embodiment 18, further comprising selecting the process for producing an engineered cell composition if the variance of the mass spectrometry profile among the plurality of the reference compositions is no more than 40%, no more than 30%, no more than 20%, no more than 10% or no more than 5%, or varies by such average by no more than one standard deviation among data components of the mass spectrometry profile.

20. The method of embodiment 18 or embodiment 19, wherein the average mass spectroscopy profile is of a sample of based on each of a plurality of reference engineered compositions or a subset thereof, wherein each of the plurality of reference engineered cell compositions is selected from (1) cells in a reference engineered composition, (2) CD3+ cells in a reference engineered composition; (3) CD4+ T cells in a reference engineered composition; (4) CD8+ T cells in a reference engineered composition; (5) recombinant receptor+ cells in a reference engineered composition; (6) recombinant receptor+CD3+ cells in a reference engineered composition, (7) recombinant receptor+CD8+ cells in a reference engineered composition, or (8) recombinant receptor+CD4+ cells in a reference engineered composition.

21. The method of embodiment 18 or embodiment 19, wherein each of the plurality of reference compositions is produced by a process comprising:
(i) selecting or isolating immune cells from a sample from a subject, thereby generating a source composition, optionally wherein the biological sample is a leukapheresis sample, apheresis sample or a whole blood sample;
(ii) incubating the cells of the source composition with a stimulatory reagent, thereby generating a stimulated composition, wherein the incubating is optionally carried out in the presence of one or more cytokines;
(iii) introducing a nucleic acid encoding the recombinant receptor into immune cells of the stimulated composition, thereby generating a transformed composition; and
(iv) culturing the stimulated composition at 37° C. for at least 24 hours, thereby generating the test engineered cell composition, wherein the culturing is optionally carried out in the presence of one or more cytokines.

22. The method of any of embodiments 1-17, wherein the test mass spectrometry profile and reference mass spectrometry profile individually is a peptide profile.

23. The method of any of embodiments 1-17 and 22, wherein the reference mass spectrometry profile is determined using the same mass spectrometry technique as the test mass spectrometry profile.

24. A method for characterizing a process for producing genetically engineered cell composition, the method comprising:
(a) determining a first mass spectrometry profile of a sample from a first cell composition or a subset thereof using a mass spectrometry technique;
(b) determining a second mass spectrometry profile of a sample from a second cell composition or a subset thereof using a mass spectrometry technique; and
(c) identifying one or more differences in the presence, absence or level of a least one data component in the first mass spectrometry profile compared to the second mass spectrometry profile,
wherein the first cell composition and second cell composition comprise compositions at different stages of a manufacturing process for producing genetically engineered cell composition.

25. The method of embodiment 24, wherein the first and second cell compositions are at different stages of generating a genetically engineered cell composition and are selected from:
(i) a source composition comprising immune cells selected or isolated from a biological sample from a subject, optionally wherein the biological sample is a leukapheresis sample, apheresis sample or a whole blood sample;
(ii) a stimulated composition comprising immune cells of the selected composition that have been contacted with a stimulatory reagent, optionally wherein the contacting was carried out in the presence of one or more cytokines;
(iii) a transformed composition comprising cells of the stimulated composition comprising a nucleic acid encoding the recombinant receptor; and
(iv) a cultured composition comprising cells of the transformed composition that have been cultured at or about 37° C. for at least 24 hours, optionally wherein the culturing is carried out in the presence of one or more cytokines.

26. The method of embodiment 24 or embodiment 25, wherein the first cell composition is a composition from a prior stage or prior timepoint of the manufacturing process compared to the second cell composition.

27. A method for characterizing a process for producing genetically engineered cell composition, the method comprising:
(a) determining a first mass spectrometry profile of a sample from a first cell composition or a subset thereof using a mass spectrometry technique;
(b) determining a second mass spectrometry profile of a sample from a second cell composition or a subset thereof using a mass spectrometry technique; and
(c) identifying one or more differences in the presence, absence or level of at least one data component in the first mass spectrometry profile compared to the second mass spectrometry profile,
wherein the first cell composition and second cell composition comprise genetically engineered cells produced by different processes.

28. The method of embodiment 27, wherein the different processes differ in one or more of the presence or concentration of serum; time in culture; lot of reagent; handling or storage of a reagent; presence or amount of a stimulatory reagent; the type of a stimulatory reagent; presence or amount of one or more cytokines; presence or amount of amino acids; temperature; the source or immune cell types of a source composition; the ratio or percentage of immune cell types in a source composition, optionally the CD4+/CD8+ cell ratio; cell density; static culture; rocking culture; perfusion; the type of viral vector; the vector copy number; the presence of a transduction adjuvant; cell density of a source composition in cryopreservation; the extent of expression of the recombinant receptor; or the presence of a compound to modulate cell phenotype.

29. The method of any of embodiments 24-28, wherein the first mass spectrometry profile and the second mass spectrometry profile individually is a peptide profile.

30. The method of any of embodiments 24-29, wherein the first mass spectrometry profile and the second mass spectrometry profile is determined using the same mass spectrometry technique.

31. A method of characterizing a recombinant receptor, the method comprising obtaining a mass spectrometry profile of a recombinant receptor, using a mass spectrometry technique, of a sample from a test engineered cell composition or a subset thereof comprising immune cells expressing or comprising the recombinant receptor, said mass spectrometry profile comprising at least one data component.

32. The method of embodiment 31, further comprising identifying one or more differences in the at least one data component compared to a mass spectrometry profile of the same cells but not expressing the recombinant receptor.

33. The method of embodiment 31 or embodiment 32, wherein the test engineered cell composition has been stimulated in the presence of a stimulatory reagent.

34. The method of any of embodiments 31-33, wherein the engineered cell composition comprises cells that have been contacted by an agent to produce a recombinant receptor-dependent activity, optionally wherein the agent is a target antigen that is capable of being bound by the recombinant receptor or is an anti-idiotypic antibody specific to the antibody.

35. The method of any of embodiments 31-34, further comprising identifying one or more differences in the mass spectrometry profile compared to a mass spectrometry of the same engineered cell composition but that has not been stimulated in the presence of a stimulatory reagent or has been stimulated in the presence of a different stimulatory reagent.

36. The method of any of embodiments 1-35, wherein the cell composition is enriched in the immune cells.

37. The method of any of embodiments 1-36, wherein the immune cells comprise lymphocytes.

38. The method of embodiment 37, wherein the lymphocytes comprise T cells or Natural Killer (NK) cells.

39. The method of embodiment 38, wherein the lymphocytes comprise T cells and the T cells are CD4+ and/or CD8+ T cells.

40. The method of any of embodiments 1-39, wherein the immune cells are human.

41. The method of any of embodiments 4, 21, 25 and 28-40, wherein the immune cells are T cells, optionally CD4+ and/or CD8+ T cells, and the stimulatory reagent is capable of activating one or more intracellular signaling domains of one or more components of a TCR complex and/or one or more intracellular signaling domains of one or more costimulatory molecules.

42. The method of embodiment 41, wherein the stimulatory reagent comprises a primary agent that specifically binds to a member of a TCR complex and a secondary agent that specifically binds to a T cell costimulatory molecule.

43. The method of embodiment 42, wherein the primary agent specifically binds to CD3 and/or the costimulatory molecule is selected from the group consisting of CD28, CD137 (4-1-BB), OX40, or ICOS.

44. The method of any of embodiments of any of embodiments 4, 21, 25 and 28-43, wherein stimulatory reagent comprises an anti-CD3 antibody or antigen binding fragment thereof and an anti-CD28 antibody or an antigen-binding fragment thereto.

45. The method of any of embodiments 42-44, wherein the primary and secondary agents are present on the surface of a solid support, optionally wherein the solid support is a bead.

46. The method of any of embodiments 42-44, wherein the primary and secondary agents are present on the surface of a soluble oligomeric reagent comprising a streptavidin or a streptavidin mutein.

47. The method of any of embodiments 4, 21, 25 and 28-46, wherein the culturing is carried out under conditions to promote proliferation and/or expansion of the engineered cells.

48. The method of any of embodiments 1-47, wherein the sample is processed from the test engineered cell composition by labeling one or more surface proteins, lysing cells, and isolating the one or more proteins.

49. The method of embodiment 48, further comprising digesting the one or more isolated proteins.

50. A method of assessing surface proteins of an engineered cell composition, the method comprising:
(a) labeling one or more surface proteins present on cells of an engineered cell composition or a subset thereof, the engineered cell composition comprising cells expressing or comprising a recombinant receptor, thereby generating a labeled cell composition;
(b) lysing cells of the labeled cell composition, thereby generating a lysed cell composition;
(c) isolating the one or more surface proteins form the lysed cell composition to obtain one or more isolated proteins; and
(d) subjecting the one or more isolated proteins to a mass spectrometry technique to obtain a mass spectrometry profile comprising one or more data components.

51. The method of embodiment 50, wherein prior to (d) further comprising digesting the one or more isolated proteins.

52. The method of embodiment 49 or embodiment 51, wherein the digestion is carried out by proteolysis in the presence of one or more protease that is capable of cleaving one or more peptide bonds.

53. The method of embodiment 52, wherein the one or more protease is or comprises trypsin.

54. The method of any of embodiments 48-53, wherein the one or more proteins comprise cell surface membrane proteins.

55. The method of any of embodiments 48-54, wherein the lysing the cells comprises incubation in the presence of a detergent.

56. The method of embodiment 55, wherein the detergent is a nonionic detergent.
57. The method of embodiment 56, wherein the detergent is or comprises an effective amount of Triton X-100.
58. The method of embodiment 55, wherein the detergent is a denaturing detergent.
59. The method of embodiment 58, wherein the denaturing detergent is or comprises an effective amount of Sodium dodecyl sulfate (SDS).
60. The method of ay of embodiments 55-59, wherein after the lysing the cells, the method further comprises removing the detergent from the lysed composition.
61. The method of any of embodiments 48-60, wherein the labeling the surface proteins comprises biotin labeling of primary amines.
62. The method of embodiment 61, wherein the one or more proteins are isolated using a reagent comprising avidin, streptavidin, NeutrAvidin™ or CaptAvidin™.
63. The method of any of embodiments 1-62, wherein the mass spectrometry technique comprises subjecting the sample to liquid chromatography (LC) followed by mass spectrometry.
64. The method of embodiment 63, wherein the liquid chromatography is high performance liquid chromatography (HPLC), ultra-high performance liquid chromatography (UHPLC), or ultra performance liquid chromatography (UPLC).
65. The method of embodiment 63 or embodiment 64, wherein the liquid chromatography is ultra performance liquid chromatography (UPLC).
66. The method of any of embodiments 63-65, wherein the liquid chromatography and mass spectrometry are carried out online.
67. The method of any of embodiments 63-66, wherein the liquid chromatography is selected from normal phase (NP-), reverse phase (RP) and hydrophilic interaction chromatography (HILIC).
68. The method of any of embodiments 63-67, wherein the mass spectrometer that performs the mass spectrometry comprises one or more of a quadrupole, ion trap, time of flight (TOF), or Fourier transform ion cyclotron resonance mass analyzer.
69. The method of embodiment 68, wherein the mass spectrometer comprises an ion trap mass analyzer that is a three-dimensional quadrupole ion trap, a cylindrical ion trap, a linear quadrupole ion trap, or an Orbitrap mass analyzer.
70. The method of embodiment 69, wherein the mass spectrometer is a quadrupole-Orbitrap mass spectrometer.
71. The method of any of embodiments 1-70, wherein the data components are selected from MS ion information, total ion chromatograph (TIC) or a portion thereof, extracted ion chromatogram (XIC) or a portion thereof, peptide MS ion signal peak, protein MS ion signal peak, peptide identification information, protein identification information, qualitative information, quantitative information, structural information, post-translation modifications.
72. The method of embodiment 71, wherein the data component is an XIC or a portion thereof, wherein the XIC or portion thereof is based on one or more theoretical or known m/z values of one or more peptide components of the recombinant receptor.
73. The method of embodiment 72, wherein the one or more peptide components is a proteolytically cleaved or digested peptide component, optionally wherein the protease is trypsin.
74. The method of any of embodiments 1-73, wherein the recombinant receptor is or comprises a chimeric receptor and/or a recombinant antigen receptor.
75. The method of any of embodiments 1-76, wherein the recombinant receptor is capable of binding to a target antigen that is associated with, specific to, and/or expressed on a cell or tissue of a disease, disorder or condition.
76. The method of embodiment 75, wherein the disease, disorder or condition is an infectious disease or disorder, an autoimmune disease, an inflammatory disease, or a tumor or a cancer.
77. The method of embodiment 75 or embodiment 76, wherein the target antigen is a tumor antigen.
78. The method of any of embodiments 75-77, wherein the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Ra), IL-13 receptor alpha 2 (IL-βRα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

79. The method of any of embodiments 1-78, wherein the recombinant receptor is or comprises a functional non-TCR antigen receptor or a TCR or antigen-binding fragment thereof.

80. The method of any of embodiments 1-79, wherein the recombinant receptor is a chimeric antigen receptor (CAR).

81. The method of any of embodiments 1-80, wherein the sample is of the cell composition or a subset thereof selected from (1) cells in the cell composition, (2) CD3+ cells in the cell composition; (3) CD4+ T cells in the cell composition; (4) CD8+ T cells in the cell composition; (5) recombinant receptor+ cells in the cell composition; (6) recombinant receptor+CD3+ cells in the cell composition, (7) recombinant receptor+CD8+ cells in the cell composition, or (8) recombinant receptor+CD4+ cells in the cell composition, optionally wherein the recombinant receptor is a CAR.

82. An engineered cell composition, wherein the engineered cell composition is produced by a process in which the mass spectrometry profile, obtaining using a mass spectroscopy technique, of a sample from the engineered cell composition or a subset thereof varies by no more than 40%, no more than 30%, no more than 20%, no more than 10% or no more than 5% among the average mass spectrometry profile of a plurality of engineered cell compositions produced by the process, or varies by such average by no more than one standard deviation among data components of the mass spectrometry profile.

83. The engineered cell composition of embodiment 82, wherein the engineered cell composition comprises a recombinant receptor.

84. The engineered cell composition of embodiment 82 or embodiment 83, wherein the engineered cell composition comprises immune cells.

85. The engineered cell composition of embodiment 84, wherein the process for producing the engineered cell composition comprises:
(i) selecting or isolating immune cells from a sample from a subject, thereby generating a source composition, optionally wherein the biological sample is a leukapheresis sample, apheresis sample or a whole blood sample;
(ii) incubating the cells of the source composition with a stimulatory reagent, thereby generating a stimulated composition, wherein the incubating is optionally carried out in the presence of one or more cytokines;
(iii) introducing a nucleic acid encoding the recombinant receptor into immune cells of the stimulated composition, thereby generating a transformed composition; and
(iv) culturing the stimulated composition at 37° C. for at least 24 hours, thereby generating the test engineered cell composition, wherein the culturing is optionally carried out in the presence of one or more cytokines.

86. The engineered cell composition of embodiment 84 or embodiment 85, wherein the cell composition is enriched in the immune cells.

87. The engineered cell composition of any of embodiments 84-86, wherein the immune cells comprise lymphocytes.

88. The engineered cell composition of embodiment 87, wherein the lymphocytes comprise T cells or Natural Killer (NK) cells.

89. The engineered cell composition of embodiment 88, wherein the lymphocytes comprise T cells and the T cells are CD4+ and/or CD8+ T cells.

90. The engineered cell composition of any of embodiments 84-89, wherein the immune cells are human.

91. The engineered cell composition of any of embodiments 85-90, wherein the immune cells are T cells, optionally CD4+ and/or CD8+ T cells, and the stimulatory reagent is capable of activating one or more intracellular signaling domains of one or more components of a TCR complex and/or one or more intracellular signaling domains of one or more costimulatory molecules.

92. The engineered cell composition of embodiment 91, wherein the stimulatory reagent comprises a primary agent that specifically binds to a member of a TCR complex and a secondary agent that specifically binds to a T cell costimulatory molecule.

93. The engineered cell composition of embodiment 92, wherein the primary agent specifically binds to CD3 and/or the costimulatory molecule is selected from the group consisting of CD28, CD137 (4-1-BB), OX40, or ICOS.

94. The engineered cell composition of any of embodiments of any of embodiments 85-93, wherein stimulatory reagent comprises an anti-CD3 antibody or antigen binding fragment thereof and an anti-CD28 antibody or an antigen-binding fragment thereto.

95. The engineered cell composition of any of embodiments 92-94, wherein the primary and secondary agents are present on the surface of a solid support, optionally wherein the solid support is a bead.

96. The engineered cell composition of any of embodiments 92-95, wherein the primary and secondary agents are present on the surface of a soluble oligomeric reagent comprising a streptavidin or a streptavidin mutein.

97. The engineered cell composition of any of embodiments 85-96, wherein the culturing is carried out under conditions to promote proliferation and/or expansion of the engineered cells.

98. The engineered cell composition of any of embodiments 82-97, wherein the sample is processed from the engineered cell composition by labeling one or more surface proteins, lysing cells, and isolating the one or more proteins.

99. The engineered cell composition of embodiment 98, further comprising digesting the one or more isolated proteins.

100. The engineered cell composition of embodiment 98 or embodiment 99, wherein the digestion is carried out by proteolysis in the presence of one or more protease that is capable of cleaving one or more peptide bonds.

101. The engineered cell composition of embodiment 100, wherein the one or more protease is or comprises trypsin.

102. The engineered cell composition of any of embodiments 98-101, wherein the one or more proteins comprise cell surface membrane proteins.

103. The engineered cell composition of any of embodiments 98-102, wherein the lysing the cells comprises incubation in the presence of a detergent.
104. The engineered cell composition of embodiment 55, wherein the detergent is a nonionic detergent.
105. The engineered cell composition of embodiment 104, wherein the detergent is or comprises an effective amount of Triton X-100.
106. The engineered cell composition of embodiment 105, wherein the detergent is a denaturing detergent.
107. The engineered cell composition of embodiment 106, wherein the denaturing detergent is or comprises an effective amount of Sodium dodecyl sulfate (SDS).
108. The engineered cell composition of any of embodiments 98-107, wherein after the lysing the cells, the method further comprises removing the detergent from the lysed composition.
109. The engineered cell composition of any of embodiments 98-108, wherein the labeling the surface proteins comprises biotin labeling of primary amines.
110. The engineered cell composition of embodiment 109, wherein the one or more proteins are isolated using a reagent comprising avidin, streptavidin, NeutrAvidin™ or CaptAvidin™.
111. The engineered cell composition of any of embodiments 82-110, wherein the mass spectrometry technique comprises subjecting the sample to liquid chromatography (LC) followed by mass spectrometry.
112. The engineered cell composition of embodiment 111, wherein the liquid chromatography is high performance liquid chromatography (HPLC), ultra-high performance liquid chromatography (UHPLC), or ultra performance liquid chromatography (UPLC).
113. The engineered cell composition of embodiment 111 or embodiment 112, wherein the liquid chromatography is ultra performance liquid chromatography (UPLC).
114. The engineered cell composition of any of embodiments 111-113, wherein the liquid chromatography and mass spectrometry are carried out online.
115. The engineered cell composition of any of embodiments 111-114, wherein the liquid chromatography is selected from normal phase (NP-), reverse phase (RP) and hydrophilic interaction chromatography (HILIC).
116. The engineered cell composition of any of embodiments 111-115, wherein the mass spectrometer that performs the mass spectrometry comprises one or more of a quadrupole, ion trap, time of flight (TOF), or Fourier transform ion cyclotron resonance mass analyzer.
117. The engineered cell composition of embodiment 116, wherein the mass spectrometer comprises an ion trap mass analyzer that is a three-dimensional quadrupole ion trap, a cylindrical ion trap, a linear quadrupole ion trap, or an Orbitrap mass analyzer.
118. The engineered cell composition of embodiment 117, wherein the mass spectrometer is a quadrupole-Orbitrap mass spectrometer.
119. The engineered cell composition of any of embodiments 82-118, wherein the data components are selected from MS ion information, total ion chromatograph (TIC) or a portion thereof, extracted ion chromatogram (XIC) or a portion thereof, peptide MS ion signal peak, protein MS ion signal peak, peptide identification information, protein identification information, qualitative information, quantitative information, structural information, post-translation modifications.
120. The engineered cell composition of embodiment 119, wherein the data component is an XIC or a portion thereof, wherein the XIC or portion thereof is based on one or more theoretical or known m/z values of one or more peptide components of the recombinant receptor.
121. The engineered cell composition of embodiment 120, wherein the one or more peptide components is a proteolytically cleaved or digested peptide component, optionally wherein the protease is trypsin.
122. The engineered cell composition of any of embodiments 82-121, wherein the recombinant receptor is or comprises a chimeric receptor and/or a recombinant antigen receptor.
123. The engineered cell composition of any of embodiments 82-122, wherein the recombinant receptor is capable of binding to a target antigen that is associated with, specific to, and/or expressed on a cell or tissue of a disease, disorder or condition.
124. The engineered cell composition of embodiment 123, wherein the disease, disorder or condition is an infectious disease or disorder, an autoimmune disease, an inflammatory disease, or a tumor or a cancer.
125. The engineered cell composition of embodiment 123 or embodiment 124, wherein the target antigen is a tumor antigen.
126. The engineered cell composition of any of embodiments 123-125, wherein the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Ra), IL-13 receptor alpha 2 (IL-βRα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

127. The engineered cell composition of any of embodiments 82-126, wherein the recombinant receptor is or comprises a functional non-TCR antigen receptor or a TCR or antigen-binding fragment thereof.

128. The engineered cell composition of any of embodiments 8, wherein the recombinant receptor is a chimeric antigen receptor (CAR).

129. A method of evaluating a reagent used in the process of producing an engineered cell composition, the method comprising:
(a) comparing a mass spectrometry profile of a sample from a first reagent to a reference mass spectrometry profile of the reagent, wherein the mass spectrometry profile is obtained using a mass spectrometry technique; and
(c) identifying one or more differences in the presence, absence or level of at least one data component in the test mass spectrometry profile compared to the reference mass spectrometry profile, thereby identifying a mass spectrometry profile of the reagent.

130. The method of embodiment 129, wherein the reference mass spectrometry profile is of a sample from a reference reagent or is an average mass spectra profile of a number of samples from a plurality of different lots of the reagent.

131. The method of embodiment 130, wherein the reference mass spectrometry profile is an average mass spectrometry profile of a sample of a plurality of different lots of the reagent.

132. The method of embodiment 131, further comprising determining the presence, absence or level of variance of mass spectrometry profile of the sample to the average mass spectrometry profile.

133. The method of embodiment 132, further comprising selecting a reagent if the variance of the mass spectrometry profile among the plurality of the different lots of the reagent is no more than 40%, no more than 30%, no more than 20%, no more than 10% or no more than 5%, or varies by such average by no more than one standard deviation among data components of the mass spectrometry profile.

134. The method of any of embodiments 129-133, wherein the mass spectrometry technique comprises subjecting the sample to liquid chromatography (LC) followed by mass spectrometry.

135. The method of embodiment 134, wherein the liquid chromatography is high performance liquid chromatography (HPLC), ultra-high performance liquid chromatography (UHPLC), or ultra performance liquid chromatography (UPLC).

136. The method of embodiment 135 or embodiment 135, wherein the liquid chromatography is ultra performance liquid chromatography (UPLC).

137. The method of any of embodiments 134-136, wherein the liquid chromatography and mass spectrometry are carried out online.

138. The method of any of embodiments 134-137, wherein the liquid chromatography is selected from normal phase (NP-), reverse phase (RP) and hydrophilic interaction chromatography (HILIC).

139. The method of any of embodiments 134-138, wherein the mass spectrometer that performs the mass spectrometry comprises one or more of a quadrupole, ion trap, time of flight (TOF), or Fourier transform ion cyclotron resonance mass analyzer.

140. The method of embodiment 139, wherein the mass spectrometer comprises an ion trap mass analyzer that is a three-dimensional quadrupole ion trap, a cylindrical ion trap, a linear quadrupole ion trap, or an Orbitrap mass analyzer.

141. The method of embodiment 140, wherein the mass spectrometer is a quadrupole-Orbitrap mass spectrometer.

142. The method of any of embodiments 129-410, wherein the data components are selected from MS ion information, total ion chromatograph (TIC) or a portion thereof, extracted ion chromatogram (XIC) or a portion thereof, peptide MS ion signal peak, protein MS ion signal peak, peptide identification information, protein identification information, qualitative information, quantitative information, structural information, post-translation modifications.

143. The method of any of embodiments 129-142, wherein the reagent is a reagent capable of stimulating a signal in cells of a cell composition, optionally a T cell composition.

144. The method of embodiment 143, wherein the cells of the cell composition comprise a recombinant receptor, optionally a chimeric antigen receptor.

145. The method of embodiment 144, wherein the reagent is capable of stimulating or inducing a recombinant receptor-dependent activity in cells of the cell composition.

VI. Examples

The following examples are included for illustrative purposes only and are not intended to limit the scope of the invention.

Example 1: Analysis of Surface Protein Expression of T Cells by Mass Spectrometry Surface protein expression of cells collected prior to or after an exemplary engineering process for generating T cell compositions containing chimeric antigen receptors (CAR) expressing T cells were analyzed with liquid chromatography-tandem mass spectrometry (LC-MS/MS). Initial source T cell compositions enriched for CD4+ or CD8+ T cells were obtained from human leukapheresis samples by immunoaffinity-based enrichment and were cryofrozen. The CD4+ or CD8+ T cells were subsequently thawed, activated with anti-CD3/anti-CD28 paramagnetic beads, and transduced with a viral vector encoding an anti-CD19 CAR, followed by expansion and cryopreservation of the engineered cell compositions. The anti-CD19 CAR contained an anti-CD19 scFv derived from a murine antibody, an Ig-derived spacer, a human CD28-derived transmembrane domain, a human 4-1BB-derived intracellular signaling domain and a human CD3 zeta-derived signaling domain.

LC-MS/MS analyses were performed on peptide samples obtained following cell surface protein isolation of T cells samples of both the initial source and CAR+ engineered cell compositions. Briefly, T cell samples from cryopreserved initial source and CAR+ engineered cell compositions containing approximately 15-150×10$^6$ cells were thawed and washed. To label surface proteins via primary amines on the surface of intact cells, the cells were resuspended in a solution of sulfo-NHS-SS-Biotin prepared by adding ice-cold PBS to a vial of biotin (Pierce; Cat. No. 89881). Each resuspended cell sample was then transferred to a 25 cm$^2$ cell culture flask and an additional aliquot of the biotin solution was added to each sample. The cell culture flasks were then incubated on a shaker plate (300 rpm) at 4° C. for 30 minutes. For engineered cell composition samples, cell surface protein isolation was carried out by lysing the cells with a mild detergent, isolating the labeled proteins using an agarose-based affinity reagent (e.g. Thermo Scientific™ NeutrAvidin™ Agarose), and releasing the labeled proteins with sodium dodecyl sulfate (SDS) sample buffer (62.5 mM Tris-HCl, pH 6.8, 1% SDS, 10% glycerol) containing 50 mM DTT. For initial source cell composition samples, the cell surface proteins were eluted with 200 μL of sodium dodecyl sulfate (SDS) sample buffer.

Each initial source or engineered cell composition sample was then processed to remove surfactants by dialysis using a 10,000 nominal molecular weight limit (NMWL) filter with buffer exchange into 400 μL UA buffer (8M Urea in 0.1M Tris-HCl, pH 8.3) to reduce disulfide bonds, followed by addition of 100 μL of 50 mM iodoacetamide to alkylate free thiol groups on cysteines. After washing the filters with 100 μL of 50 mM ammonium bicarbonate/3 M urea followed by centrifugation several times, the samples were collected. In some cases, samples were pooled prior to performing the filtration procedure described above.

The resulting samples were then subjected to trypsin digestion overnight at 37° C. Following incubation, each digestion was quenched by adding 10% Trifluoroacetic acid (TFA).

Initial source and engineered cell composition samples were then concentrated as necessary (based on an initial assessment of peptide abundance using liquid chromatography) prior to mass spectrometry analysis). In some cases, samples were pooled prior to the concentration procedure described above. Each sample was analyzed via a tandem mass spectrometry method using a hybrid quadrupole Orbitrap mass spectrometer coupled to a liquid chromatograph. Mass spectrometry data was acquired using a data dependent acquisition technique (20 most abundant ions selected). Mass spectrometer settings included: MS$^1$ mass resolution of 120,000; MS$^1$ scan range of 325-2000 m/z; MS$^1$ AGC target of 5e5; 5 ppm accuracy inclusion list; MS$^2$ mass resolution of 30,000; MS$^2$ scan range of 200-2000 m/z; isolation window of 4 m/z; MS$^2$ AGC target of 1e5, and a fragmentation energy of 22 (NCE).

The datasets obtained from each LC-MS/MS analysis described above were analyzed using ProteomeDiscover Software (ThermoScientific v2.1) with the human proteome database obtained from UNIPROT and common Repository of Adventitious Proteins database obtained from the Global Proteome Machine. Search algorithm settings included: tryptic peptides; maximum missed cleavage of 2; minimum peptide length of 6; precursor mass tolerance of 10 ppm; fragment mass tolerance of 0.02 Da; dynamic modifications for oxidation of methionines and biotin labeling of lysines; static modifications for carboxymethylation of cysteines; use of decoys with 1% or less FDR; and 1% or less false discover rate (FDR).

Peptides were manually validated using a 5 ppm extracted ion chromatogram and visual MS$^2$ fingerprint.

FIG. 1A is an exemplary image of a total ion chromatograms (TIC) from an LC-MS/MS analysis of an initial source cell composition sample (lower half) and a TIC from an LC-MS/MS analysis of a corresponding engineered cell composition sample (upper half). As shown in FIG. 1A, differences in peaks were observed corresponding to differences in peptide ions of cell surface proteins between the initial source and engineered cell compositions. Using the LC-MS/MS technique described above, 1406 total cell surface proteins were identified, including 397 proteins that were unique to the source cell composition and 223 proteins that were unique to the engineered cell composition.

These data are consistent with a capability of LC-MS/MS analysis to distinguish between surface protein expression profiles of T cell compositions collected at different stages of a genetic engineering process.

Figure 1B:
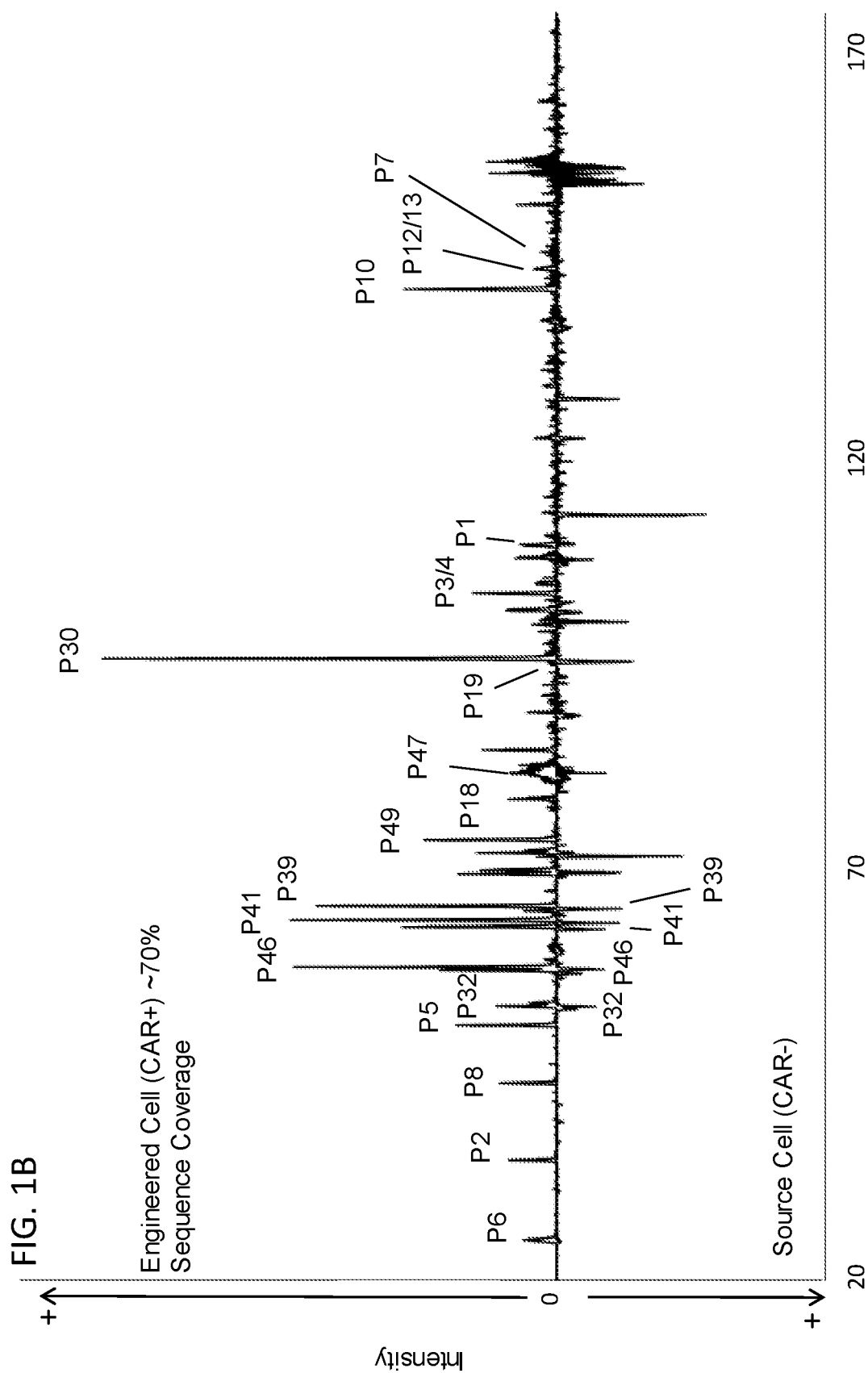

An extracted ion chromatogram (XIC) was generated by separating the ions associated with the anti-CD19 CAR using theoretical tryptic peptide masses of components of the CAR (with a 5 ppm tolerance from theoretical), and were compared in both the initial source and engineered T cell compositions. FIG. 1B depicts an exemplary combined XIC image of an initial source cell composition sample (lower half) and a corresponding CAR+ engineered cell composition sample (upper half). Peptide peaks associated with extracellular and intracellular portions of the CAR were identified, with peaks P1 through P19 representing the extracellular region. Differences in peaks were observed in the XIC obtained from the engineered cell composition, which included CAR expressing T cells, as compared to the initial source cells that did not contain CAR expressing cells (FIG. 1B). Some peaks associated with the anti-CD19 CAR were observed in the XIC obtained from the initial source cells, consistent with components of the CAR also being expressed as part of endogenous proteins, e.g., CD3 zeta signaling domain.

Example 2: Analysis of Reagents for a CAR T Cell Engineering Process by Mass Spectrometry It has been observed that in some cases, changes of storage or handling conditions of raw material(s) or reagent(s) or different lots of raw material(s) or reagent(s) used in a process for producing an engineered T cell composition—in an otherwise similar cell engineering process—may correlate, in the final engineered composition, with certain parameters associated with altered or varied activity of the engineered T cell product.

Different lots of an exemplary raw material used in a process for generating a CAR+ engineered T cell composition, and that was identified as a reagent that required titration in the process due to variability between and among lots, was analyzed by LC-MS/MS to assess the presence or absence of differences between the lots. The raw material was known or suspected of containing three different proteins. Samples of the reagent were taken from three different manufacturing lots that each met the vendor's release criteria. The proteins were isolated from the reagent and analyzed by LC-MS/MS in a similar process as described in Example 1.

Figure 2:
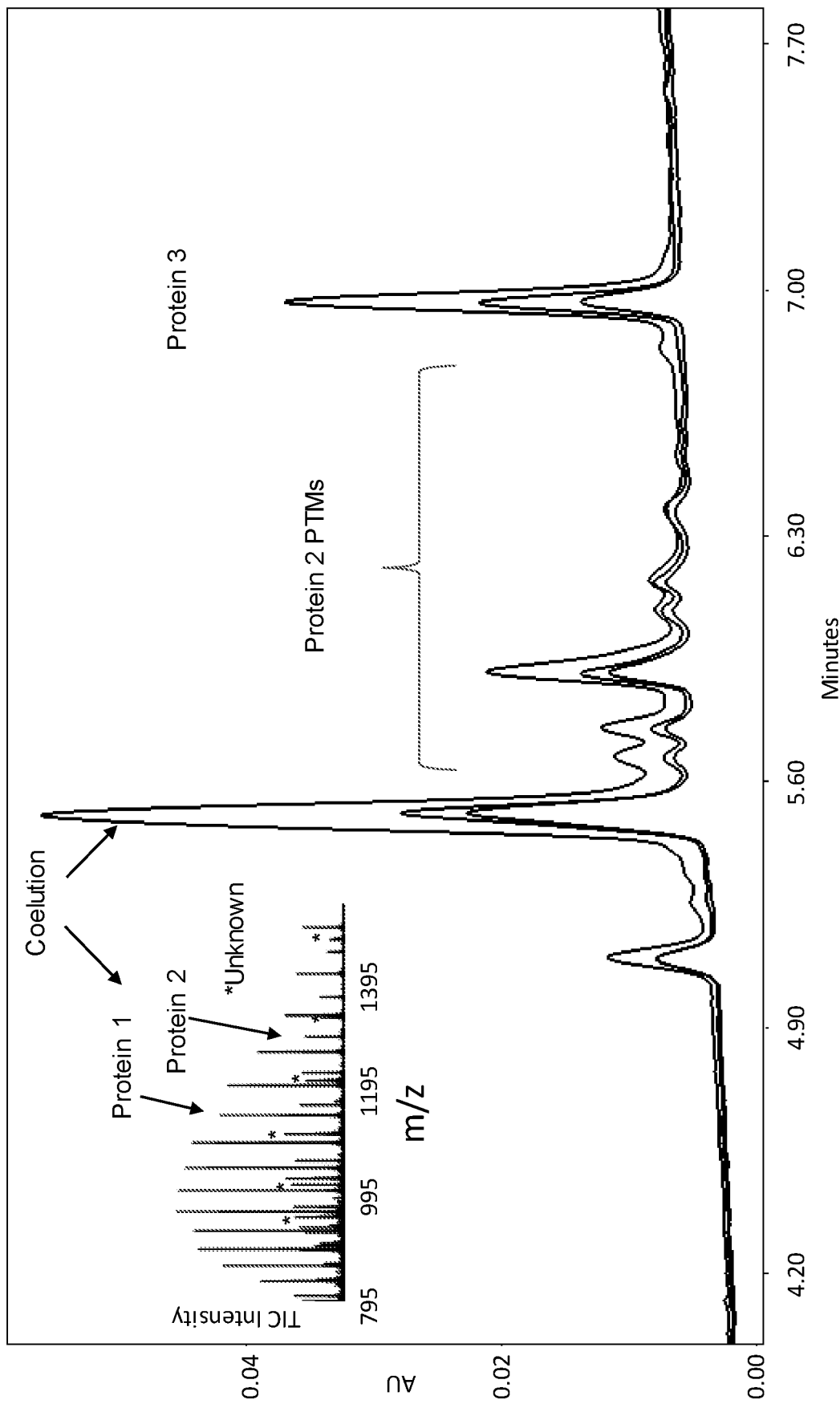
FIG. 2 depicts LC analysis profiles for three individual proteins present in a reagent, including a protein with post-translational modification (PTM) isolated from three different lots of an exemplary raw material used in a process for generating engineered (CAR+) T cell compositions, and mass-to-charge ratios (m/z) for coeluted proteins.

Proteins were separated by reversed phase chromatography. As shown in FIG. 2, different profiles were observed between the three different lots consistent with a difference in the relative amounts or properties of the proteins between lots. LC analysis alone, however, demonstrated the coelution of several proteins. To distinguish proteins that coeluted, mass-to-charge ratios (m/z) were preselected and detected in the analysis (FIG. 2, top left corner). As shown in the inset of FIG. 2, the different coeluted proteins were able to be separately detected, demonstrating utility of this method to identify differences among reagent lots containing proteins whose amounts or properties (e.g. post-translational modification) may differ.

Figure 3:
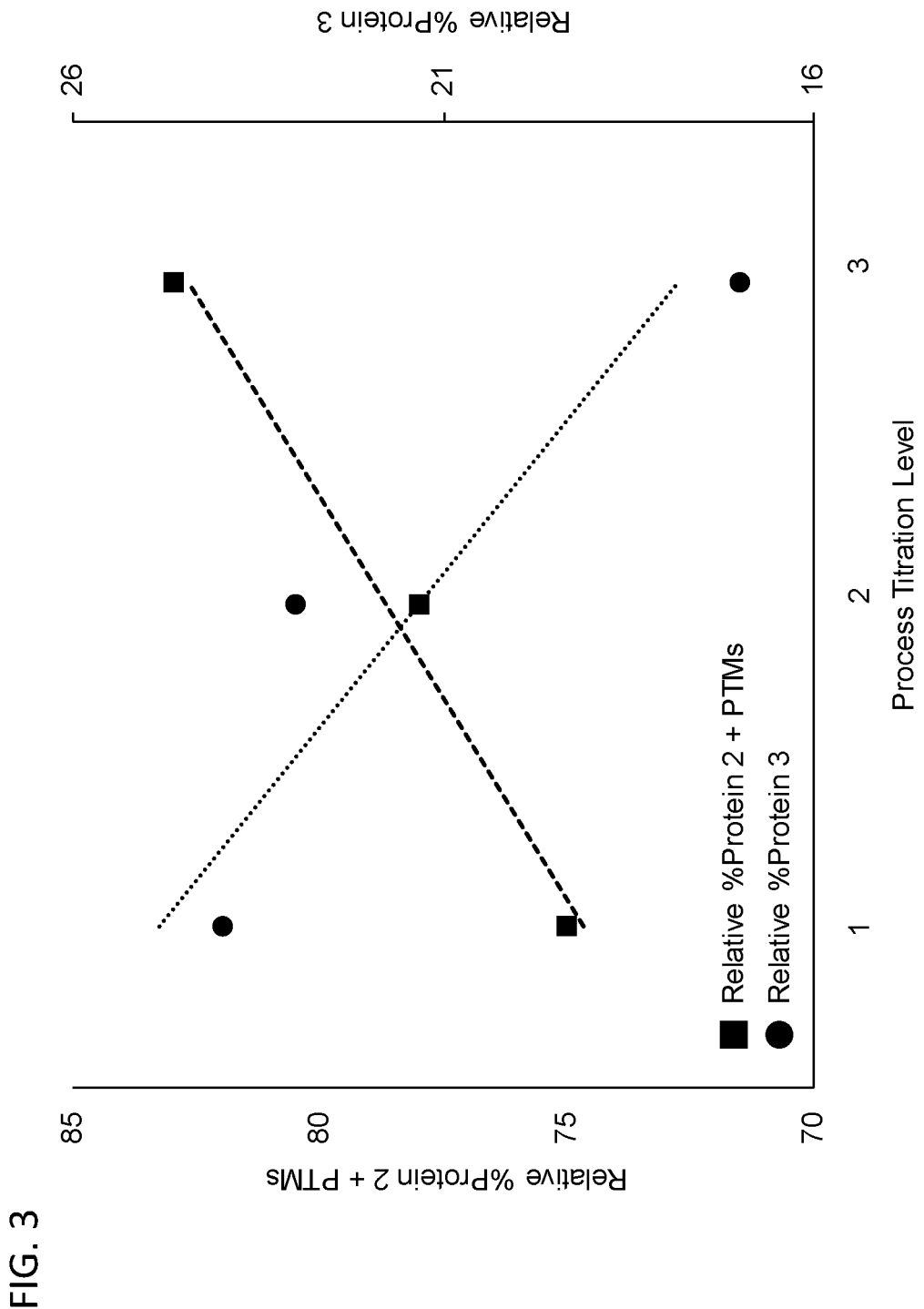
FIG. 3 depicts mass spectrometry analysis of the relative percentage of Protein 2 (with post-translational modifications (PTMs)) and Protein 3 in three different titration samples of the raw reagent used in a process for generating engineered (CAR+) T cell compositions.

Samples of the raw reagent at three different titration levels were further analyzed for two of the proteins that were suspected as most likely to impact the process for producing an engineered T cell composition. The relative percentage of each of the two proteins in each of the titrated samples was quantitated. As shown in FIG. 3, analysis of the reagent components by mass spectrometry indicated that the relative percentage of the second protein (plus post-translational modifications, PTM, of the second protein) of the reagent were inversely correlated to the relative percentage of a third protein. These results are consistent with a proposed combination effect of the third protein and the second protein in the CAR T cell engineering process as shown by the inverse correlation of their relative amounts at the different titration levels. Taken together, these results are consistent with a use of mass spectrometry, in combination with knowledge of the biological relevance of protein components to the engineering process, to assist with the identification of lot to lot variability of reagents and potential impact on manufacturing processes.

Example 3: Mapping Surface N-Linked Glycans of a Cell Composition

To map the cell surface N-linked glycan profile of a cell composition, exemplary cryopreserved T cell compositions containing cells expressing a chimeric antigen receptor (CAR) were individually thawed, diluted 1:10 in cell culture media heated to 37° C., and a sample of 1-2.5×10$^6$ cells was transferred to a fresh tube.

The transferred cell sample was centrifuged and washed in phosphate buffered saline (PBS), followed by reconstitution of the cell suspension with approximately 198 µL PBS. Approximately 2 µL PNGase F PRIME (N-Zyme Scientifics; available from Bulldog Bio, Catalog No. NZPP050) was added to the cell suspension containing whole, intact cells, followed by incubation for 30 minutes at 37° C. with gentle mixing. To obtain released surface N-glycans, the cell suspension was centrifuged and the supernatant was collected into a clean tube that was immediately evaporated to dryness with vacuum centrifugation.

5 µL of a labeling reagent composed of an N-hydroxysuccinimide (NHS) carbamate tagging group, a quinolone fluorophore, and a basic tertiary amine (e.g. Glycoworks™ RapiFluor-MS™ label) was added. The sample was mixed, incubated for approximately 5 minutes at room temperature, following by quenching of the label by adding approximately 365 µL acetonitrile to the sample. The sample was mixed and centrifuged. Solid phase extraction (SPE) was carried out on the sample to further clean up the N-glycans prior to further analysis. The N-glycan sample was evaporated to dryness with a vacuum centrifuge and then resuspended in appropriate diluent for analysis.

Glycans were separated using HILIC liquid chromatography and detected by fluorescence (Waters ACQUITY I-Class) (HILIC-FLR) and tandem mass spectrometry (positive electrospray ionization (ESI), Q-Exactive™ HF (Thermo Scientific)), i.e., HILIC-ESI-MS/MS, for relative quantification and identification.

Figure 4A:
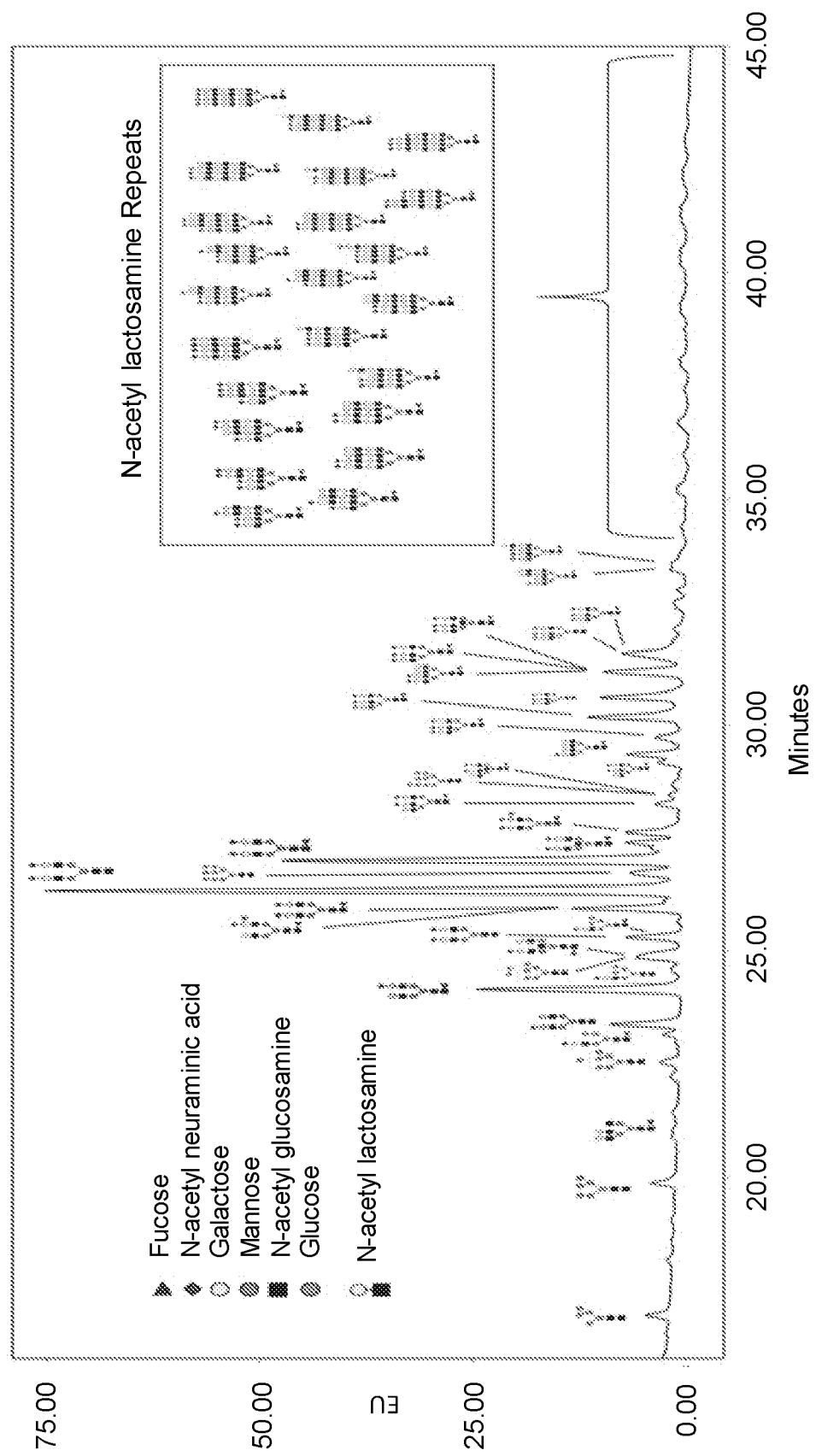
FIGS. 4A-C show chromatograms produced by HILIC-LC and tandem MS of N-glycans releases from whole intact CD3+ activated T cells following PNGase F treatment.

As shown in FIG. 4A, the annotated HILIC-FLR chromatogram revealed that the cell surface N-glycan map of anti-CD3/anti-CD28 activated CD3+ cells was a complex mixture of glycan types.

Figure 4B:
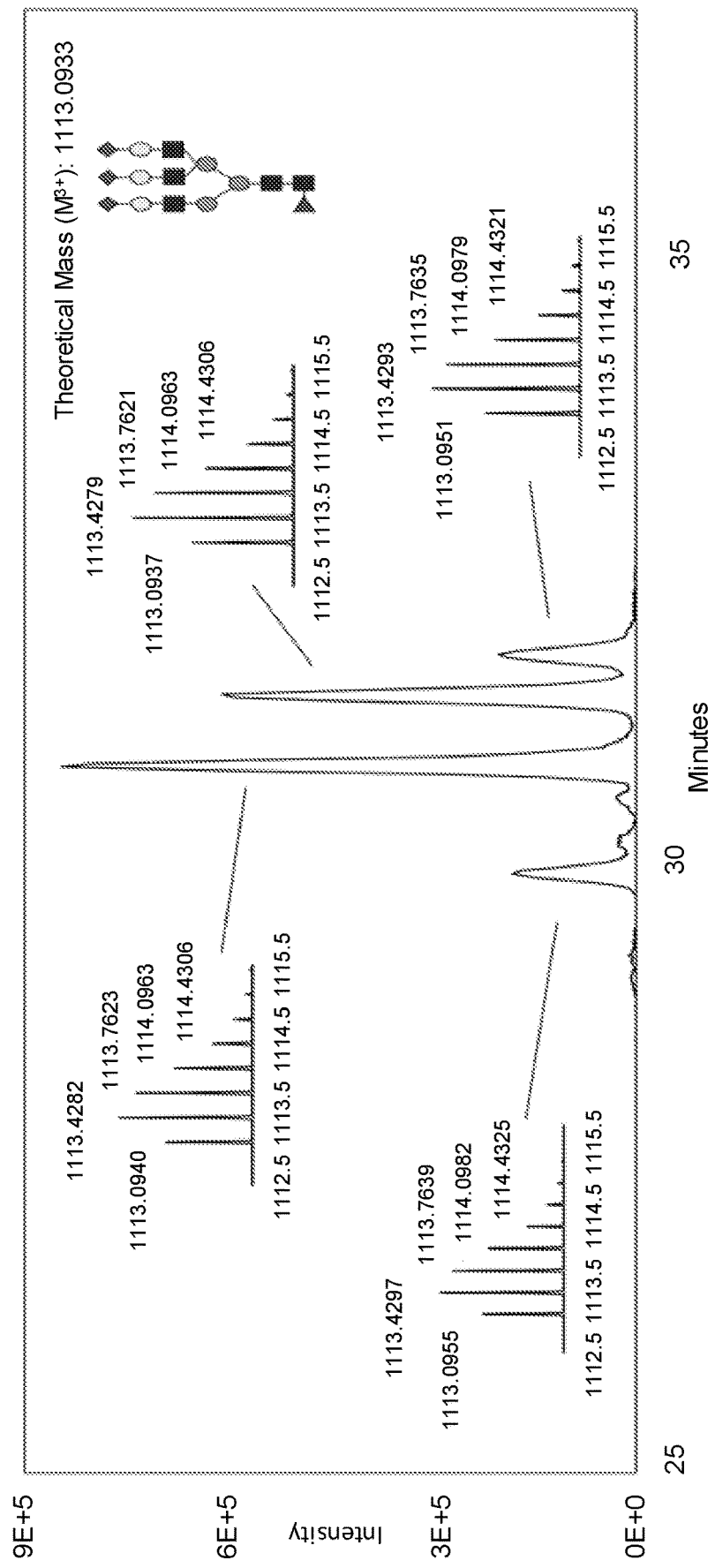
Figure 4C:
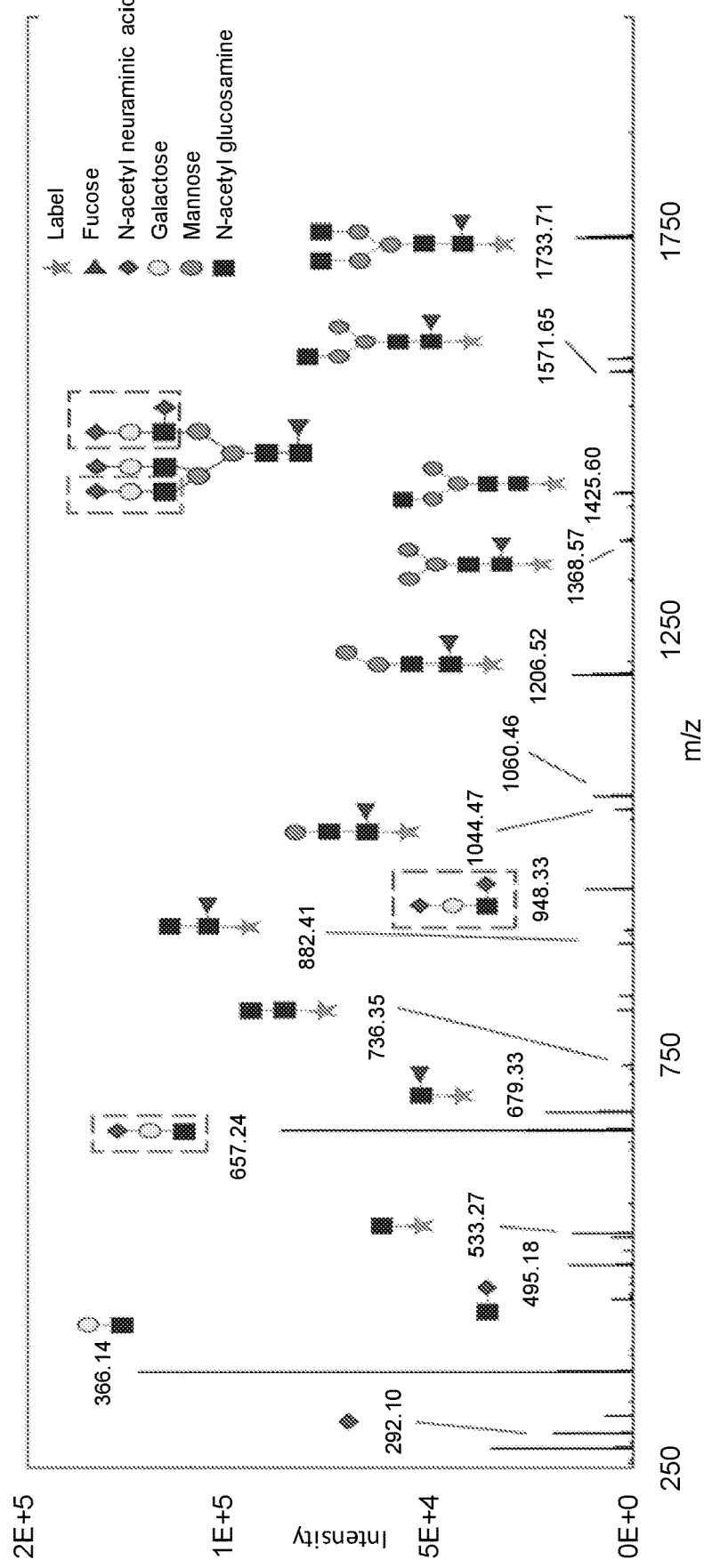

For tandem mass spectrometry (MS/MS), particles were ionized by ESI and separated by their mass-to-charge ratio at the first stage of the mass spectrometry. FIG. 4B depicts an extracted ion chromatogram (XIC) produced from the first stage of mass spectrometry for the exemplary A3S3F N-glycan in the +3 charged state using a 5 ppm mass tolerance. Multiple chromatographic peaks of the N-glycan with identical isotopic distributions were observed, which is consistent with the likely presence of linkage differences between the monosaccharide units of the glycan structure. After the first stage, the glycans underwent fragmentation and the resulting fragments were separated and measured in the second stage of the MS/MS. The MS/MS fragmentation of the exemplary N-glycan A3S4F, fragmented by high energy collisional dissociation (HCD) at a normalized collision energy (NCE) of 15, is shown in FIG. 4C. Combined with the high resolution MS data of the first stage, the fragmentation of A3S4F confirmed the presence of an n-actyl neuraminic acid linkage at the canonical terminal galactose residue, as well as at a unique site on an n-acetyl glucosamine residue of the same antennae (FIG. 4C, boxes). These results demonstrate that MS/MS combined with the high resolution MS data can identify glycan structures, including unique glycan structures, following separation and detection by HILIC-FLR.

Example 4: Identifying Changes in Glycotransferases by Mapping Surface N-Linked Glycans Surface N-linked glycans of a first and second cell composition are isolated and labeled similar to as described in Example 3. The N-glycans are separated with HILIC liquid chromatography and detected by fluorescence and mass spectrometry by HILIC-ESI-MS/MS for relative quantification and identification similar to as described in Example 3. Resulting N-glycan profiles of the first and second cell composition are compared to identify differences in the expression of individual N-glycans. Since specific glycotransferases genes are related to N-glycan linkage, the results are correlated to genomic data (such as by RNA-seq or Assay for Transposase-Accessible Chromatin using sequencing (ATAC-seq)) obtained from samples of the first and second compositions. The correlation identifies changes in glycotransferases gene expression that accompanies specific changes in surface N-glycan expression.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

| # | SEQUENCE | ANNOTATION |
|---|---|---|
| 1 | ESKYGPPCPPCP | spacer (IgG4hinge) (aa) |
| 2 | GAATCTAAGTACGGACCGCCCTGCCCCCCTTGCCCT | spacer (IgG4hinge) (nt) |
| 3 | ESKYGPPCPPCPGQPREPQVYTLPPSQEEMTKNQVSLTCLVKGFYPSD IAVEWESNGQPENNYKTTPPVLDSDGSFFLYSRLTVDKSRWQEGNVFS CSVMHEALHNHYTQKSLSLSLGK | Hinge-CH3 spacer |
| 4 | ESKYGPPCPPCPAPEFLGGPSVFLFPPKPKDTLMISRTPEVTCVVVDV SQEDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQ VSLTCLVKGFYPSDIAVEWESNGQPENNYKTTPPVLDSDGSFFLYSRL TVDKSRWQEGNVFSCSVMHEALHNHYTQKSLSLSLGK | Hinge-CH2-CH3 spacer |
| 5 | RWPESPKAQASSVPTAQPQAEGSLAKATTAPATTRNTGRGGEEKKKEK EKEEQEERETKTPECPSHTQPLGVYLLTPAVQDLWLRDKATFTCFVVG SDLKDAHLTWEVAGKVPTGGVEEGLLERHSNGSQSQHSRLTLPRSLWN AGTSVTCTLNHPSLPPQRLMALREPAAQAPVKLSLNLLASSDPPEAAS WLLCEVSGFSPPNILLMWLEDQREVNTSGFAPARPPPQPGSTTFWAWS VLRVPAPPSPQPATYTCVVSHEDSRTLLNASRSLEVSYVTDH | IgD-hinge-Fc |
| 6 | LEGGGEGRGSLLTCGDVEENPGPR | T2A |
| 7 | MLLLVTSLLLCELPHPAFLLIPRKVCNGIGIGEFKDSLSINATNIKHF KNCTSISGDLHILPVAFRGDSFTHTPPLDPQELDILKTVKEITGFLLI QAWPENRTDLHAFENLEIIRGRTKQHGQFSLAVVSLNITSLGLRSLKE ISDGDVIISGNKNLCYANTINWKKLFGTSGQKTKIISNRGENSCKATG QVCHALCSPEGCWGPEPRDCVSCRNVSRGRECVDKCNLLEGEPREFVE NSECIQCHPECLPQAMNITCTGRGPDNCIQCAHYIDGPHCVKTCPAGV MGENNTLVWKYADAGHVCHLCHPNCTYGCTGPGLEGCPTNGPKIPSIA TGMVGALLLLLVVALGIGLFM | tEGFR |
| 8 | FWVLVVVGGVLACYSLLVTVAFIIFWV | CD28 (amino acids 153-179 of Accession No. P10747) |
| 9 | IEVMYPPPYLDNEKSNGTIIHVKGKHLCPSPLFPGPSKPFWVLVVVGG VLACYSLLVTVAFIIFWV | CD28 (amino acids 114-179 of Accession No. P10747) |
| 10 | RSKRSRLLHSDYMNMTPRRPGPTRKHYQPYAPPRDFAAYRS | CD28 (amino acids 180-220 of P10747) |
| 11 | RSKRSRGGHSDYMNMTPRRPGPTRKHYQPYAPPRDFAAYRS | CD28 (LL to GG) |
| 12 | KRGRKKLLYIFKQPFMRPVQTTQEEDGCSCRFPEEEEGGCEL | 4-1BB (amino acids 214-255 of Q07011.1) |
| 13 | RVKFSRSADAPAYQQGQNQLYNELNLGRREEYDVLDKRRGRDPEMGGK PRRKNPQEGLYNELQKDKMAEAYSEIGMKGERRRGKGHDGLYQGLSTA TKDTYDALHMQALP | CD3 zeta |
| 14 | RVKFSRSAEPPAYQQGQNQLYNELNLGRREEYDVLDKRRGRDPEMGGK PRRKNPQEGLYNELQKDKMAEAYSEIGMKGERRRGKGHDGLYQGLSTA TKDTYDALHMQALPPR | CD3 zeta |
| 15 | RVKFSRSADAPAYKQGQNQLYNELNLGRREEYDVLDKRRGRDPEMGGK PRRKNPQEGLYNELQKDKMAEAYSEIGMKGERRRGKGHDGLYQGLSTA TKDTYDALHMQALPPR | CD3 zeta |
| 16 | RKVCNGIGIGEFKDSLSINATNIKHFKNCTSISGDLHILPVAFRGDSF THTPPLDPQELDILKTVKEITGFLLIQAWPENRTDLHAFENLEIIRGR TKQHGQFSLAVVSLNITSLGLRSLKEISDGDVIISGNKNLCYANTINW KKLFGTSGQKTKIISNRGENSCKATGQVCHALCSPEGCWGPEPRDCVS CRNVSRGRECVDKCNLLEGEPREFVENSECIQCHPECLPQAMNITCTG RGPDNCIQCAHYIDGPHCVKTCPAGVMGENNTLVWKYADAGHVCHLCH PNCTYGCTGPGLEGCPTNGPKIPSIATGMVGALLLLLVVALGIGLFM | tEGFR |
| 17 | EGRGSLLTCGDVEENPGP | T2A |
| 18 | GSGATNFSLLKQAGDVEENPGP | P2A |

-continued

| # | SEQUENCE | ANNOTATION |
|---|---|---|
| 19 | ATNFSLLKQAGDVEENPGP | P2A |
| 20 | QCTNYALLKLAGDVESNPGP | E2A |
| 21 | VKQTLNFDLLKLAGDVESNPGP | F2A |
| 22 | -PGGG-(SGGGG)5-P- wherein P is proline, G is glycine and S is serine | Linker |
| 23 | GSADDAKKDAAKKDGKS | Linker |
| 24 | atgcttctcctggtgacaagccttctgctctgtgagttaccacacccagcattcctcctgatccca | GMCSFR alpha chain signal sequence |
| 25 | MLLLVTSLLLCELPHPAFLLIP | GMCSFR alpha chain signal sequence |
| 26 | MALPVTALLLPLALLLHA | CD8 alpha signal peptide |
| 27 | EPKSCDKTHTCPPCP | Hinge |
| 28 | ERKCCVECPPCP | Hinge |
| 29 | ELKTPLGDTHTCPRCPEPKSCDTPPPCPRCPEPKSCDTPPPCPRCPEPKSCDTPPPCPRCP | Hinge |
| 30 | ESKYGPPCPSCP | Hinge |
| 31 | $X_1PPX_2P$<br>X1 is glycine, cysteine or arginine<br>X2 is cysteine or threonine | Hinge |
| 32 | YGPPCPPCP | Hinge |
| 33 | KYGPPCPPCP | Hinge |
| 34 | EVVVKYGPPCPPCP | Hinge |
| 35 | RASQDISKYLN | FMC63 CDR L1 |
| 36 | SRLHSGV | FMC63 CDR L2 |
| 37 | GNTLPYTFG | FMC63 CDR L3 |
| 38 | DYGVS | FMC63 CDR H1 |
| 39 | VIWGSETTYYNSALKS | FMC63 CDR H2 |
| 40 | YAMDYWG | FMC63 CDR H3 |
| 41 | EVKLQESGPGLVAPSQSLSVTCTVSGVSLPDYGVSWIRQPPRKGLEWLGVIWGSETTYYNSALKSRLTIIKDNSKSQVFLKMNSLQTDDTAIYYCAKHYYYGGSYAMDYWGQGTSVTVSS | FMC63 VH |
| 42 | DIQMTQTTSSLSASLGDRVTISCRASQDISKYLNWYQQKPDGTVKLLIYHTSRLHSGVPSRFSGSGSGTDYSLTISNLEQEDIATYFCQQGNTLPYTFGGGTKLEIT | FMC63 VL |
| 43 | DIQMTQTTSSLSASLGDRVTISCRASQDISKYLNWYQQKPDGTVKLLIYHTSRLHSGVPSRFSGSGSGTDYSLTISNLEQEDIATYFCQQGNTLPYTFGGGTKLEITGSTSGSGKPGSGEGSTKGEVKLQESGPGLVAPSQSLSVTCTVSGVSLPDYGVSWIRQPPRKGLEWLGVIWGSETTYYNSALKSRLTIIKDNSKSQVFLKMNSLQTDDTAIYYCAKHYYYGGSYAMDYWGQGTSVTVSS | FMC63 scFv |
| 44 | KASQNVGTNVA | SJ25C1 CDR L1 |
| 45 | SATYRNS | SJ25C1 CDR L2 |
| 46 | QQYNRYPYT | SJ25C1 CDR L3 |

| # | SEQUENCE | ANNOTATION |
|---|----------|------------|
| 47 | SYWMN | SJ25C1 CDR H1 |
| 48 | QIYPGDGDTNYNGKFKG | SJ25C1 CDR H2 |
| 49 | KTISSVVDFYFDY | SJ25C1 CDR H3 |
| 50 | EVKLQQSGAELVRPGSSVKISCKASGYAFSSYWMNWVKQRPGQGLEWI<br>GQIYPGDGDTNYNGKFKGQATLTADKSSSTAYMQLSGLTSEDSAVYFC<br>ARKTISSVVDFYFDYWGQGTTVTVSS | SJ25C1 VH |
| 51 | DIELTQSPKFMSTSVGDRVSVTCKASQNVGTNVAWYQQKPGQSPKPLI<br>YSATYRNSGVPDRFTGSGSGTDFTLTITNVQSKDLADYFCQQYNRYPY<br>TSGGGTKLEIKR | SJ25C1 VL |
| 52 | GGGGSGGGGSGGGGS | Linker |
| 53 | EVKLQQSGAELVRPGSSVKISCKASGYAFSSYWMNWVKQRPGQGLEWI<br>GQIYPGDGDTNYNGKFKGQATLTADKSSSTAYMQLSGLTSEDSAVYFC<br>ARKTISSVVDFYFDYWGQGTTVTVSSGGGGSGGGGSGGGGSDIELTQS<br>PKFMSTSVGDRVSVTCKASQNVGTNVAWYQQKPGQSPKPLIYSATYRN<br>SGVPDRFTGSGSGTDFTLTITNVQSKDLADYFCQQYNRYPYTSGGGTK<br>LEIKR | SJ25C1 scFv |
| 54 | HYYYGGSYAMDY | FMC63 HC-CDR3 |
| 55 | HTSRLHS | FMC63 LC-CDR2 |
| 56 | QQGNTLPYT | FMC63 LC-CDR3 |
| 57 | gacatccagatgacccagaccacctccagcctgagcgccagcctgggc<br>gaccgggtgaccatcagctgccgggccagccaggacatcagcaagtac<br>ctgaactggtatcagcagaagcccgacggcaccgtcaagctgctgatc<br>taccacaccagccggctgcacagcggcgtgcccagccggtttagcggc<br>agcggctccggcaccgactacagcctgaccatctccaacctggaacag<br>gaagatatcgccacctacttttgccagcagggcaacacactgccctac<br>acctttggcggcggaacaaagctggaaatcaccggcagcacctccggc<br>agcggcaagcctggcagcggcgagggcagcaccaagggcgaggtgaag<br>ctgcaggaaagcggccctggcctggtggccccagccagagcctgagc<br>gtgacctgcaccgtgagcggcgtgagcctgcccgactacggcgtgagc<br>tggatccggcagccccccaggaagggcctggaatggctgggcgtgatc<br>tggggcagcgagaccacctactacaacagcgccctgaagagccggctg<br>accatcatcaaggacaacagcaagagccaggtgttcctgaagatgaac<br>agcctgcagaccgacgacaccgccatctactactgcgccaagcactac<br>tactacggcggcagctacgccatggactactggggccagggcaccagc<br>gtgaccgtgagcagc | Sequence encoding scFv |
| 58 | GSTSGSGKPGSGEGSTKG | Linker |
| 59 | ASTKGPSVFPLAPCSRSTSESTAALGCLVKDYFPEPVTVSWNSGALTS<br>GVHTFPAVLQSSGLYSLSSVVTVPSSNFGTQTYTCNVDHKPSNTKVDK<br>TVERKCCVECPPCPAPPVAGPSVFLFPPKPKDTLMISRTPEVTCVVVD<br>VSHEDPEVQFNWYVDGVEVHNAKTKPREEQFNSTFRVVSVLTVVHQDW<br>LNGKEYKCKVSNKGLPAPIEKTISKTKGQPREPQVYTLPPSREEMTKN<br>QVSLTCLVKGFYPSDISVEWESNGQPENNYKTTPPMLDSDGSFFLYSK<br>LTVDKSRWQQGNVFSCSVMHEALHNHYTQKSLSLSPGK | Human IgG2 Fc<br>(Uniprot P01859) |
| 60 | ASTKGPSVFPLAPCSRSTSESTAALGCLVKDYFPEPVTVSWNSGALTS<br>GVHTFPAVLQSSGLYSLSSVVTVPSSSLGTKTYTCNVDHKPSNTKVDK<br>RVESKYGPPCPSCPAPEFLGGPSVFLFPPKPKDTLMISRTPEVTCVVV<br>DVSQEDPEVQFNWYVDGVEVHNAKTKPREEQFNSTYRVVSVLTVLHQD<br>WLNGKEYKCKVSNKGLPSSIEKTISKAKGQPREPQVYTLPPSQEEMTK<br>NQVSLTCLVKGFYPSDIAVEWESNGQPENNYKTTPPVLDSDGSFFLYS<br>RLTVDKSRWQEGNVFSCSVMHEALHNHYTQKSLSLSLGK | Human IgG4 Fc<br>(Uniprot P01861) |
| 61 | mrkllifsisaylmagivsckgvdsatpvtedrlalnavnapadntvn<br>iktfdkvknafgdglsqsaegtftfpadvavktikmfiknecpnktcd<br>ewdryanvyvknkttgewyeigrfitpywygteklprgleidvtdflc<br>sllsgntelkiytetwlakgreysvdfdivygtpdykysavvpviqyn<br>kssidgvpygkahtlglkkniqlptntekaylrttisgwghakpydag<br>srgcaewcfrthtiainnantfqhqlgalgcsanpinnqspgnwapdr<br>agwcpgmayptridvinnsligtfsyeykfqswtnngtngdafyais<br>sfviaksntpisapvvtn | Amino acid<br>sequence of<br>PNGase F from<br>*Flavobacterium*<br>*meningosepticum* |

What is claimed:

1. A method of assessing surface proteins of an engineered cell composition, the method comprising:
   (a) labeling one or more surface proteins present on cells of a sample from an engineered cell composition or a subset of such cells, the engineered cell composition comprising cells comprising a recombinant receptor, thereby generating a labeled cell composition;
   (b) lysing cells of the labeled cell composition, thereby generating a lysed cell composition;
   (c) isolating the one or more surface proteins from the lysed cell composition to obtain one or more isolated proteins; and
   (d) subjecting the one or more isolated proteins to a mass spectrometry (MS) technique to obtain a MS profile comprising one or more data components.

2. The method of claim 1, wherein the method further comprises digesting the one or more isolated proteins prior to step (d).

3. The method of claim 2, wherein the digesting is carried out by proteolysis in the presence of one or more proteases capable of cleaving one or more peptide bonds.

4. The method of claim 1, wherein the one or more isolated proteins comprise cell surface membrane proteins.

5. The method of claim 1, wherein the lysing of the cells comprises incubation in the presence of a detergent.

6. The method of claim 1, wherein the labeling of the one or more surface proteins comprises biotin labeling of primary amines.

7. The method of claim 1, wherein the MS technique comprises subjecting the sample to liquid chromatography (LC) followed by MS.

8. The method of claim 1, wherein the at least one data component comprises one or more of MS ion information, total ion chromatograph (TIC) or a portion thereof, extracted ion chromatogram (XIC) or a portion thereof, peptide MS ion signal peak, protein MS ion signal peak, peptide identification information, protein identification information, qualitative information, quantitative information, structural information, and post-translation modifications.

9. The method of claim 8, wherein the at least one data component is an XIC or a portion thereof, wherein the XIC or portion thereof is based on one or more theoretical or known m/z values of one or more peptide components of the recombinant receptor.

10. The method of claim 9, wherein the one or more peptide components is a proteolytically cleaved or digested peptide component.

11. The method of claim 1, wherein the recombinant receptor is or comprises a T cell receptor (TCR) or antigen-binding fragment thereof.

12. The method of claim 1, wherein the recombinant receptor is a chimeric antigen receptor (CAR).

13. The method of claim 1, wherein the sample comprises recombinant receptor+CD3+ cells in a cell composition.

14. The method of claim 1, wherein the sample comprises recombinant receptor+CD8+ cells in a cell composition or recombinant receptor+CD4+ cells in a cell composition.

15. The method of claim 1, wherein the MS profile is a test MS profile, the method further comprising comparing the test MS profile to a reference MS profile.

16. The method of claim 15, wherein the reference MS profile comprises one or more data components comprising information from a sample from a reference cell composition.

17. The method of claim 16, wherein the reference cell composition comprises immune cells that do not contain a nucleic acid encoding the recombinant receptor.

18. The method of claim 15, further comprising identifying one or more differences in the presence, absence, or level of one or more data components in the test MS profile compared to the reference MS profile.

19. A method of assessing surface proteins of an engineered cell composition, the method comprising:
 (a) labeling one or more surface proteins present on cells of a sample from an engineered cell composition or a subset of such cells, the engineered cell composition comprising cells comprising a recombinant receptor, thereby generating a labeled cell composition;
 (b) lysing cells of the labeled cell composition, thereby generating a lysed cell composition;
 (c) digesting and isolating the one or more surface proteins from the lysed cell composition to obtain one or more isolated proteins; and
 (d) subjecting the one or more isolated proteins to a mass spectrometry (MS) technique to obtain a MS profile comprising one or more data components.

20. The method of claim 19, wherein the recombinant receptor is or comprises a T cell receptor (TCR) or a chimeric antigen receptor (CAR).

21. The method of claim 19, wherein the labeling of the one or more surface proteins comprises biotin labeling of primary amines.

* * * * *